US009675357B2

(12) United States Patent
Suyker et al.

(10) Patent No.: US 9,675,357 B2
(45) Date of Patent: Jun. 13, 2017

(54) APPARATUS FOR PERFORMING VASCULAR ANASTOMOSIS

(71) Applicant: Innovative Interventional Technologies B.V., Amsterdam (NL)

(72) Inventors: Wilhelmus Joseph Leonardus Suyker, Zwolle (NL); Paulus Thomas Wilhelmus Suyker, Amsterdam (NL)

(73) Assignee: Innovative Interventional Technologies, B.V., Amsterdam (NL)

( * ) Notice: Subject to any disclaimer, the term of this patent is extended or adjusted under 35 U.S.C. 154(b) by 500 days.

(21) Appl. No.: 14/450,462

(22) Filed: Aug. 4, 2014

(65) Prior Publication Data

US 2015/0025554 A1 Jan. 22, 2015

Related U.S. Application Data

(63) Continuation of application No. 12/348,139, filed on Jan. 2, 2009, now Pat. No. 8,858,579, which is a
(Continued)

(51) Int. Cl.
*A61B 17/068* (2006.01)
*A61B 17/11* (2006.01)
(Continued)

(52) U.S. Cl.
CPC ............ *A61B 17/11* (2013.01); *A61B 17/068* (2013.01); *A61B 17/0644* (2013.01);
(Continued)

(58) Field of Classification Search
CPC ... A61B 17/11; A61B 17/115; A61B 17/1155; A61B 17/0641; A61B 17/0644;
(Continued)

(56) References Cited

U.S. PATENT DOCUMENTS 3,552,626 A 1/1971 Astafiev et al.
4,018,228 A 4/1977 Goosen
(Continued)

FOREIGN PATENT DOCUMENTS

WO 0027311 5/2000
WO WO0069364 A2 11/2000
(Continued)

OTHER PUBLICATIONS

European Office Action; Mailed Apr. 5, 2016 for EP Application No. EP05725061.5.
(Continued)

*Primary Examiner* — Scott A. Smith
(74) *Attorney, Agent, or Firm* — Mendelsohn Dunleavy, P.C.

(57) ABSTRACT

A method for performing a coronary artery bypass graft procedure on a patient to connect a bypass vessel to a target vessel includes the steps of creating an opening in the patient that communicates with the thoracic cavity of the patient; providing a bypass vessel having a lumen and at least one free end; passing the free end of the bypass vessel from the thoracic cavity through the opening to a position outside the body of the patient; attaching a connector to the free end of bypass vessel while the free end of the bypass vessel is outside the body of the patient; passing the free end of the bypass vessel from the position outside the body of the patient through the opening and into the thoracic cavity; and connecting the free end of the bypass vessel to a target vessel with the connector.

19 Claims, 70 Drawing Sheets

Related U.S. Application Data continuation of application No. 10/977,756, filed on Oct. 29, 2004, now abandoned.

(60) Provisional application No. 60/551,609, filed on Mar. 9, 2004.

(51) Int. Cl.
*A61B 17/064* (2006.01)
*A61B 17/072* (2006.01)
*A61B 17/00* (2006.01)
*A61B 17/115* (2006.01)
*A61B 17/32* (2006.01)
*A61B 17/3207* (2006.01)
*A61B 17/22* (2006.01)
*A61B 17/29* (2006.01)
*A61B 90/00* (2016.01)

(52) U.S. Cl.
CPC ..... *A61B 17/00491* (2013.01); *A61B 17/0686* (2013.01); *A61B 17/1155* (2013.01); *A61B 17/320016* (2013.01); *A61B 17/320783* (2013.01); *A61B 2017/00539* (2013.01); *A61B 2017/00867* (2013.01); *A61B 2017/0641* (2013.01); *A61B 2017/07214* (2013.01); *A61B 2017/1107* (2013.01); *A61B 2017/1135* (2013.01); *A61B 2017/22042* (2013.01); *A61B 2017/22044* (2013.01); *A61B 2017/2917* (2013.01); *A61B 2017/2919* (2013.01); *A61B 2017/2937* (2013.01); *A61B 2017/320056* (2013.01); *A61B 2090/08021* (2016.02)

(58) Field of Classification Search
CPC . A61B 17/068; A61B 17/0686; A61B 17/072; A61B 17/320016; A61B 17/320783; A61B 2017/00539; A61B 2017/00867; A61B 2017/0641; A61B 2017/1107; A61B 2017/2917; A61B 2017/22044; A61B 2017/07214
USPC .......... 227/19, 175.1, 176.1, 180.1; 606/139, 606/153, 219
See application file for complete search history.

(56) References Cited

U.S. PATENT DOCUMENTS

| | | | |
|---|---|---|---|
| 4,216,776 A | 8/1980 | Downie et al. | |
| 4,304,236 A | 12/1981 | Conta et al. | |
| 4,505,272 A | 3/1985 | Utyamyshev et al. | |
| 4,747,407 A | 5/1988 | Liu et al. | |
| 4,779,628 A | 10/1988 | Machek | |
| 4,893,622 A | 1/1990 | Green et al. | |
| 4,907,591 A | 3/1990 | Vasconcellos et al. | |
| 5,119,983 A | 6/1992 | Green et al. | |
| 5,141,516 A | 8/1992 | Detweiler | |
| 5,234,447 A | 8/1993 | Kaster et al. | |
| 5,348,259 A | 9/1994 | Blanco et al. | |
| 5,395,030 A | 3/1995 | Kuramoto et al. | |
| 5,503,635 A | 4/1996 | Sauer et al. | |
| 5,690,662 A | 11/1997 | Chiu et al. | |
| 5,695,504 A | 12/1997 | Gifford, III et al. | |
| 5,702,412 A | 12/1997 | Popov et al. | |
| 5,709,335 A | 1/1998 | Heck | |
| 5,716,370 A | 2/1998 | Williamson, IV et al. | |
| 5,817,113 A | 10/1998 | Gifford, III et al. | |
| 5,893,369 A | 4/1999 | LeMole | |
| 5,904,697 A | 5/1999 | Gifford, III et al. | |
| 5,951,576 A | 9/1999 | Wakabayashi | |
| 6,027,476 A * | 2/2000 | Sterman ........... A61B 17/00234 604/6.14 |
| 6,030,395 A | 2/2000 | Nash et al. | |
| 6,035,856 A | 3/2000 | LaFontaine et al. | |
| 6,152,937 A | 11/2000 | Peterson et al. | |
| 6,176,864 B1 | 1/2001 | Chapman | |
| 6,248,112 B1 * | 6/2001 | Gambale ............ A61B 17/3468 606/108 |
| 6,258,107 B1 | 7/2001 | Balazs et al. | |
| 6,428,555 B1 | 8/2002 | Koster, Jr. | |
| 6,530,932 B1 | 3/2003 | Swayze et al. | |
| 6,551,334 B2 | 4/2003 | Blatter et al. | |
| 6,569,173 B1 | 5/2003 | Blatter et al. | |
| 8,858,579 B2 * | 10/2014 | Suyker ............... A61B 17/0644 606/153 |
| 2004/0215221 A1 | 10/2004 | Suyker et al. | |

FOREIGN PATENT DOCUMENTS

| | | |
|---|---|---|
| WO | 03003926 | 1/2003 |
| WO | 03038055 | 5/2003 |

OTHER PUBLICATIONS

European Examination Report; Mailed Dec. 15, 2014 for the corresponding EP Application No. EP05725061.5.
File History for U.S. Appl. No. 12/348,139.
Supplemental EP Search Report, EP 05 72 5061, Jan. 16, 2012.
Non-Final Office Action; Mailed Apr. 13, 2007 for related U.S. Appl. No. 10/977,756.
Non-Final Office Action; Mailed Dec. 31, 2008 for related U.S. Appl. No. 10/977,756.
Final Office Action; Mailed Oct. 3, 2008 for related U.S. Appl. No. 10/977,756.
Non-Final Office Action; Mailed Jun. 15, 2011 for related U.S. Appl. No. 12/348,139.
Non-Final Office Action; Mailed Jan. 20, 2012 for related U.S. Appl. No. 12/348,139.
Final Office Action; Mailed Feb. 12, 2014 for related U.S. Appl. No. 12/348,139.
Notice of Allowance; Mailed Jun. 10, 2014 for related U.S. Appl. No. 12/348,139.

* cited by examiner

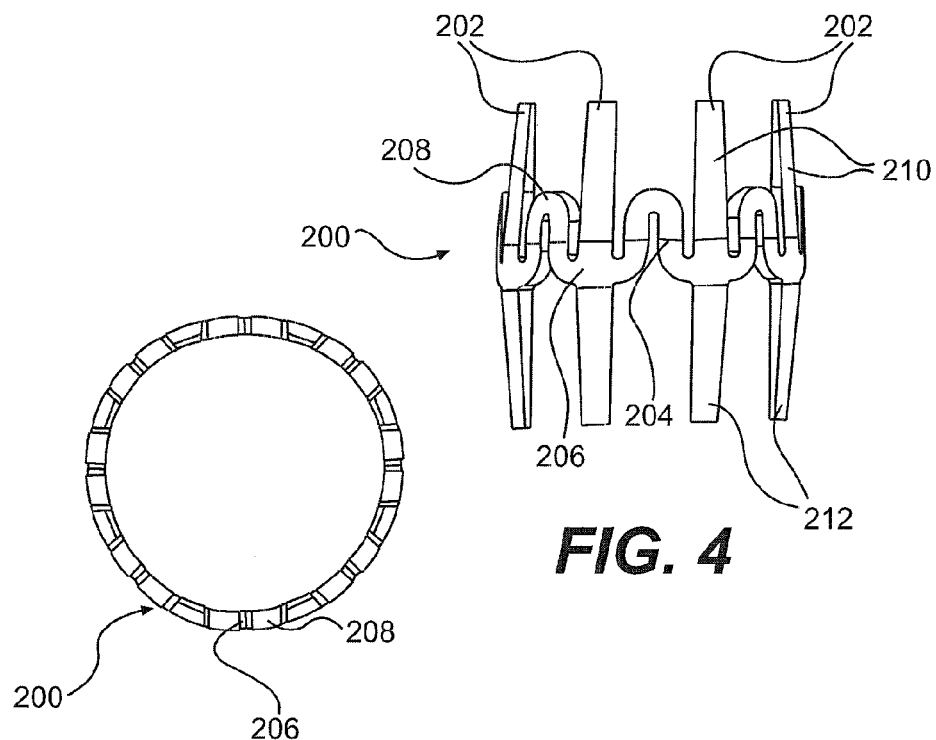
FIG. 4
FIG. 5
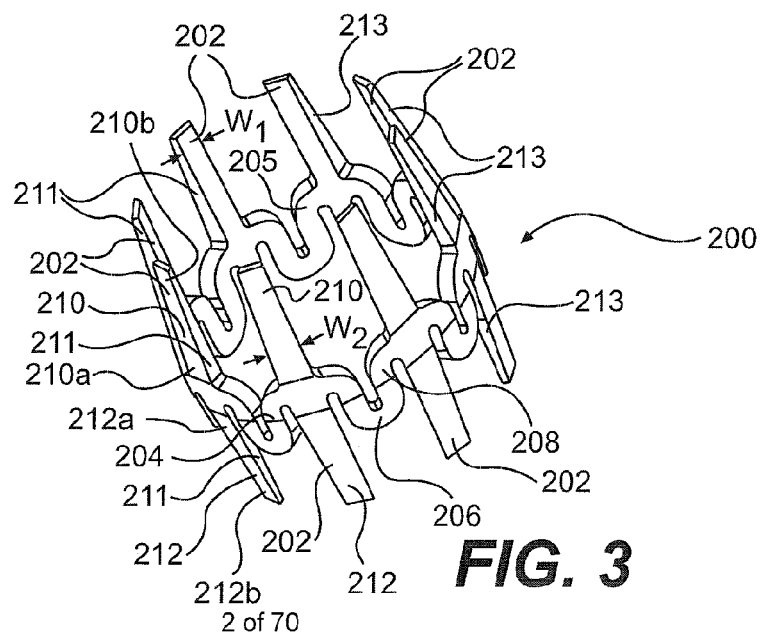
FIG. 3

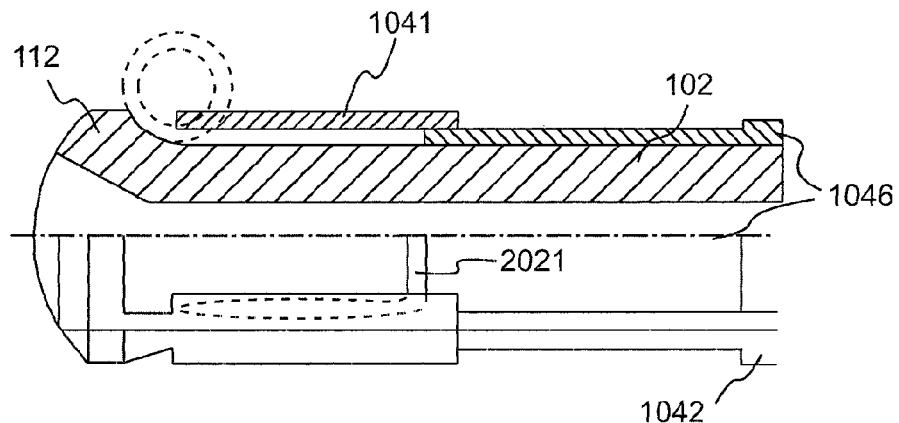
FIG. 8A
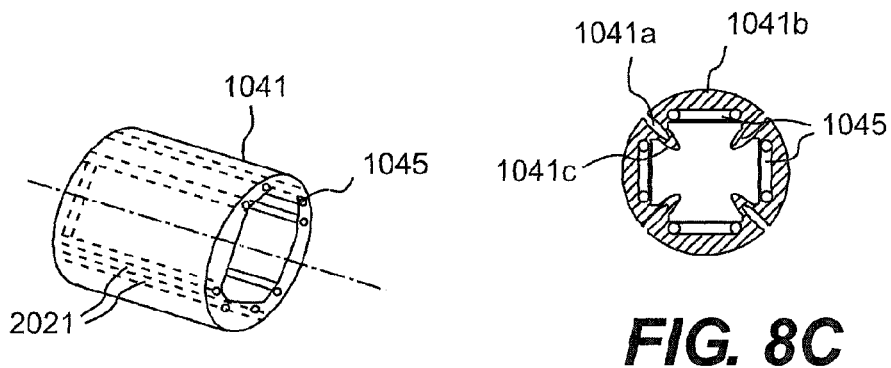
FIG. 8B
FIG. 8C
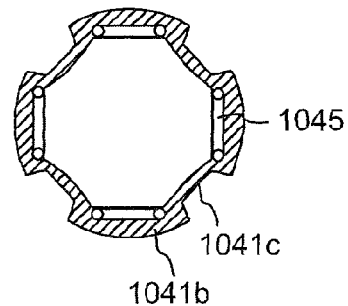
FIG. 8D

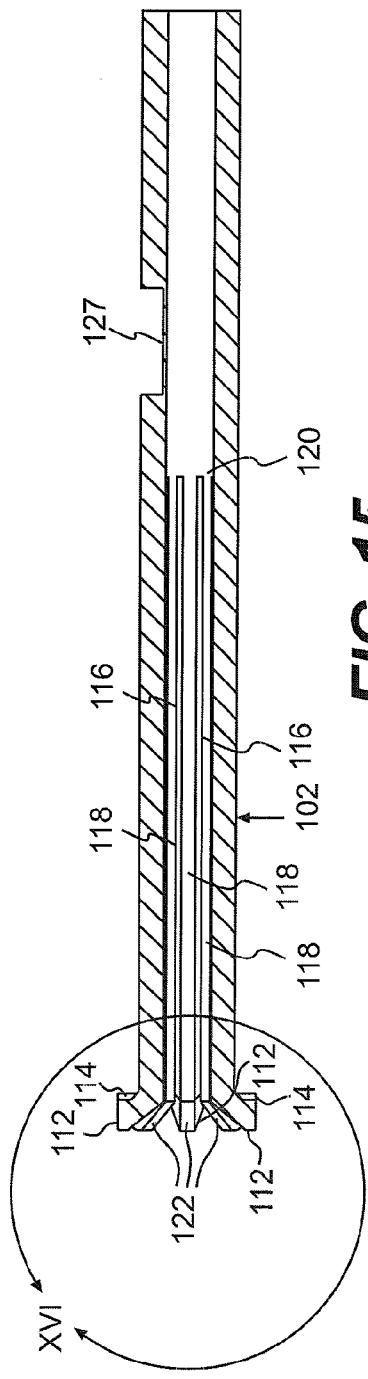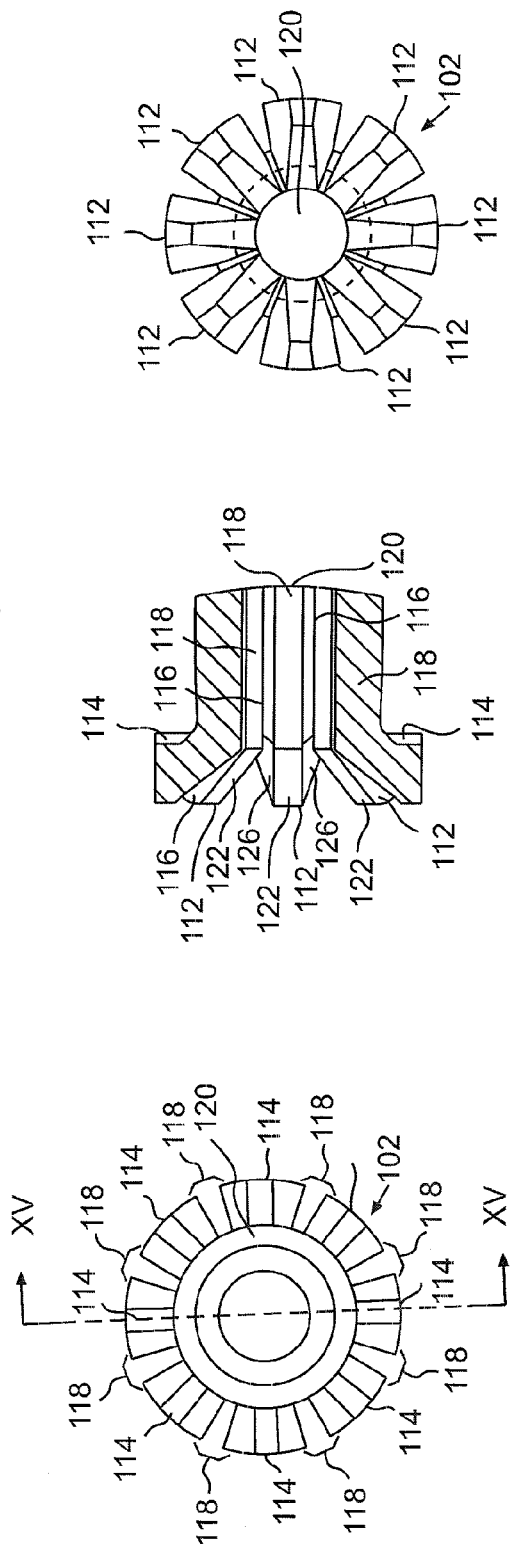

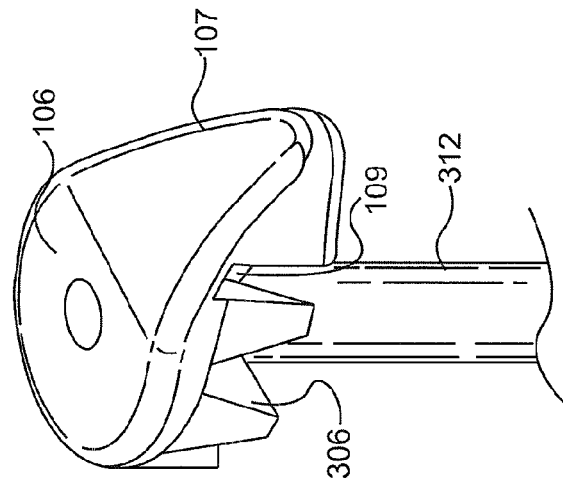
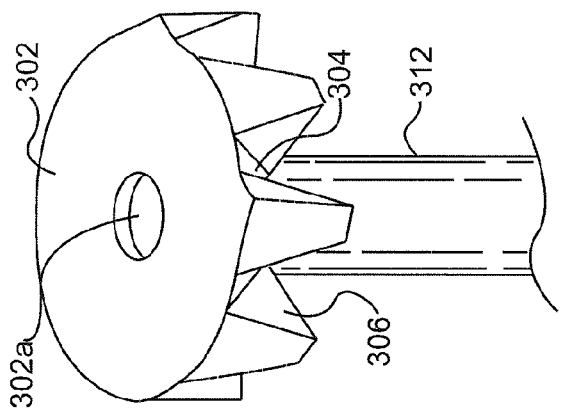
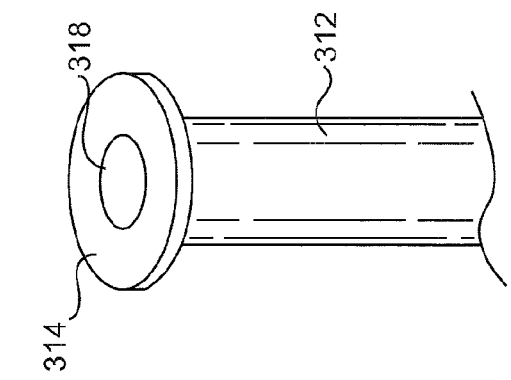
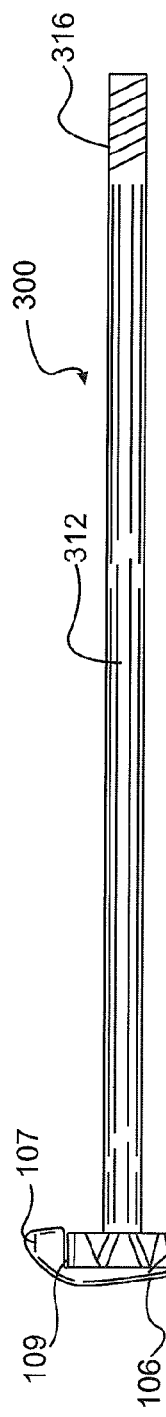

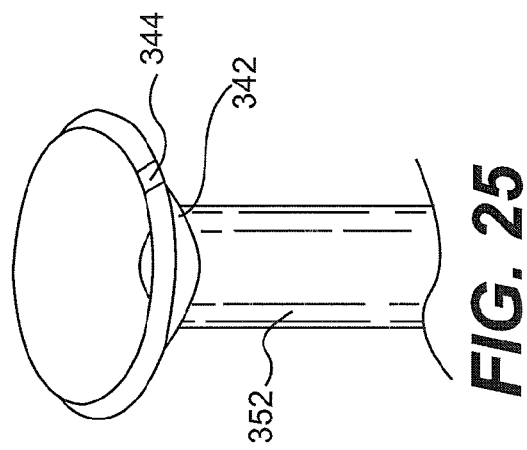
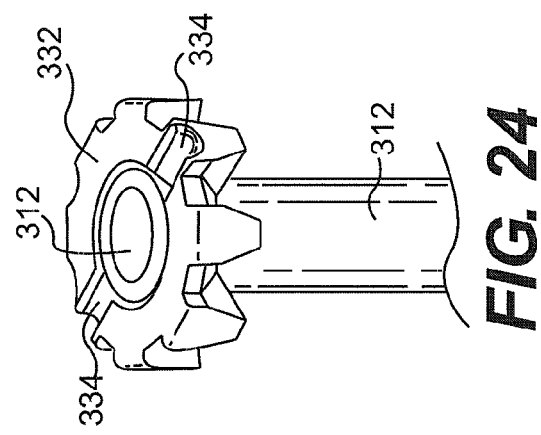
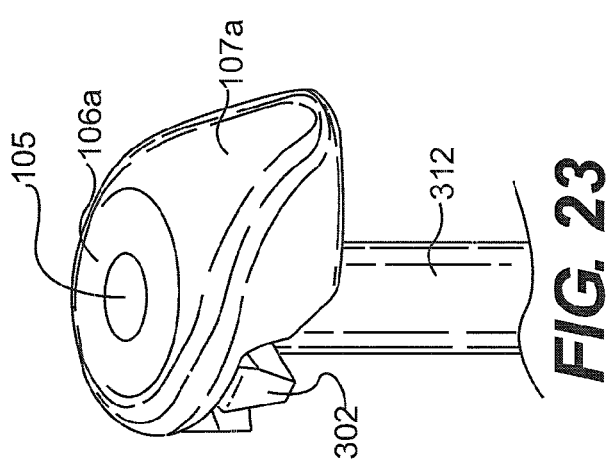
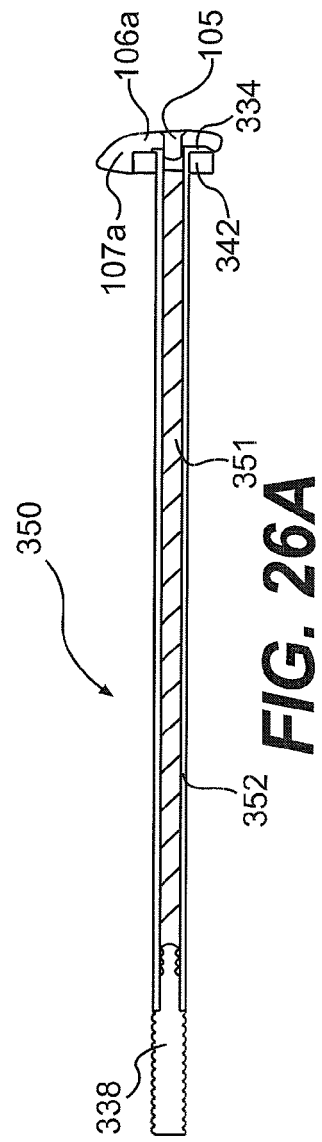

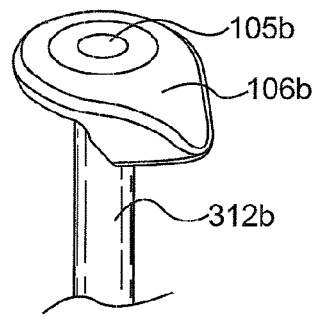
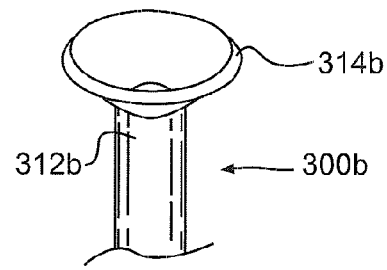
FIG. 27A    FIG. 27B
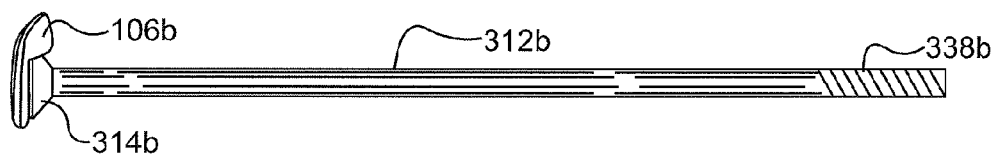
FIG. 27C
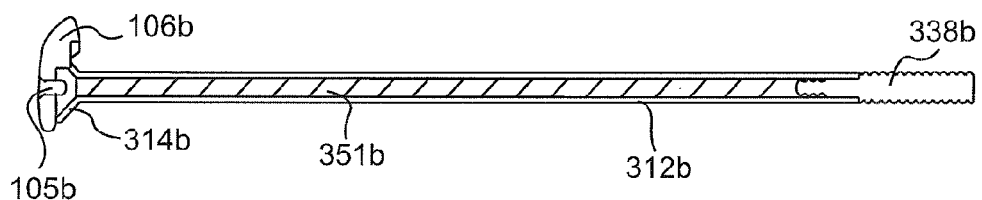
FIG. 27D

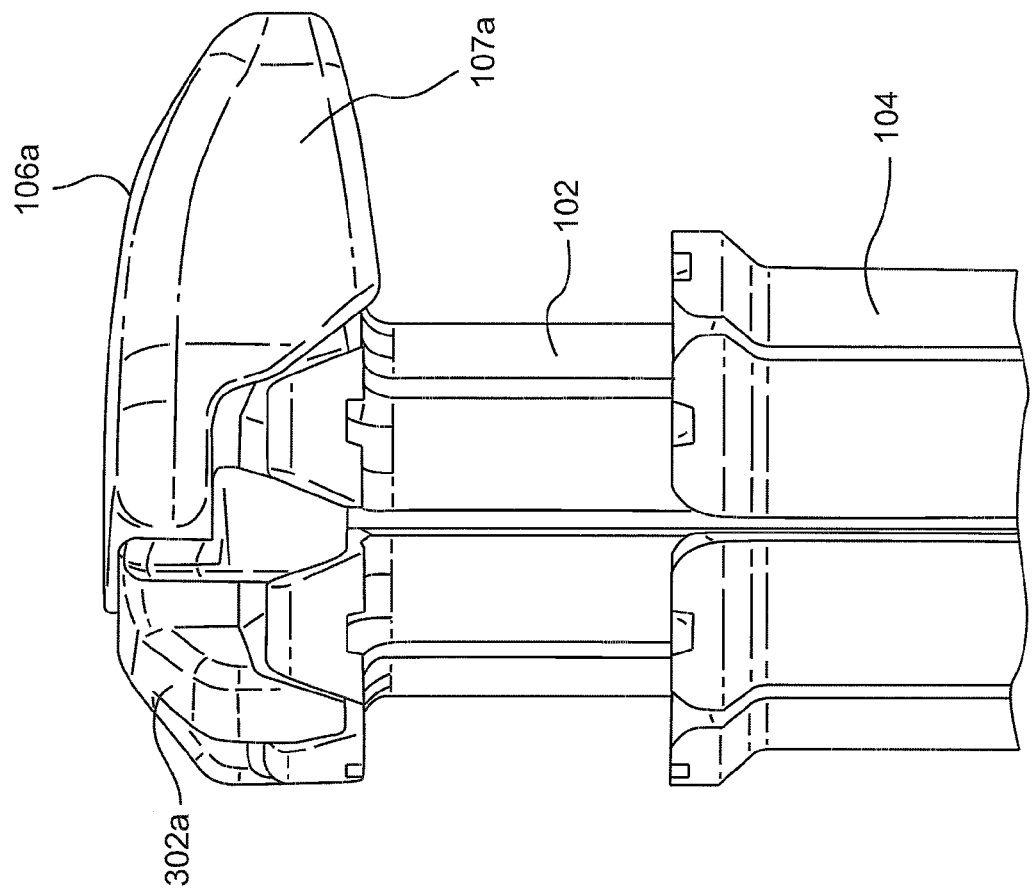

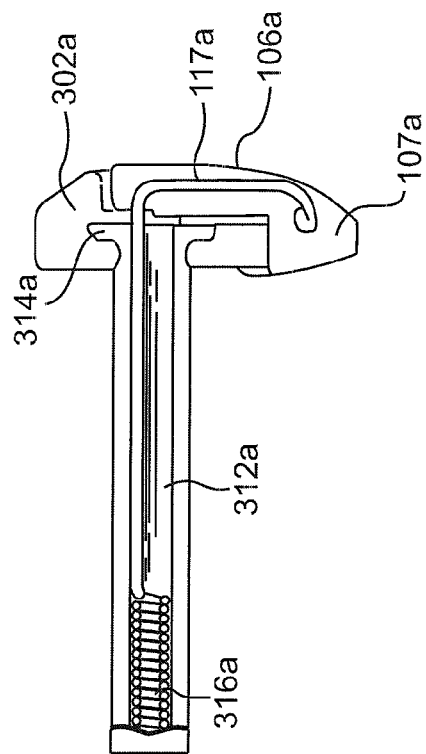
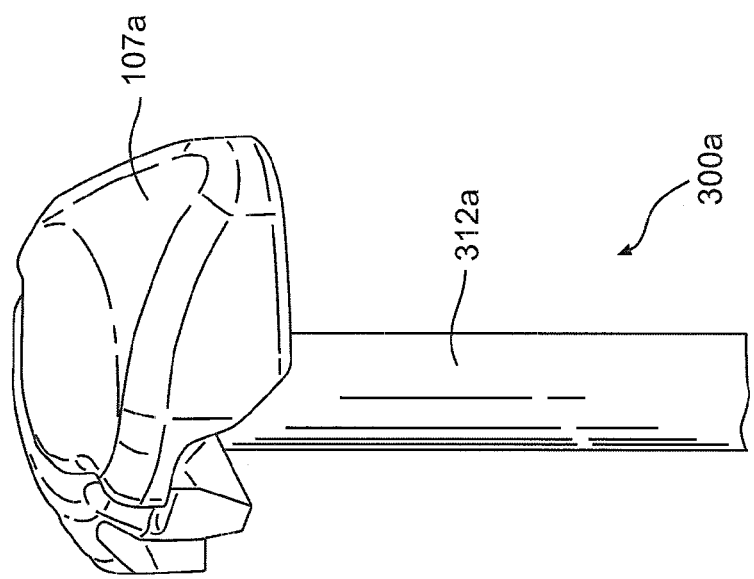
FIG. 28C
FIG. 28B

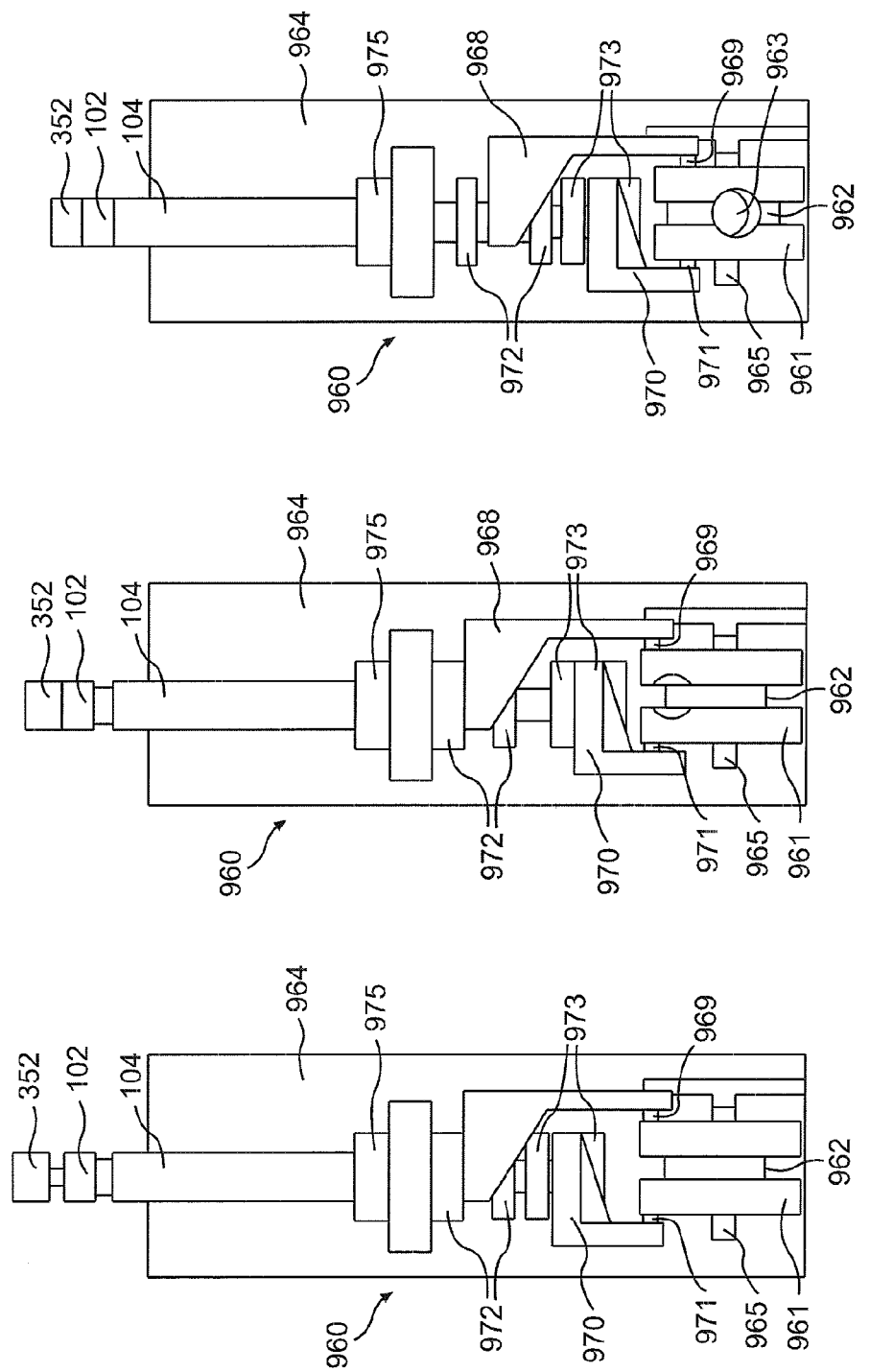

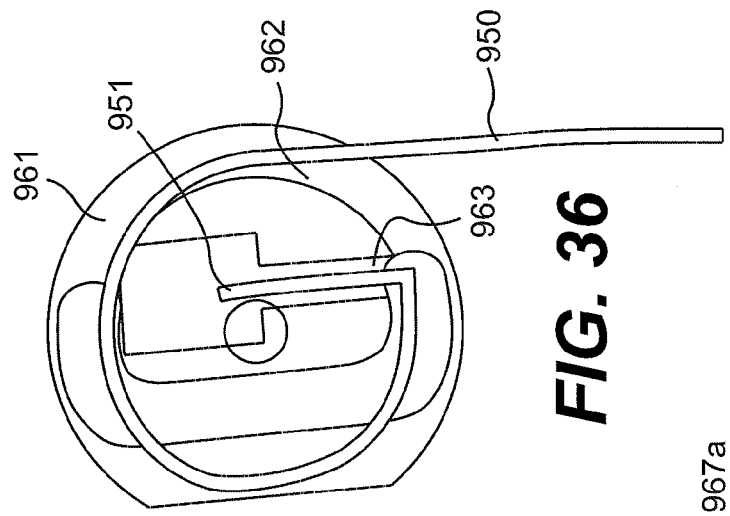
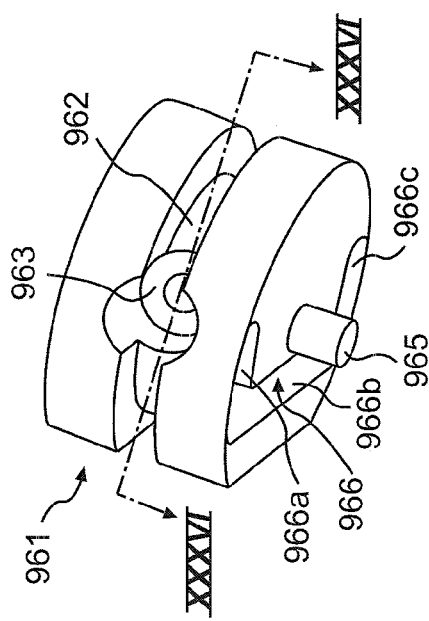
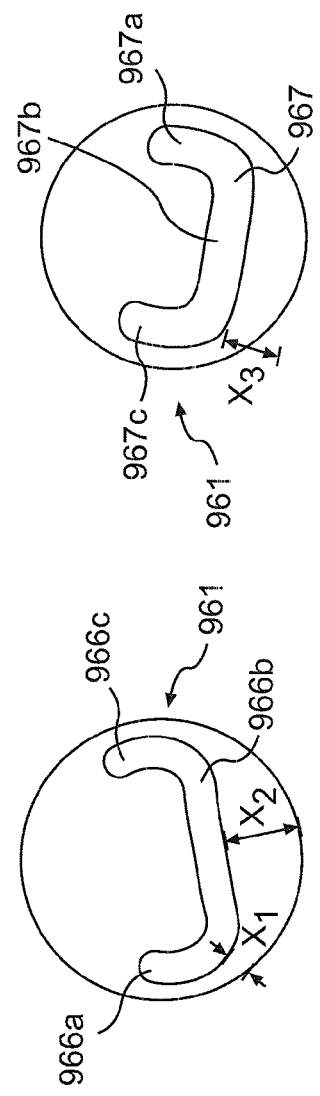
FIG. 36
FIG. 34
FIG. 37
FIG. 35

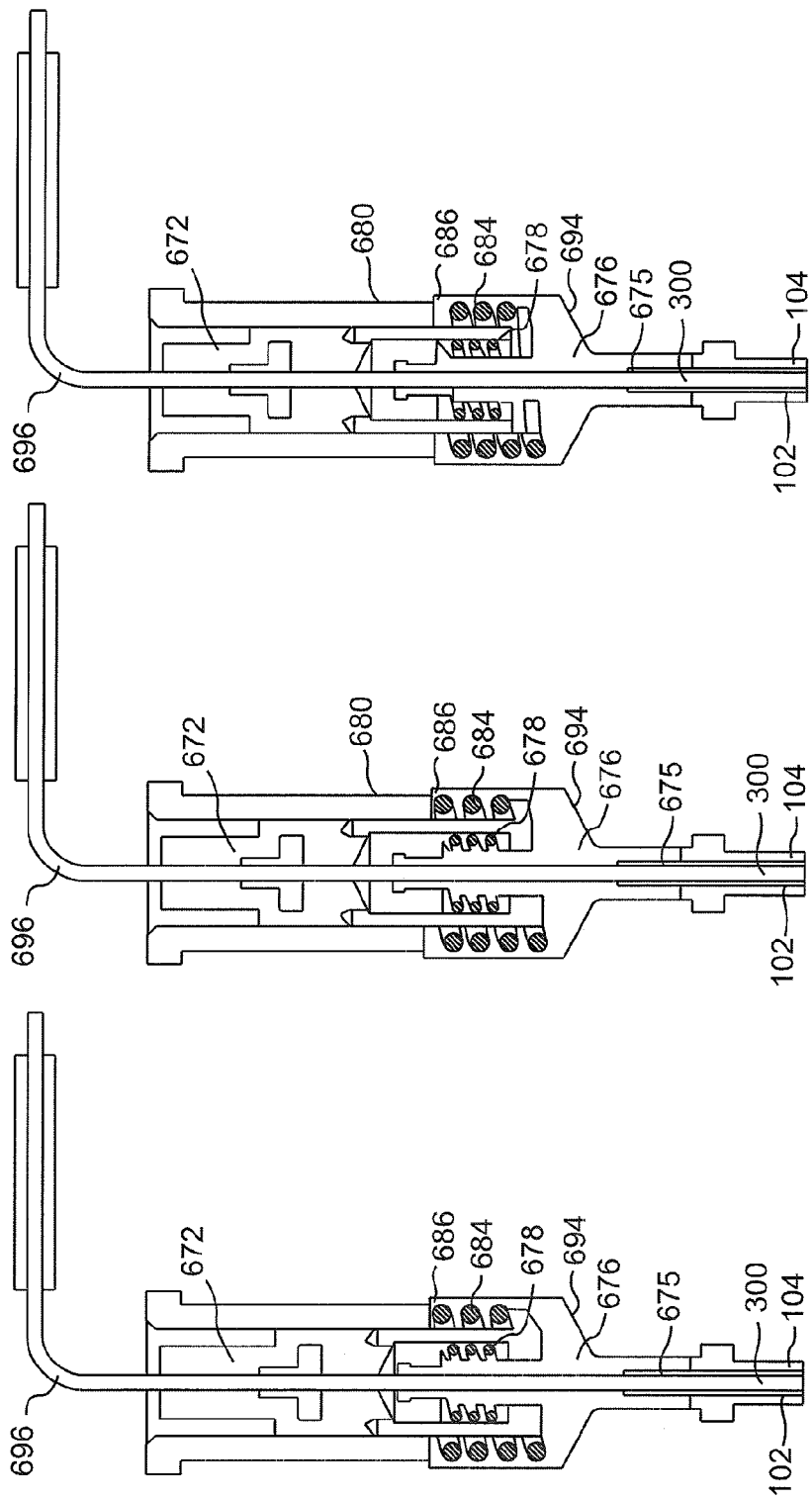

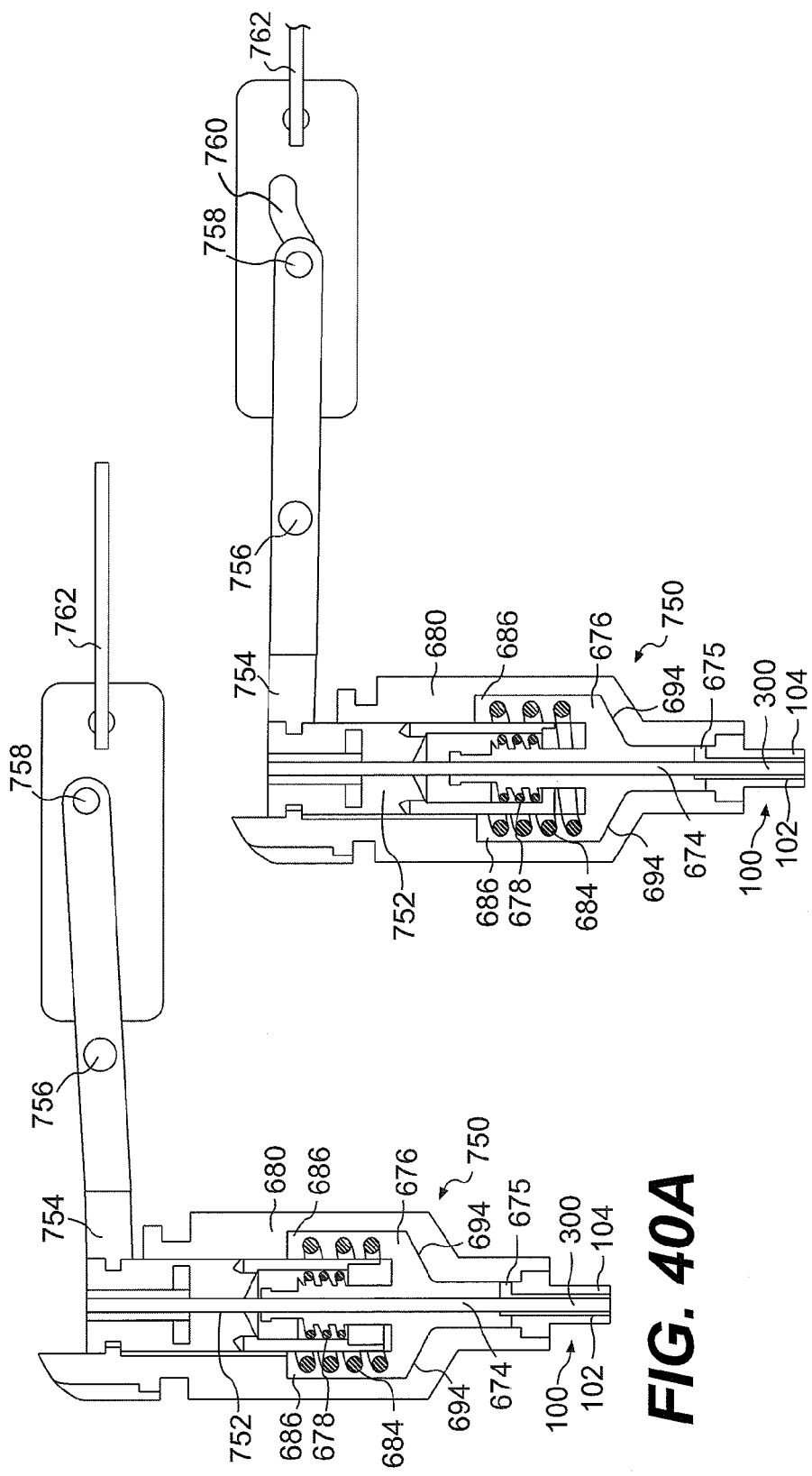

READY STATE

INTERMEDIATE STATE

FINAL STATE

READY STATE

INTERMEDIATE STATE

FINAL STATE

READY STATE

INTERMEDIATE STATE

RELEASE STATE

FINAL STATE

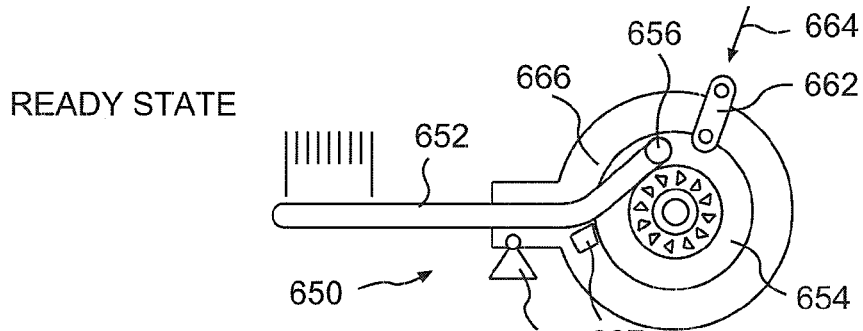
FIG. 51A READY STATE
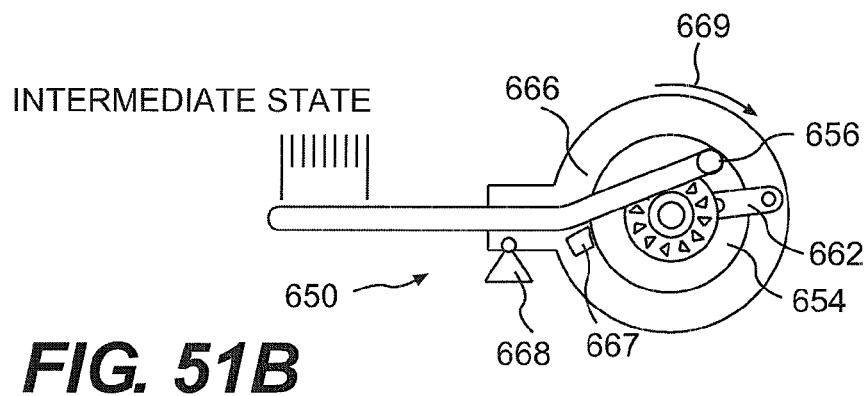
FIG. 51B INTERMEDIATE STATE
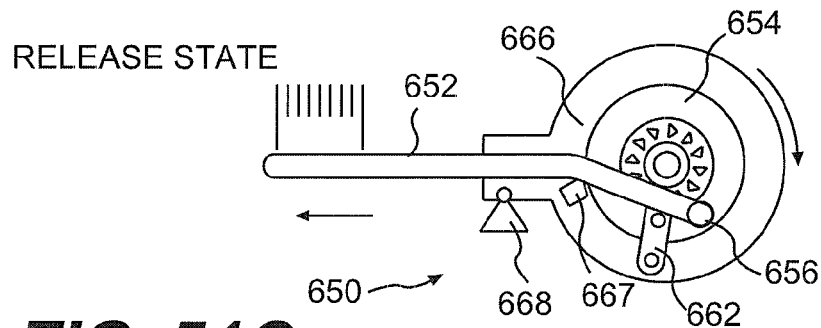
FIG. 51C RELEASE STATE
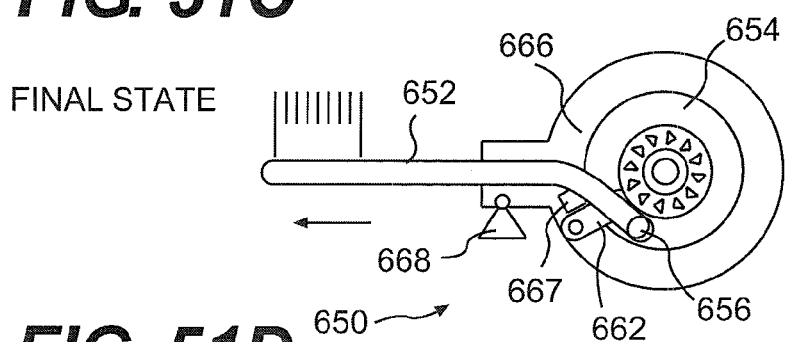
FIG. 51D FINAL STATE

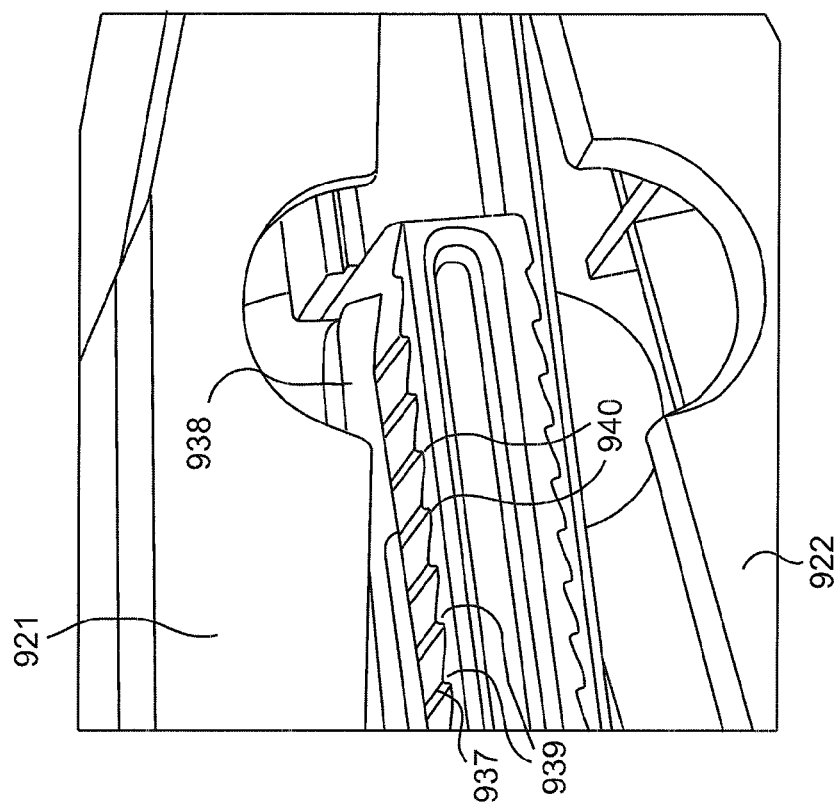

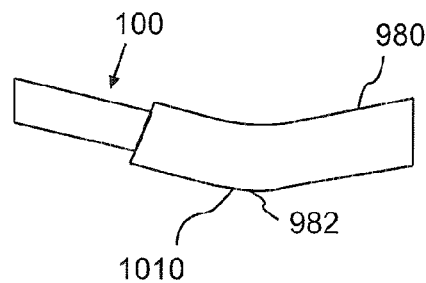
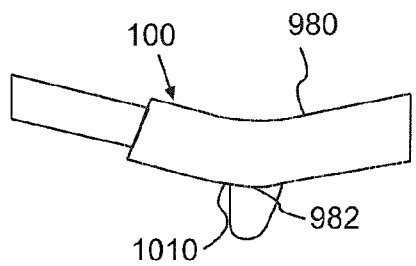
FIG. 64A                FIG. 64B
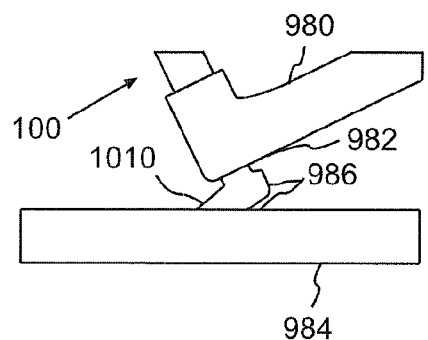
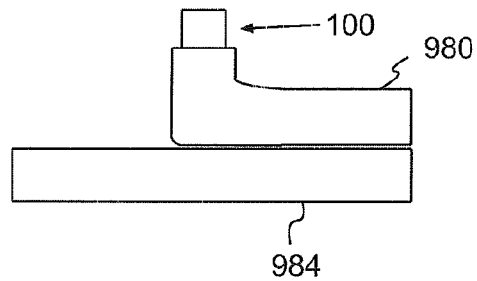
FIG. 64C                FIG. 64D

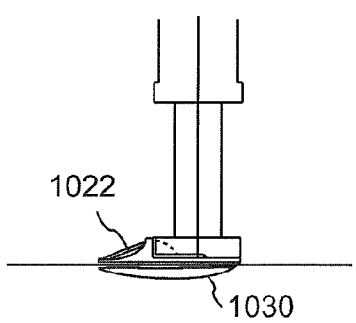
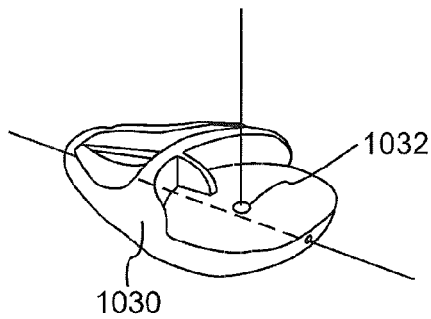
FIG. 67A  FIG. 67B
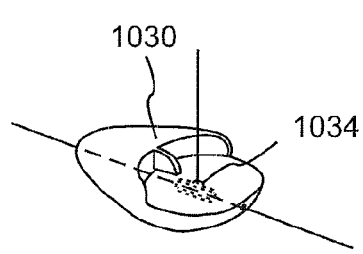
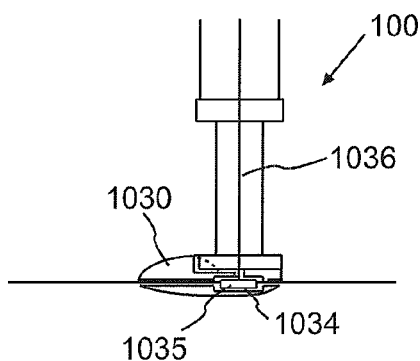
FIG. 67C  FIG. 67D

APPARATUS FOR PERFORMING VASCULAR ANASTOMOSIS

FIELD OF THE INVENTION

The present invention relates generally to apparatus and methods for performing a vascular anastomosis. More particularly, the present invention relates to a vascular anastomosis apparatus for joining a graft vessel, such as a coronary bypass graft, to the sidewall of an existing vessel, such as a coronary artery.

BACKGROUND OF THE INVENTION

Anastomosis is the surgical joining of tissues of tubular structures having a lumen, such as blood vessels, to create communication between the lumina of the structures. Anastomoses are employed in, for example, vascular surgery, for the purpose of creating or restoring blood flow pathways. One example of this is coronary artery bypass surgery (CABG), a procedure designed to restore blood flow to portions of the heart whose blood supply has been reduced by occlusion or stenosis of at least one coronary artery.

One method for CABG involves harvesting a saphenous vein from the patient's body, or using an artificial conduit, and connecting the vein or conduit to the occluded or stenosed artery as a bypass graft from another artery, such as the aorta, downstream of the occlusion or stenosis. In this method, the bypass graft must be attached to the sides of existing arteries at both the proximal and distal ends of the graft by proximal and distal anastomoses.

An alternative method involves rerouting a less important artery from its normal location to another location downstream of the occlusion or stenosis. In this method, only a distal anastomosis between the distal end of the graft and the side of an existing artery may be required to complete the procedure.

One method for performing vascular anastomosis is by hand suturing. This is a time-consuming and difficult task requiring a high degree of surgical skill to perform successfully due to the considerable perfection, required to achieve reliable and consistent functionality. The procedure poses consequently a relatively high risk to the patient, because the overall outcome is so much dependent on this functionality. Not only does the surgeon have to provide a leak-free connection of vessels so small, that optical magnification is routinely used, but also the anastomosis must provide a smooth, open flow path for the blood. In this method, there is frequently a need for additional suturing of the anastomosis to close any leaks that are detected. Besides the required precision, the time-consuming nature of a hand-sutured anastomosis is of special concern.

Since in CABG, anastomoses have to be constructed on a constantly moving, extremely vital organ, the operative technique needs a careful setup. In the majority of cases, the patient is typically supported on cardiopulmonary bypass (CPB) for most of the surgical procedure. The heart can then be safely stopped by cross-clamping the aorta to isolate it from the systemic circulation and perfusing it with a cardioplegia solution in order to offer an immobile and stable area for precise suturing. CPB itself is a traumatic procedure that may result in post-surgical complications, which are, among others, related to CPB duration. In recent years, alternative techniques have been developed to completely avoid CPB, by hand-suturing anastomoses on the beating, working heart using epicardial stabilizers (as described, for example in U.S. Pat. No. 5,836,311) that immobilize only a small area of the heart. However, practice has shown that the delicate procedure of hand-suturing the anastomosis may become even more difficult under such conditions, thus potentially having a negative impact on overall quality, even in experienced hands. Therefore, it is desirable to reduce the complexity and duration of the procedure by expediting the anastomosis procedure without reducing the quality or effectiveness of the anastomosis.

In order to reduce the difficulty of creating a vascular anastomosis during CABG, it is desirable to provide a rapid means for making a reliable anastomosis between a bypass graft, vein or artery and the native blood vessel. A first approach to expediting and improving the anastomosis procedure is through the use of stapling technology. However, the instruments for stapling other organs are not easily adaptable for use in creating a vascular anastomosis, and the small size of coronary arteries raises additional technical difficulties. Various attempts have been made to provide such vascular stapling devices, such as in U.S. Pat. Nos. 4,350,160 and 5,234,447. Other approaches to this problem are found in, for example, U.S. Pat. Nos. 4,366,819; 4,368,736; 4,624,257; 4,917,090 and 4,917,091.

More recently, specialized devices for creating a vascular anastomosis have been described in, for example, U.S. Pat. Nos. 5,695,504; 6,074,416; 5,931,842; 5,976,178; 6,066,148; 5,833,698; 5,707,380; 6,485,496 and U.S. Patent Publication No. US2002/0183769.

There remains a need for an anastomosis device which performs a suitable vascular anastomosis in a reliable manner and as quickly as possible

SUMMARY OF THE INVENTION

The present invention provides an anastomosis system for quickly and reliably performing a vascular anastomosis. The anastomosis system includes an anastomosis connector and an applicator. The connector is a tubular or annular device that is adapted to be expanded and permanently deformed to provide the anastomosis. The applicator provides a special sequence of movements to cause expansion and deformation of the connector. The applicator includes an expander, an expandable outer tube and an expandable inner tube located at least partially within a lumen of the expandable outer tube. The applicator also includes a mechanism for causing movement of the expander to thereby expand the inner and outer tubes of the applicator. The system is useful in providing a vascular anastomosis between a vascular graft and a natural blood vessel in CABG surgery, but may be useful for other applications as well. The present invention also provides an anastomosis method for quickly and reliably performing a vascular anastomosis.

BRIEF DESCRIPTION OF THE DRAWINGS

FIG. 3 is a perspective view of one embodiment of a connector in accordance with the present invention.

FIG. 4 is a side view of the connector of FIG. 3.

FIG. 5 is an end view of the connector of FIG. 3.

FIG. 8A is a partial cross-sectional view of an applicator for deploying individual staples or clips to make an anastomotic connection.

FIG. 8B is a perspective view of the distal end of the outer tube of the applicator of FIG. 8A.

FIG. 8C is an end view of the outer tube of the applicator of FIG. 8A in a first position.

FIG. 8D is an end view of the outer tube of the applicator of FIG. 8A in a second, expanded position.

FIG. 14 is an end view of the proximal end of the inner tube of the applicator of FIG. 6.

FIG. 15 is a cross-sectional view of the inner tube taken along the line XV-XV of FIG. 14.

FIG. 16 is a detail view of the area XVI shown in FIG. 15.

FIG. 17 is an end view of the distal end of the inner tube of FIG. 15.

FIG. 19 is a perspective view of an expander in accordance with the present invention.

FIG. 20 is a perspective view of the distal portion of the expander rod or tube of one embodiment of the present invention with the expander head removed.

FIG. 21 is a perspective view of the distal portion of the expander rod or tube of FIG. 20 including the expander head attached to the expander rod or tube.

FIG. 22 is a perspective view of the distal portion of the expander rod or tube of FIG. 21 further including the shoe attached to the expander head.

FIG. 23 is a perspective view of the distal end of the expander showing an alternative embodiment for attaching the shoe to the device.

FIG. 24 is a perspective view of the distal end of the expander showing an alternative embodiment of the expander head.

FIG. 25 is a perspective view of the distal end of the expander showing an alternative embodiment of the expander tube.

FIG. 26A is a cross sectional view of another embodiment of an expander in accordance with the invention.

FIG. 27A is a perspective view of another embodiment of an expander in accordance with the present invention.

FIG. 27B is a perspective view of the device of FIG. 27A with the shoe removed.

FIG. 27C is a side view of the expander of FIGS. 27A-27B.

FIG. 27D is a cross-sectional view of the expander of FIGS. 27A-27C.

FIG. 28A is a perspective view of an alternative embodiment of an expander in accordance with the present invention.

FIG. 28B is another perspective view of the expander of FIG. 28A.

FIG. 28C is a cross-sectional view of the expander of FIGS. 28A-28B.

FIGS. 33A-33C are partial cutaway views showing the movements of the applicator of FIG. 31.

FIG. 34 is a perspective view of the cam of the applicator of FIG. 31.

FIG. 35 is a side view of the left face of the cam of FIG. 34.

FIG. 36 is a cross sectional view of the cam of FIG. 35 along the line XXXVI-XXXVI of FIG. 35.

FIG. 37 is a side view of the right face of the cam of FIG. 34.

FIGS. 39A-39C are three cutaway views showing the movements of an actuator pulled by a cable in accordance with the present invention.

FIGS. 40A-40C are three cutaway views showing the movements of a dual-spring actuator which uses a cam and a pull cable in accordance with the present invention.

FIGS. 51A-51D are four cutaway views showing the movements of another embodiment of a cable-pulling actuator in accordance with the present invention.

FIG. 54 is a close up view of the area LIV of FIG. 53.

FIG. 64A shows a side view of the applicator with a shoe device and the graft vessel in a first position.

FIG. 64B shows a side view of the applicator with a shoe device and the graft vessel in a second position.

FIG. 64C shows a side view of the applicator and a shoe device interacting with the target vessel in a third position.

FIG. 64D shows a side view of the applicator and the shoe device placed inside the target vessel in a fourth position.

FIG. 67A shows a side view of the applicator and wire insertion shoe device.

FIG. 67B shows an isometric view of the wire insertion shoe device.

FIG. 67C shows an isometric view of the wire insertion shoe device with locking mechanism.

FIG. 67D shows a side view of the applicator and wire insertion shoe device.

FIG. 68A shows a top view of the external anastomotic ring.

FIG. 68B, shows an isometric view of the external anastomotic ring to be attached around the anastomosis.

FIG. 68C, shows an isometric view of the external anastomotic ring in a locked position.

FIG. 68D, shows an isometric view of the partially open external anastomotic ring.

DETAILED DESCRIPTION OF THE PREFERRED EMBODIMENTS

Figure 2:
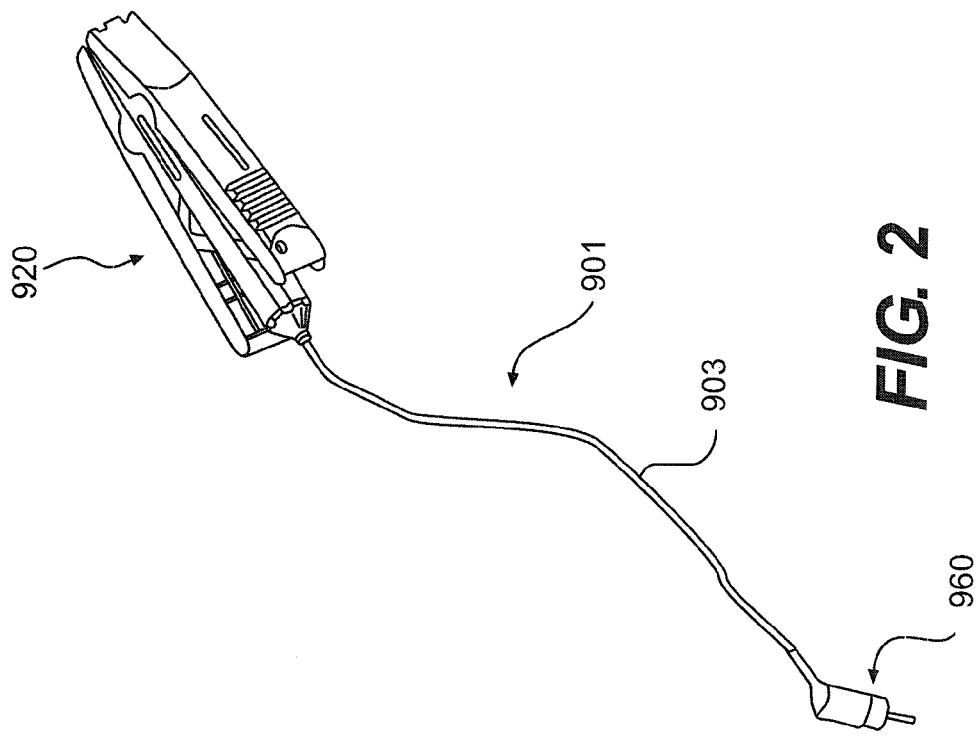
FIG. 2 is a perspective view of a remotely actuated applicator, which permits remote operation of the applicator.

The invention will now be described in detail with reference to the accompanying drawings. The detailed description describes the device in relation to a distal anastomosis during CABG surgery for joining the distal end of the bypass graft to the wall of a natural blood vessel. This example is given by way of illustration only and is not meant to limit the invention. Persons skilled in the art will recognize that the devices, system and methods of the present invention are readily adaptable for various types of anastomoses.

For the purpose of this description, the distal end of the applicator refers to the end that is designed for positioning at the location of the anastomosis site and the proximal end of the applicator refers to the end of the applicator designed for positioning away from the location of the anastomosis site. Similarly, the distal end of the expander refers to the end designed for positioning at the location of the anastomosis site and the proximal end of the expander refers to the end of the expander designed for positioning away from the location of the anastomosis site.

There are two general classes of anastomosis devices in accordance with the present invention. One class of anastomosis devices is the class of directly actuated device which is typically characterized by a short connection between the handle portion of the device and the front-end portion of the device. The front-end portion of the device is located distal to the handle portion of the device. The other class of anastomosis devices is the class of remotely actuated anastomosis devices that is typically characterized by a long, preferably flexible connection between the handle portion and the front-end portion of the device to allow remote actuation of the front-end portion using the handle portion.

Both classes of anastomosis devices are designed for use with a variety of different types of connectors. One type of connector is a deformable connector, such as those shown, for example, in U.S. Pat. No. 6,485,496, as well as U.S. patent application Ser. No. 09/708,617, and International Published Patent Application No. WO 02/38055, the disclosures of which are hereby incorporated by reference. Another type of connector with which the anastomosis devices of the present invention can be used is a hyperelastic or shape memory alloy connector such as is mentioned in U.S. Pat. No. 6,485,496, the disclosure of which is hereby incorporated by reference.

Combinations of deformable and hyperelastic or shape memory alloy connectors can also be employed. A fourth type of connector with which the anastomosis devices of the present invention can be used is a series of loose, separate staples, clips or the like which omit a connecting ring such as is present in the deformable connector mentioned above. Examples of the fourth type of connector can be found in U.S. Pat. No. 6,485,496 at col. 8, line 65 to col. 9, line 7, which is hereby incorporated by reference. A fifth type of connector includes staples connected to a bioabsorbable ring that is absorbed once the anastomosis is deployed. See U.S. Patent Publication No. 2003/0045902, which is hereby incorporated by reference. Additional embodiments of connectors for use with the anastomosis devices of the present invention are also described herein.

Figure 1:
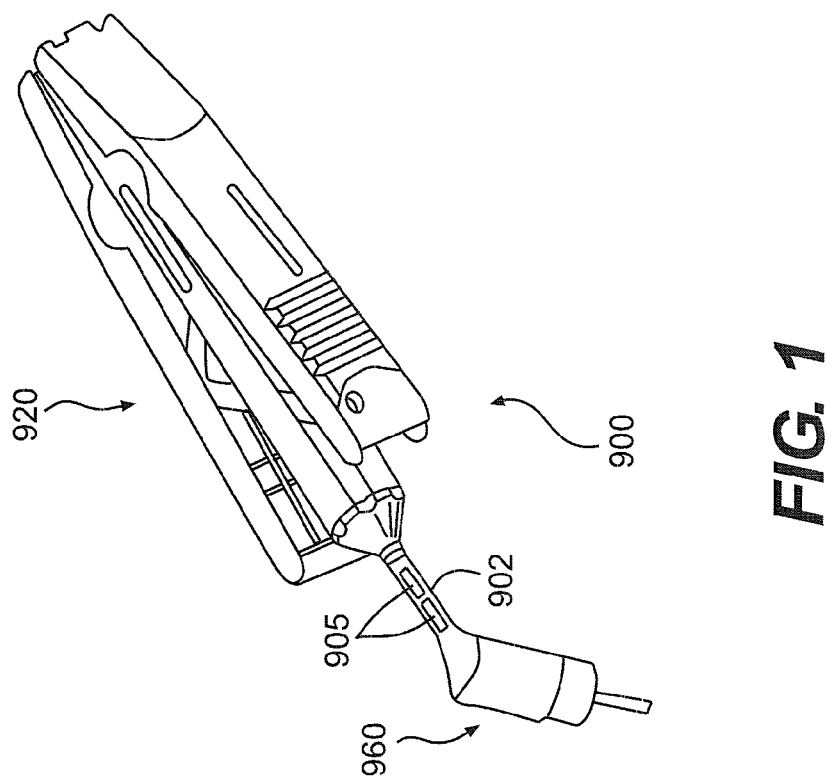
FIG. 1 is a perspective view of a directly actuated applicator.

FIG. 1 shows a perspective view of a directly actuated anastomosis device 900 in accordance with the present invention that includes a handle portion 920 and a front-end portion 960. Connection 902 is preferably formed by a rigid or semi-rigid connector which is rotatable relative to front-end portion 960 to allow positioning of handle portion 920 at different orientations relative to front-end portion 960. It is preferable that connection 902 not articulate, but connection 902 may articulate. The length of connection 902 can vary and it is possible, for example, to construct connection 902 from a plurality of tubular sections 905, as shown in FIG. 1 to permit customization of the length of connection 902 by constructing it from different numbers or lengths of tubular sections 905, as needed.

A remotely actuated anastomosis device 901 is shown in FIG. 2. The remotely actuated device 901 is typically characterized by handle portion 920 being connected to front-end portion 960 by a long, flexible connector 903, instead of by a short, rigid or semi-rigid connection 902 as in the directly actuated embodiment of FIG. 1. Flexible connector 903 has the advantage that due to its length and flexibility, front-end portion 960 can be operated remotely using the handle portion 920 to thereby permit an anastomosis to be done in difficult to reach locations, or via thoracoscopic or laparoscopic surgical methods, for example. Flexible connector 903 is also preferably connected to either or both of handle portion 920 and front-end portion 960 via an articulating connection to maximize the degrees of freedom of movement of the device 901 for positioning device 901 for an anastomosis and for handing off the device 901 from one person to another during an anastomosis procedure. Flexible connector 903 is preferably a minimally compressible sheath containing a cable, as shown in FIG. 2, which is releasably attached to one or both of handle portion 920 or front-end portion 960 to allow disassembly of device 901, as desired. Flexible connector 903 can be a ball-and-socket type shaft as described in U.S. patent application Ser. No. 09/492,558, filed on Jan. 27, 2000, or of the type described in U.S. patent application Ser. No. 10/736,199, filed on Dec. 15, 2003, the disclosures of which are hereby incorporated by reference.

Both the directly actuated device 900 and the remotely actuated device 901 include a front-end portion or applicator 960 that is capable of at least two distinct movements to accomplish an anastomosis. First, applicator 960 radially expands to cause radial expansion of the connector, and subsequently, the applicator 960 executes a second movement to compress and/or close the connector on the graft and target vessel. In preferred embodiments, applicator 960 returns to its starting position by uncompressing and unexpanding as third and fourth movements in the series of movements, to facilitate removal of applicator 960 from the anastomosis site.

A significant advantage of using the two separate motions to manipulate the connector is that it helps to ensure that the connector uniformly grasps all edges of the graft and target vessels. The first step of expansion serves to uniformly stretch the tissue and automatically centers a properly sized connector within the incisions or holes in both the graft and target vessels. The second step of compression and/or closure also automatically centers the tissue within the staples, clips or other grasping elements of the connector as a result of the action of the anvils of the applicator 960.

When a deformable connector is employed, a variety of different actuators can be employed to actuate the applicators and thereby deform the connector. Exemplary types of actuators for use with connectors made of a plastically deformable material like stainless steel, include dual-cam devices, dual-spring devices, single-cam, single-spring combination devices, and shape-memory-alloy devices.

Preferred types of actuators for use with resiliently deformable connectors, made of a hyperelastically deformable material like Nitinol, such as that described at col. 9, lines 14-21 of U.S. Pat. No. 6,485,496, include retaining or constraining devices. When a resilient, hyperelastic connector, is employed, it is preferable to constrain the annular or tubular body connecting the staple like members, separately from the staple or clip members. Once the connector is permitted to deform in the first step, by removing the constraint on the annular or tubular body of the connector, the staples or clips are subsequently released to complete the connection. In actuators for use with connectors made of a suitable shape memory alloy, the shape memory alloy connector can be heated to a specific temperature, e.g. warmed to body temperature, to cause the shape memory alloy to take a second shape to provide the needed motion to deform the connector, without the need of additional, external forces. In the case of a combination of a plastically deformable material and a resilient, hyperelastic material, the connector can be a combination of a nitinol body with staples or clips which are plastically deformable. To deploy this connector, the constraint on the body is removed to permit radial expansion and then axial motion of the applicator is applied to deform the staples. Such a connector creates an anastomosis that is compliant to pressure changes due to the resilience of the connector, thereby allowing it to pulsate more or less, like arterial vessels pulsate during their operation.

In an alternative combination of plastically deformable and resilient, hyperelastic materials, a balloon may be employed to expand the plastically deformable body of the connector. Subsequently, a constraint is removed to permit the resilient, hyperelastic staples or clips take their original shape and form the connection by clamping together the vessel walls.

The connectors in the various embodiments of the present invention can take several forms. The connector can include a ring with a plurality of staples, clips or the like attached thereto and be generally circular or can be generally oval. Polygonal shapes approaching a circle or oval are meant to be included in this description. Alternatively, the connector need not include a ring, in which case a plurality of loose or separate staples, clips or the like collectively form the connector. Connectors of this type are described, for example, at col. 8, line 65 to col. 9, line 7 of U.S. Pat. No. 6,485,496.

In the case of performing an oval anastomosis, a variety of different applicators can be employed. For example, a connector that is circular in its unexpanded state can be delivered by a circular applicator and activated by an oval expander. A connector that is oval in its unexpanded state can be delivered by an oval applicator. Alternatively, a circular applicator with an angled stapling plane and connector such as that described in FIGS. 14-15 of U.S. patent application Ser. No. 09/708,617 can be employed with a circular or oval expander.

A preferred feature of the various devices of the present invention is the keying of the fingers of the inner and outer tubes of the applicator to maintain alignment of the anvils at all times during the anastomosis procedure. This feature provides a more reliable, repeatable deployment of the connector. There are several variations on this feature which are described in detail herein. For example, in one embodiment, only the fingers of the inner tube of the applicator are keyed. Alternatively, only the fingers of the outer tube of the applicator are keyed. Finally, both the fingers of the inner tube and the fingers of the outer tube may be keyed to ensure alignment during the anastomosis procedure. Additionally or alternatively, the staple-like elements of connector 200 may be keyed to the fingers of the inner tube. Keying of the fingers of the inner and outer tubes to one another is particularly useful when actuating a circular applicator with an oval expander, for example.

The anastomosis devices of the present invention may be actuated by any of a variety of different energy sources including mechanical, hydraulic, electrical, pneumatic or other conventional or similar energy sources.

The anastomosis devices of the present invention are particularly suitable for internal side-to-side anastomosis procedures, though the devices can be used with a variety of other procedures as well, such as end-to-side anastomoses.

The internal side-to-side anastomosis procedures can be performed using semi-axial introduction or perpendicular introduction and certain device modifications may be desirable depending upon the type of introduction that will be employed. The type of introduction may be selected based on factors such as the location of the anastomosis and the ease with which the anastomosis site can be reached for a particular introduction method. These two different insertion methods can also be performed using a guide wire insertion technique wherein the anastomosis device may be guided to the anastomosis site by a guide wire.

Referring now to the drawings, where like elements are referred to by like reference numerals throughout the several views, various specific embodiments of the anastomosis devices and methods are described below for the purpose of illustrating the invention.

FIGS. 3-5 depict one embodiment of a deformable connector 200 in accordance with the present invention. Connector 200 includes a plurality of joining elements in the form of staple elements 202 spaced around the circumference of connector 200. A preferred connector 200 has eight staple elements 202, though connector 200 may have more or less staple elements 202, depending upon the size of the anastomosis. Connector 200 is preferably formed from a single piece of biocompatible material such as stainless steel or titanium. Alternatively, bioabsorbable materials like polyglactin (Vicryl®) or polydioxanone (PDS®) may be used, or a combination of a bioabsorbable material and nonabsorbable material, for example a bioabsorbable ring, holding stainless steel staples or clips. Additionally, connector 200 may be coated with substances comprising pharmaceuticals, such as agents that prevent or inhibit restenosis, enhance endothelial cell coverage, and/or decrease thrombus formation.

Connector 200, as shown in FIGS. 3-5, is formed from a continuous elongate element having a sinusoidal pattern, which pattern is preferably formed about a central ring 204 of connector 200. The sinusoidal pattern may be customized into a sinusoidal ring 205 made up of portions 206, 208. Staple elements 202 can be formed at each portion 208 of sinusoidal ring 205. The sinusoidal ring 205 of connector 200 provides the radial expandability of the connector 200 since the portions 206, 208 are capable of at least partial straightening, relative to the degree of curvature of the portions 206, 208 in the insertion position, to thereby lengthen the portions 206, 208 relative to the central ring 204 and permit radial expansion of connector 200. While ring 205 is described as sinusoidal, one skilled in the art will recognize that ring 205 can take any form so long as it is capable of being expanded from a first diameter to a second diameter. Connector 200 is fabricated for plastic deformation and thus will retain its final shape after expansion and will not revert to its initial shape.

Each staple element 202 is preferably formed from two staple portions 210, 212 which extend from a point of attachment of staple portions 210, 212 to connector 200 in substantially opposite directions, as shown in FIGS. 3-5. The length, thickness and inclination of staple portions 210, 212 can be varied to provide customized bending characteristics or thicknesses for staple portions 210, 212, if desired. Also, staple portions 210, 212 may form more complex shapes, for example a "Y-shape", so that each staple portion provides multiple extension that each engage the tissue. In a preferred embodiment, staple portions 210, 212 extend from opposite sides of portions 208.

As shown in FIGS. 3-5, connector 200 is in the insertion position, the position in which it is delivered to the anastomosis site. Preferably, the staple portions 210, 212 of this embodiment are slightly tapered on their outer side towards their distal free ends in one or both of radial thickness and circumferential width. That is, the diameter of a circle drawn connecting the outer surfaces of base 210a, 212a of staple portions 210, 212 is greater than the diameter of a circle drawn connecting the outer surfaces of tips 210b, 212b of staple portions 210, 212. The outer sides 211, 213 of staple portions 210, 212 are inclined relative to a radial plane through the center of staple portions 210, 212 such that the width $W_1$ of staple element 202 is smaller on the radially inner side than the width $W_2$ of staple element 202 on the radially outer side.

Preferably, the distal tips of staple portions 210, 212 may be formed into a curve (not shown) which anticipates the curvature of the distal tips of staple portions 210, 212 when connector 200 is formed into the connection position. This may increase the consistency and predictability with which staple portions 210, 212 deform during the anastomosis procedure. Portions 206 of the sinusoidal pattern may also be slightly tapered to a lesser thickness in the axial direction (not shown) to correspond to the taper of the adjacent staple portions 210, 212, if desired.

Deformable connectors, such as that depicted in FIGS. 3-5, can be delivered to the anastomosis site by a variety of different delivery devices, including both directly actuated and remotely actuated delivery devices. The various delivery devices will include an applicator and an expander for expanding the applicator. Several embodiments of applicators and expanders suitable for delivery of deformable connectors are described below.

Figure 6:
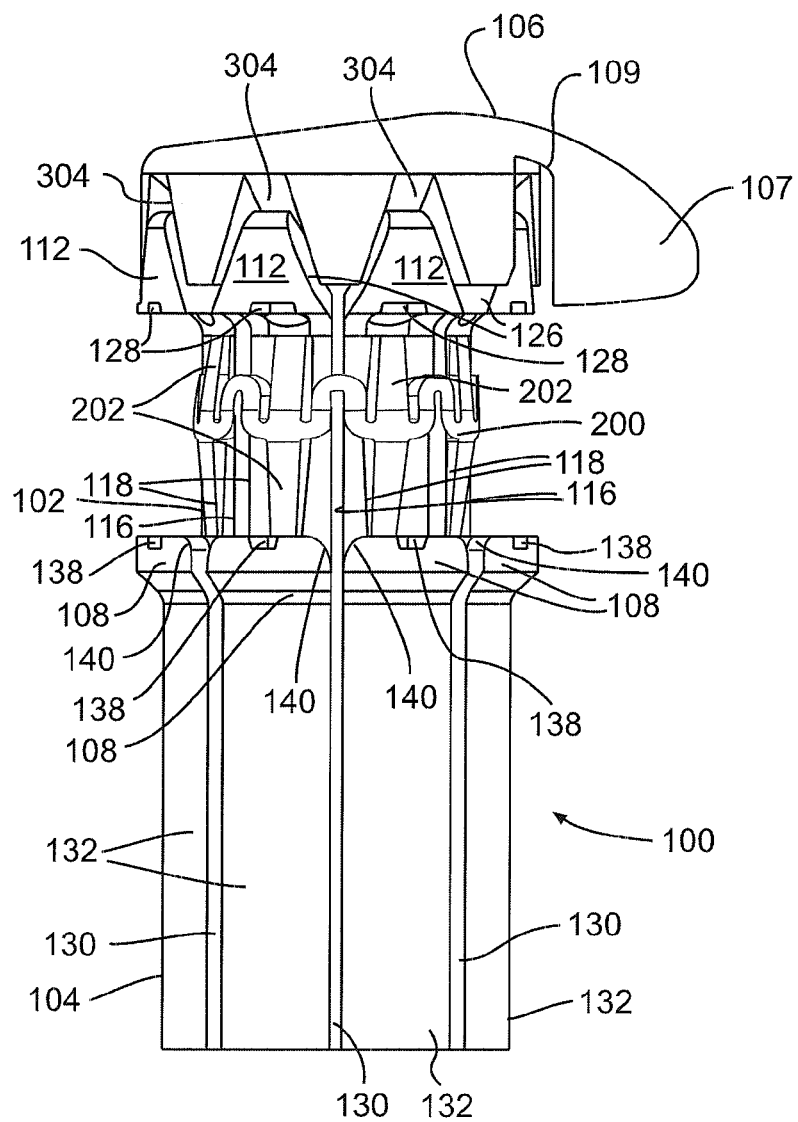
FIG. 6 is a perspective view of the distal end of an applicator in accordance with the present invention, in the insertion position.

FIG. 6 is a perspective view of an applicator 100 for use in an anastomosis system in accordance with the present invention, shown in the insertion position. Applicator 100 includes an inner tube 102, an outer tube 104 and a distal attachment such as a shoe 106. As shown in FIG. 6, applicator 100 is in the insertion position in which the applicator 100 is delivered to the anastomosis site. In use, a deformable connector 200, such as that described in FIGS. 3-5, is associated with the applicator 100 for delivery to the anastomosis site with the applicator 100. The inner tube 102 is designed to accommodate an expansion device 300 (described below), which, when actuated, causes expansion of the applicator 100 from the insertion position shown in FIG. 6 to the expanded position shown in FIG. 7.

As shown generally in FIGS. 6-7 and 14-17, and more particularly in FIG. 15, to permit expansion of the connector 200, when positioned on the inner tube 102, inner tube 102 has a plurality of slits 116 extending from the distal end of inner tube 102 in a proximal direction (toward the proximal end of inner tube 102) for a sufficient distance to permit the desired degree of expandability of inner tube 102 by expansion device 300. Specifically, the length of the slits 116 is sufficient to permit sufficient radial deflection of the fingers 118 of the inner tube 102 located between each of the slits 116 to provide the desired degree of expansion of the inner tube 102 and thus the desired degree of expansion of the connector 200. For example, the length of the slits 116 may be from 2-10 times the diameter of the inner tube 102, but most preferably approximately five times the diameter of the inner tube 102.

As is shown in FIG. 16, at least a portion of the lumen 120 of the inner tube 102 is preferably tapered from a greater diameter at the distal end of the inner tube 102 to a lesser diameter in the direction of the proximal end of the inner tube 102. Tapered surfaces 122 of fingers 118 of inner tube 102 are detailed in FIG. 15. The angle of the taper relative to the distal end of inner tube 102 is preferably from about 30° to about 45°. The tapered surfaces 122 are adapted to interact with corresponding surfaces 304 of expansion head 302 of expansion device 300 (described below) in a manner whereby retraction of the expansion device 300 in the proximal direction, relative to inner tube 102, urges fingers 118 of inner tube 102 radially outward to cause expansion of inner tube 102 and thus connector 200.

Inner tube 102 is also provided with a plurality of anvils 112 each of which is located on the distal end of one of fingers 118 of inner tube 102. Anvils 112 may serve three different functions in the operation of applicator 100. First, anvils 112 are provided with tapered surfaces 122 as described above to cause expansion of fingers 118 of inner tube 102 when corresponding surfaces 304 of expansion head 302 are drawn proximally relative to inner tube 102. Second, anvils 112 include a series of angled surfaces 126 on the sides of anvils 112 that are designed to mate with the corresponding angled surfaces 306 of expansion head 302 to ensure that when fingers 118 of inner tube 102 move radially outward that the spacing between fingers 118 remains substantially uniform to thereby provide substantially uniform expansion of inner tube 102. A third function of anvils 112 is to provide surfaces 114 that interact with corresponding surfaces 110 of anvils 108 of the outer tube 104. Surfaces 110, 114 may optionally be curved. Each pair of anvils 108, 112 is designed to interact with staple elements 202 of connector 200 shown in FIG. 3 to bend the staple elements 202 of connector 200 into the position that creates the anastomosis. Preferably, the applicator 100 includes eight anvils 108, eight anvils 112 and eight staple elements 202 of the connector 200. The number of anvils and staple elements may vary depending on the size of the anastomosis. For example, for smaller vessels, connector 200 may have seven or less staple elements 202, or for larger vessels, connector 200 may have nine or more staple elements 202. In each case, applicator 100 preferably would include a number of anvils 108, 112 that correspond to the number of staple elements 202.

Figure 7:
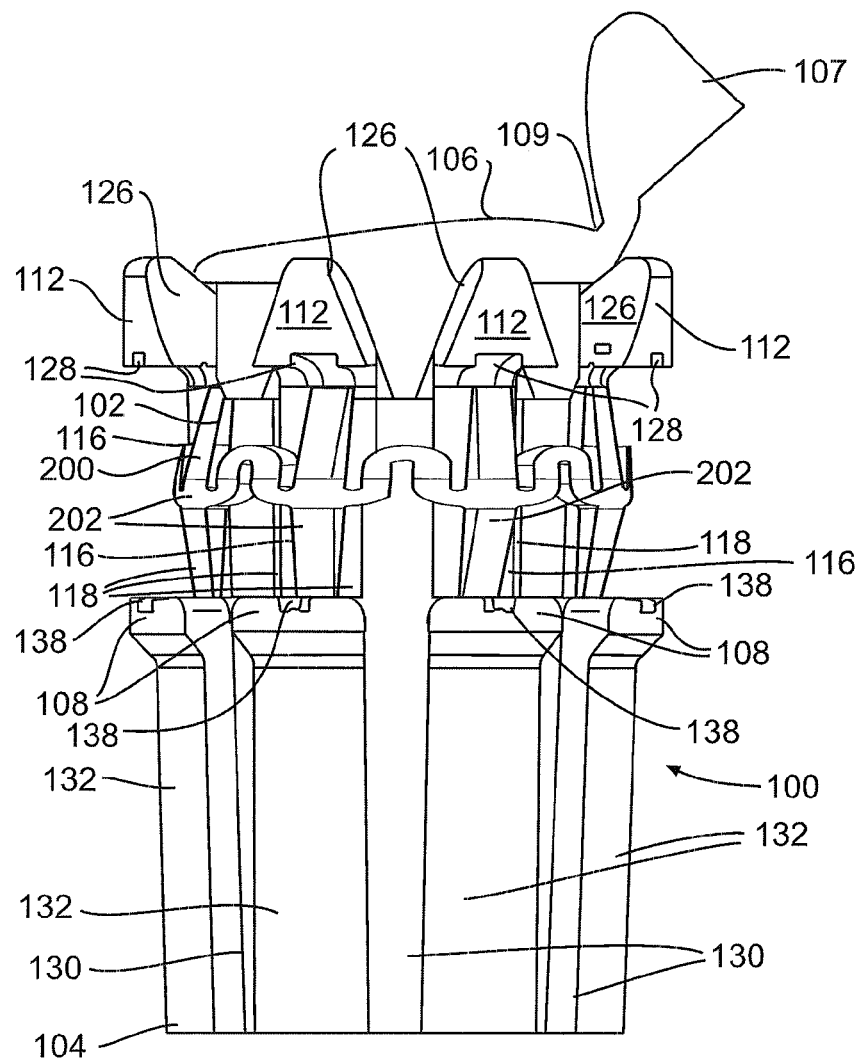
FIG. 7 is a perspective view of the distal end of the applicator of FIG. 6 in an expanded position.
Figure 9:
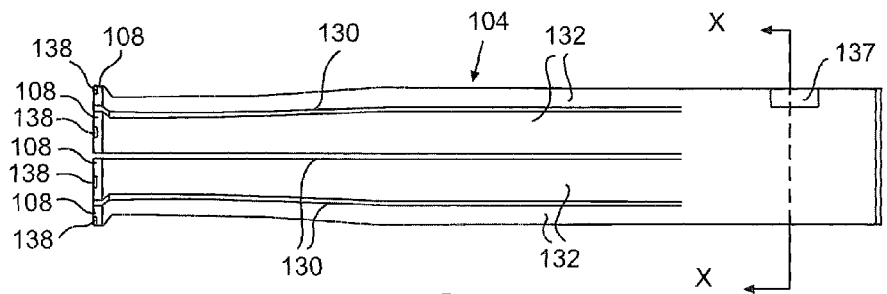
FIG. 9 is a perspective view of the outer tube of the applicator of FIG. 6.
Figure 10:
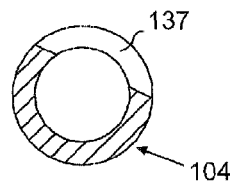
FIG. 10 is a cross-sectional view of the outer tube taken along the line X-X of FIG. 9.
Figure 11:
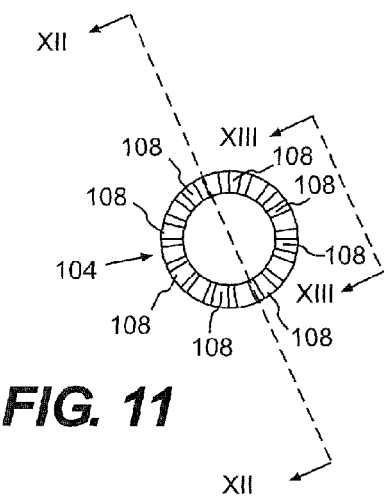
FIG. 11 is an end view of the outer tube of FIG. 9.
Figure 13:
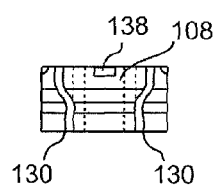
FIG. 13 is a detailed end view of the outer tube of FIG. 9.

The outer tube 104, as shown generally in FIGS. 6-7 and 9-13, and more particularly in FIG. 9, also has a plurality of slits 130 that form a plurality of fingers 132. Upon expansion of inner tube 102, outer tube 104 also expands by virtue of slits 130 in outer tube 104 as shown in FIG. 7.

In one embodiment, outer tube 104 is capable of movement in an axial direction relative to inner tube 102 to permit the distal ends of inner and outer tubes 102, 104 to move together in the second step of the performance of an anastomosis: to compress and/or close the connector on the graft and target vessel. The movement of the distal ends of inner and outer tubes 102, 104 together bends staple elements 202 of connector 200 from an insertion position to a connection position whereby the anastomosis is formed. To obtain optimal, blood tight sealing of the generally elastic vessel walls, the staple elements 202 are often required to deform to a shape having a diameter less than the combined thickness of these walls. This requires the anvils to come closer to each other than this combined thickness, resulting in tissue compression, which can lead to some damage. It is advantageous to keep this compressed area as small as possible to limit any potential damage, by reducing the front area of at least one of the paired anvils 108, 112 facing each other. As shown in FIG. 6, anvils 108 therefore have their tips rounded in the axial direction.

Figure 18B:
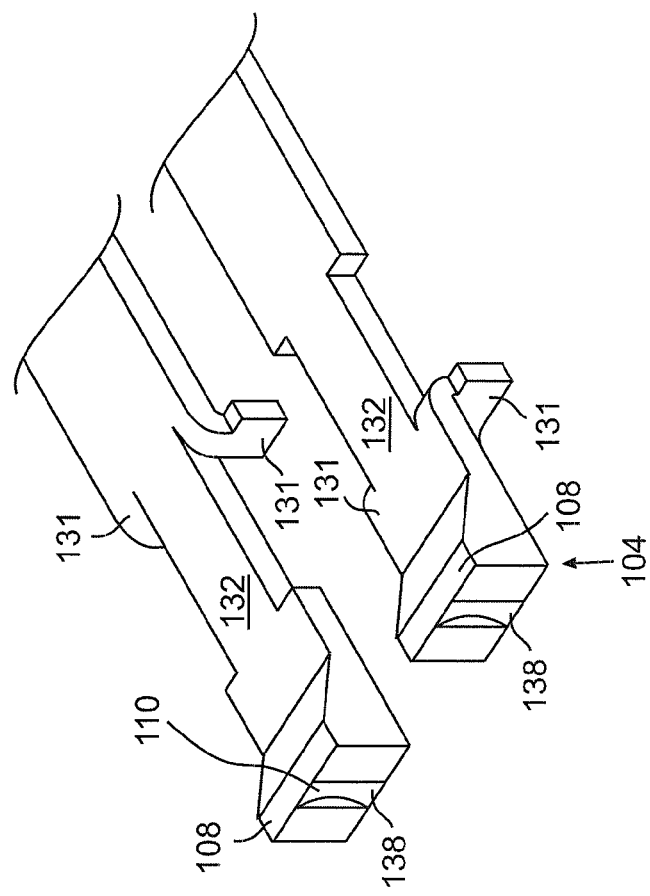
FIG. 18B shows a perspective view of two fingers of the outer tube with a keying mechanism formed by the slits of FIG. 18A.

Referring to FIGS. 6 and 9, to better hold connector 200 in position on applicator 100 during insertion and expansion, anvils 112 of inner tube 102 may include slots 128 sized to accept a portion of staple elements 202 of connector 200. Corresponding slots 138 sized to accept a portion of staple elements 202, may also be found in anvils 108 of outer tube 104. In a preferred embodiment, one set of tips 210b or tips 212b is disposed within slots 128 of inner tube 102 and the other set of tips 210b or tips 212b is disposed within slots 138 of outer tube 104. As shown in FIG. 18b, slots 128, 138 may be shallower than shown in FIG. 6 or 13, and may have a more scalloped appearance so as not to require the notching of material from anvils 108, 112 across their entire thickness. Surfaces 110 of inner tube 102 and surfaces 114 of outer tube 104 form the inner boundary of slots 128, 138, respectively.

Slots 128, 138 hold connector 200 in position during insertion and expansion by virtue of the application of slight, static pressure to the ends of staple elements 202 by the inner and outer tubes 102, 104, thus securely engaging connector 200, especially when the tips 210b, 212b of staple elements 202 are pre-bent to fit into curved surfaces 110, 114. Alternatively, the distance between the anvil faces is defined as sufficiently less than the length of the preformed staple legs, such that when one end of connector 200 is disposed at the extreme depth of one of curved surfaces 110, 114, the other end of connector 200 would extend beyond the opposing anvil face, i.e. rests partially in the other one of curved surfaces 110, 114. In either case, the penetrating tips 210b, 212b of staple elements 202 are substantially shielded within slots 128, 138, until the staple elements 202 are deformed to their final joining position. In this way, tips 210b, 212b are prevented from prematurely engaging any tissue during the manipulation of applicator 100 required to insert the distal end of applicator 100 into the graft and target vessels. This type of configuration can also hold separate staple elements 202 formed of staple portions 210, 212, when these are not connected by the sinusoidal ring formed by portions 206, 208. The pressure on the tips 210b, 212b of staple elements 202 can be increased by moving outer tube 104 axially in the distal direction relative to inner tube 102 to deform the staple-like elements to their joining position. The compression step preferably occurs after the step of expanding connector 200.

Following the compression step, to remove applicator 100 and leave connector 200 in position, outer tube 104 is moved axially in a proximal direction relative to inner tube 102 to release the pressure on connector 200, and thereby permit connector 200 to disengage from slots 128, 138 of inner and outer tubes 102, 104.

In a more preferred embodiment of the invention, outer tube 104 is maintained in a fixed position throughout the anastomosis procedure. In this embodiment, inner tube 102 is moved in an axial direction towards the distal end of outer tube 104 during the anastomosis procedure to cause deformation of staple elements 202 of connector 200. Once the anastomosis is created, inner tube 102 can return to its original position by movement in an axial direction away from the distal end of outer tube 104. This embodiment is preferred since it reduces the number of moving parts required to effect the required motion. Alternatively, the invention also contemplates moving both inner tube 102 and outer tube 104 relative to one another.

Figure 12:
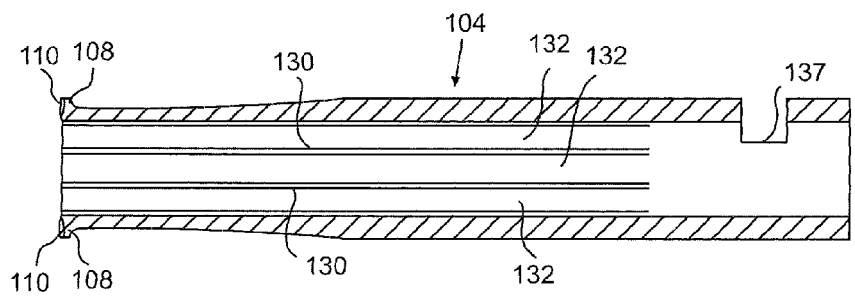
FIG. 12 is a cross-sectional view of the outer tube of FIGS. 9-11 taken along the line XII-XII of FIG. 11.

Referring to FIGS. 12 and 15, to maintain alignment between inner and outer tubes 102, 104 during use of applicator 100, inner tube 102 has a key 127 in the proximal end thereof that mates with a key 137 formed in outer tube 104. Keys 127, 137 help to maintain axial alignment between curved surfaces 110, 114 of the inner and outer tubes 102, 104 and ensure uniform expansion of applicator 100 and connector 200 as outer and inner tubes 102, 104 expand under the force of expander 300.

Figure 18A:
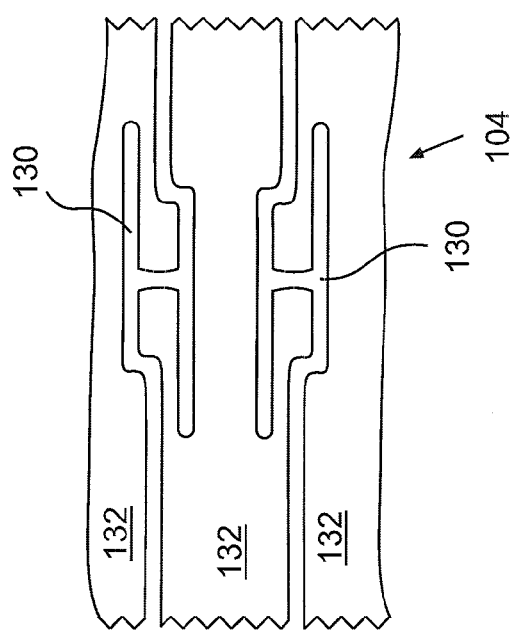
FIG. 18A shows a special pattern for the slits between the fingers of the outer tube to provide a keying mechanism.

An alternate keying mechanism is depicted in FIGS. 18A and 18B. FIG. 18A depicts three adjacent fingers 132 of outer tube 104 that have a special pattern for slits 130 in outer tube 104 which can be used to create a keying mechanism for keying fingers 132 of outer tube 104 with fingers 118 of inner tube 102. The special pattern of slits 130 shown in FIG. 18A provides small protrusions 131 that can be bent to extend inwardly from fingers 132 of outer tube 104 as shown in FIG. 18B to a position that locks around fingers 118 of inner tube 102. As with the embodiment described in connection with FIGS. 12 and 15, such a mechanism maintains alignment of fingers 132 of outer tube 104 with fingers 118 of inner tube 102 during use of applicator 100. In this embodiment, the position of protrusions 131 alternates with each finger 132 as shown in FIG. 18B.

One advantage of the provision of a keying mechanism that maintains alignment between the fingers 118, 132 of the inner and outer tubes 102, 104 is that keyed expander head 302, described below, can be greatly simplified as it is no longer needed to assist with ensuring this alignment. It is still required, as one function of expander head 302 is to ensure substantially uniform expansion of the inner and outer tubes 102, 104. The keying mechanism substitutes in part for keyed expander head 302 by performing this function of maintaining alignment between the fingers 118, 132 of the inner and outer tubes 102, 104 and in turn the curved surfaces 110, 114 of the inner and outer tubes 102, 104.

Figure 18D:
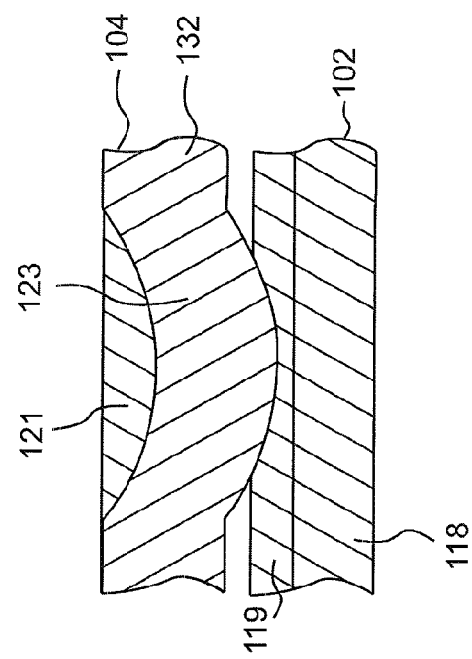
FIG. 18D is a cross-sectional view of portions of the inner and outer tubes of FIG. 18C showing the inner and outer tubes keyed together by the keying mechanism.
Figure 18C:
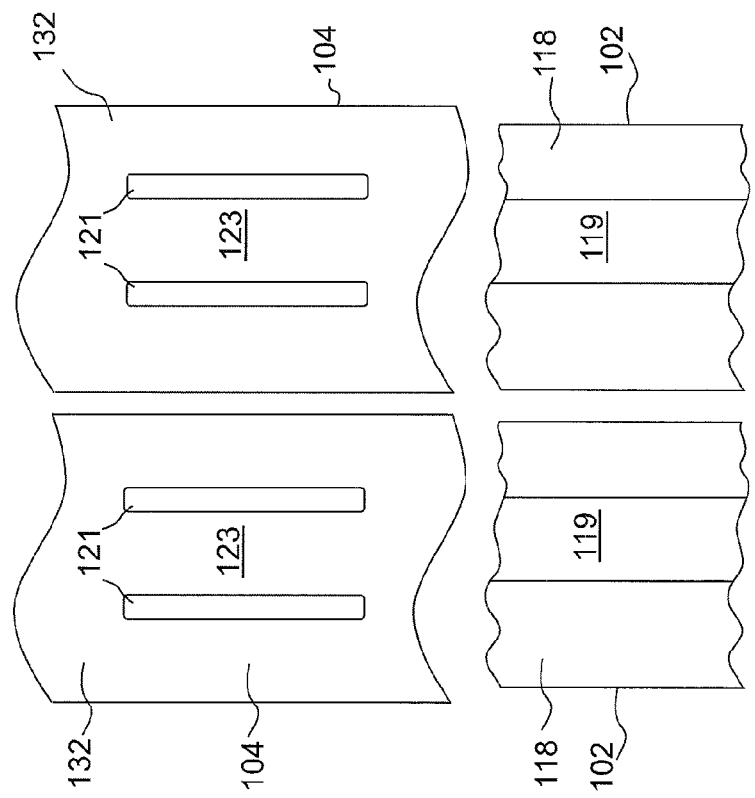
FIG. 18C shows a top view of portions of the inner and outer tubes formed with an alternative embodiment of a keying mechanism.

Another keying mechanism is depicted in FIGS. 18C-18D. In FIG. 18C, each finger 118 of inner tube 102 includes a longitudinal groove 119 therein. Each finger 132 of outer tube 104 is provided with longitudinal slots 121 to create an area 123 located between longitudinal slots 121 that can be deformed downwardly to the position shown in FIG. 18D. Outer tube 104 may include a single pair of longitudinal slots 121, or, more preferably, each finger 132 of outer tube 104 may have one or more longitudinal slots 121 spaced from one another in an axial or longitudinal direction. To key each finger 132 of outer tube 104 to each finger 118 of inner tube 102, areas 123 of finger 132 of outer tube 104 are deformed downwardly in the direction of inner tube 102, as shown, for example, in FIG. 18D such that area 123 is at least partially disposed within longitudinal groove 119 of finger 118 of inner tube 102. Preferably, each longitudinal groove 119 is substantially centered in finger 118 of inner tube 102. Alternatively, outer tube 104 can be made from a special type of tube, having longitudinal protrusions on its inner surface, regularly spaced inside its inner circumference. Such a special tube can for example be made by the process of extrusion, which is commonly used for the production of all kinds of tubes. If properly dimensioned, this results in an outer tube 104, having fingers 132, each having one or more longitudinal protrusions extending inwardly, which can key with one or more appropriately placed grooves on the outside of inner fingers 118. These matching grooves on inner fingers 118 of inner tube 102 can be obtained by making tube 102 also from an extruded profile, having a grooved outer shape matching the inner shape of outer tube 104. Additionally or alternatively, connector 200 can be keyed to inner fingers 118. This can for example be done by providing longitudinal grooves 119 in inner fingers 118 and pre-bending staple-like elements 202 of connector 200 slightly towards the central axis of connector 200 to a diameter less than the diameter of the ring 205. Connector 200 is positioned on inner fingers 118 such, that staple-like elements 202 are at least partially disposed within longitudinal grooves 119, while the extreme tips are pre-bent outwards more markedly so these tips still fit in curved surfaces 110, 114 of anvils 108, 112. Alternatively, connector 200 can be manufactured from an extruded tube having longitudinal protrusions on its inner surface as described above, so that each staple-like element 202 has longitudinal protrusions extending inwardly, fitting in grooves 119 of inner fingers 118.

Again, use of the keying mechanism of FIGS. 18C-18D permits operation of the device without the need for keyed expander head 302. Instead, a simple, smooth cone can be used to expand inner and outer tubes 102, 104, since the keying mechanism maintains proper alignment of inner and outer tubes 102, 104 during operation of applicator 100.

During successful deployment of connector 200, connector 200 undergoes two distinct motions: radial expansion of ring 205, and axial compression of staple elements 208, 210. The required sequential motions can be achieved with dual-cam, single-cam/single-spring, or dual-spring drive mechanisms, or, in the alternative, by using shape memory or hyperelastic alloys. In addition, those skilled in the art can use the teachings provided herein to devise other types of drive mechanisms to achieve the same output motion.

Referring now to FIGS. 19-26, there is shown one embodiment of an expander 300 in accordance with the present invention. Expander 300 is formed from a combination of an expander head 302 and an expander rod or tube 312. Expander head 302 is preferably made from a hard material capable of expanding inner and outer tubes 102, 104 under the load required to expand connector 200. Expander rod or tube 312 may be a solid rod or a hollow tube (as shown in FIG. 20) and may be provided at the distal end of expander rod or tube 312 with an angled flare, as shown in FIG. 25, or a flange 314, as shown in FIG. 20. The proximal end of expander rod or tube 312 can be attached to an actuation device, for example, by an external threaded connection 316 as shown in FIG. 19, or by an internal thread and a threaded screw 338 as shown in FIG. 26. Any other type of connection known to those skilled in the art may be used to connect the proximal end of rod or tube 312 and the actuation device.

Preferably, expander rod or tube 312 is insert-molded to expander head 302 to provide a reliable connection between expander rod or tube 312 and expander head 302 and prevent expander head 302 from disengaging from expander rod or tube 312 during use of applicator 100. For this purpose, flange 314 provides structure for mating with a corresponding structure of expander head 302 to provide a mechanical bond between expander rod or tube 312 and expander head 302. In a preferred embodiment, the surface of flange 314 is defined to maximize the bonding force.

In the embodiment shown in FIGS. 19-22, expander 300 includes an expander head 302 that has an opening 302a that communicates with a passageway 318 located in the distal end of expander tube 312 (FIG. 20). Passageway 318 and opening 302a together allow materials, such as drugs, genes or cells, or devices, such as fiber optic bundles or guide wires to be passed through the expander tube 312 for the purpose of either guiding applicator 100 to and/or from the anastomosis site, or introducing, for example, drugs designed to reduce or prevent scar tissue formation at the anastomosis site. Pharmaceuticals for preventing or inhibiting restenosis or to enhance endothelial cell coverage could be delivered through passageway 312. Exemplary drugs include, but are not limited to, anti-platelet agents, anti-coagulants, calcium-channel antagonists, ACE inhibitors, nitric oxide, anti-inflammatory agents, growth factor inhibitors, antioxidants and antibiotics. The pharmaceuticals could be delivered in solution or as a viscous gel. Other treatments such as autologous endothelial or stem cells, with or without genetic modification, and genetic vectors could be delivered in this manner as well. Preferably, passageway 318 is a bore that runs the length of tube 312, but passageway 318 may also communicate with a separate lumen or lumens that run within or outside tube 312.

Figure 8E:
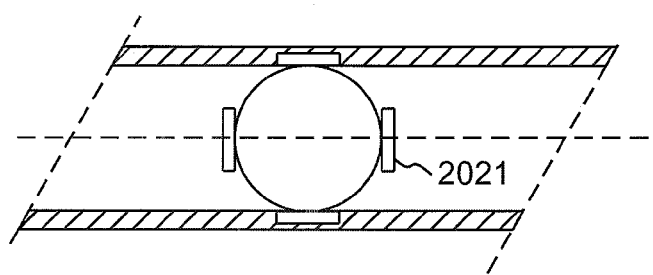
FIGS. 8E and 8F are top and side cross-sectional views of the staples or clips of FIG. 8A deployed at the location of an anastomosis.
Figure 8F:
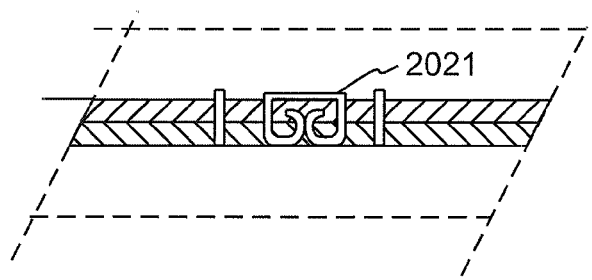

Referring to FIGS. 8A-8F, an alternative embodiment of applicator 100 is depicted, wherein outer tube 104 is divided into a distal portion 1041 and a proximal portion 1042 that move axially relative to each other. Distal portion 1041 has recesses 1045 and proximal portion 1042 has pushing mechanisms 1046 (which can be, e.g., rods, plates or cylinders) that are sized to be at least partially disposed within recesses 1045. This design is especially suitable for delivery of separate staple elements, like U-shaped clips 2021, that can be disposed, as shown in FIG. 8A, within recesses 1045 at a location distal to pushing mechanisms 1046.

In such an embodiment, outer tube 104 can be formed as a radially expandable cartridge that expands from a first position, shown in FIG. 8C, to a second position, shown in FIG. 8D. Outer tube 104 can include outer portions 1041b connected by web portions 1041c. Recesses 1045 are preferably located in outer portions 1041b. In a preferred embodiment, outer tube 104 includes four outer portions 1041b, each of which house a separate clip or staple 2021 in its respective recess 1045.

Referring to FIG. 8C, in the starting position, adjacent outer portions 1041b are located relatively close together, such that web portions 1041c fold to form slits 1041. Pushing mechanisms 1046 of proximal portion 1042 are positioned within recesses 1045.

After the inner tube 102 and outer tube 104 have been expanded to center the applicator within the holes of the target and graft vessel, outer tube 104 is moved in an axial direction towards anvils 112 of inner tube 102. Distal portion 1041 of outer tube 104 retains both clips 2021 and pushing mechanisms 1046 such that as outer tube 104 is moved in axial direction, the target and graft tissue is compressed between anvils 112 and distal portion 1041. Once the tissue has been compressed, distal portion 1041 can no longer move, and pushing mechanisms 1046 push clips 2021 out of distal portion 1041 until clips 2021 penetrate the tissue and are subsequently deformed to a joining position by distal anvils 112. As with prior embodiments, anvils 112 may be shaped to suit the specific type of staple or clip 2021.

Alternatively, distal portion 1041 may extend concentrically about portion 1042. This design allows distal portion 1041 to be moved independently, so that it can be used to first clamp the tissue against the distal anvils 112. This offers the additional advantage of allowing visual inspection of the position of the tissue, before actually deploying the staples or clips 2021. FIGS. 8D and 8E show top and side cross-sectional views of clips 2021 in a preferred joining position spaced at four positions about the anastomosis holding the vessel walls.

In still another embodiment (not shown), pushing mechanism 1046 may be hollow rods, similar to needles that are disposed within recesses 1045 and are long enough to axially traverse recesses 1045 and penetrate the tissue. The lumen of the needles may be connected to a central reservoir, which can be pressurized. The lumen of the needles may contain any joining means to connect tissue, such as self-expanding Nitinol staples, or, more preferably, biocompatible glue. Pressurizing the lumen of the needles may push out the joining means. In case of glue, the device could work as follows: applicator 100 is expanded inside the holes in the walls of the vessels to be joined. Distal and proximal portions 1041 and 1042 are pushed distally towards anvils 112, so that both walls are clamped and substantially penetrated by the needles. Subsequently, distal portion 1041 is maintained stationary relative to the anastomosis site to keep the tissue clamped, and proximal portion 1042 is pulled proximally, to retract the needles out of the tissue while pressurizing the lumen of the needles to push glue out of the end of each needle. In this way, glue fills the hole made by each needle as the needles are withdrawn from the tissue, thereby forming plugs of glue inside the tissue, joining the tissue. Additional glue may be applied from outside the anastomosis, and an external protective ring 1100 may be used, if desired. The internal clamping of the tissue with applicator 100 can be released when the glue has hardened to a sufficient strength.

It is also possible to connect the tissue with glue applied from the outside only. In this case, applicator 100 resembles the embodiment shown in FIGS. 6 and 7, however, it does not need to carry connector 200, and therefore does not require recesses 114 and 138. Applicator 100 is instead used to clamp the vessel walls together from the inside, preferably by first expanding applicator 100, and subsequently clamping the tissue together by axially moving outer tube 104 towards anvils 112 of inner tube 102, but other sequences may be used as well, depending on the situation. Glue can then be applied externally, on the external surface of the anastomotic line.

Biocompatible glue may be used in combination with any type of connector 200, to reinforce or seal the mechanical bond, provided by the deformed staple like elements of connector 200. Glue is preferably applied from the outside of the anastomosis. This can be done before making the arteriotomies in both vessels to be joined, thus first gluing together two vessel walls, and subsequently making an arteriotomy through both walls and deploying applicator 100 and connector 200, thereby mechanically reinforcing the glued tissue bond. Glue can also be applied during the construction of the anastomosis, for example by providing glue on the outside of the adjoining vessel walls after expansion of connector 200, before or after closure of staple-like elements 202. Finally, glue can be applied on the outside of the adjoining vessel walls after completion of the anastomosis and removal of applicator 100.

It is thus understood, that throughout this specification, and especially where deployment methods are described in detail, reference to joining the tissue with connector 200 is explicitly meant to include use of separate staples, or a unitary connector, or glue, or any other suitable or conventional means.

To facilitate the insertion of applicator 100 into the holes in the walls of the vessels to be joined, and in particular the insertion of the distal anvils 112 into the target vessel, using one of the insertion methods described later in this document, expander head 302 can be equipped with a nose cone. The nose cone can have a more or less conical, streamlined shape in an axial direction relative to the central axis of the applicator, for example as shown previously in FIG. 20 of U.S. patent application Ser. No. 09/708,617, or it can have a more or less conical, streamlined protrusion extending in a radial direction relative to the central axis of the applicator, thus taking the shape of an insertion shoe 106, as shown in, for example, FIGS. 6, 22, 23, 27, and 28A, or any angle in between.

Shoe 106 must be retrievable through the deployed, expanded ring 205 of connector 200, to allow removal of applicator 100 after completion of the anastomosis. If the contour of shoe 106, in a plane perpendicular to the central axis of the applicator, has a greatest length less than the diameter of the expanded connector 200, the shoe can be attached to expander head 302 in a fixed, non-moving way. If the length of shoe 106 exceeds the diameter of expanded connector ring 205, shoe 106 must be able to decrease its dimensions in this plane by being retractable, pivotable, movable, deformable, deflatable or any combination of these, or must be able to decrease its dimensions in this plane by some other means known to those skilled in the art. Alternatively, shoe 106 can be detachable, initially held by mechanical means or magnetic force, and retrieved separately from the applicator, thus offering additional degrees of freedom for optimal manipulation, for example by extraction through an alternative route like the native, target vessel.

The nose-cone must also fit within the lumen of the vessels to be joined, in particular the target vessel, which is generally the smaller vessel, before and after the device is brought into a delivery position, substantially perpendicular to the target vessel, as described later on. Therefore, if the contour of the nose-cone has a greatest length in a plane parallel to the central axis of the applicator, that exceeds the diameter of the target vessel, the nose cone has to be able to decrease its dimensions in this plane by being retractable, pivotable, movable, deformable, deflatable or a combination of these, or must be able to decrease its dimensions in this plane by some other means known to those skilled in the art. Alternatively, it can be detachable as described above.

Figure 26B:
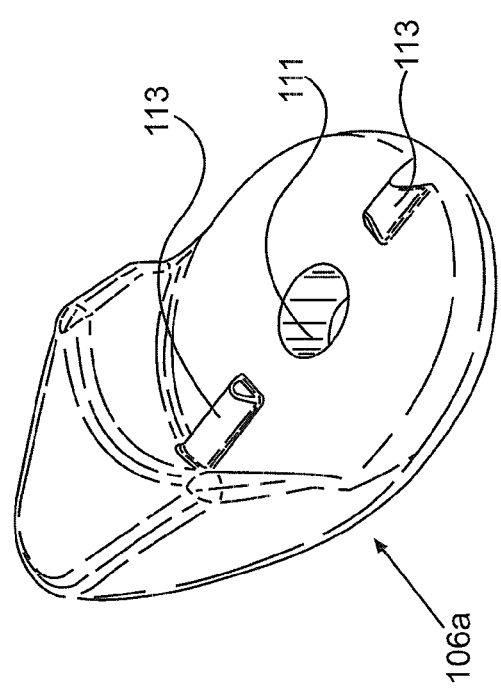
FIG. 26B is a perspective view of the underside of the shoe of FIGS. 22-25.

In a preferred embodiment, shown in FIGS. 6 and 22, shoe 106 is made from a relatively soft, flexible material that allows toe 107 of shoe 106 to bend easily in use from the position shown in FIG. 7, wherein shoe 106 has a length and area that is longer and greater than the inner diameter or area of expanded connector 200, to the position shown in FIG. 26B wherein shoe 106 deforms to fit into an area within inner diameter of expanded connector 200, thereby permitting shoe 106 to be removed through the interior of expanded connector 200 during the final step of the anastomosis procedure. To facilitate bending of toe 107, toe 107 may be connected to shoe 106 by a narrow constriction 109 to provide a weak point in shoe 106 at which bending of toe 107 can occur.

Shoe 106 can be over-molded onto expander head 302 to ensure a good fit and thereby prevent shoe 106 from disengaging from expander head 302 during use of applicator 100. Expander rod or tube 312 may be plastic and be molded simultaneously with expander head 302. Alternatively, expander head 302 may be metal fabricated by, for example, metal injection molding or any other suitable method, in which case, it is possible, but not necessary, to form expander head 302 integrally with expander rod or tube 312 as a single unit. It is preferred in this embodiment to include structure for forming a mechanical bond between expander head 302 and shoe 106 for the purpose of strengthening the connection between these elements.

Figure 26C:
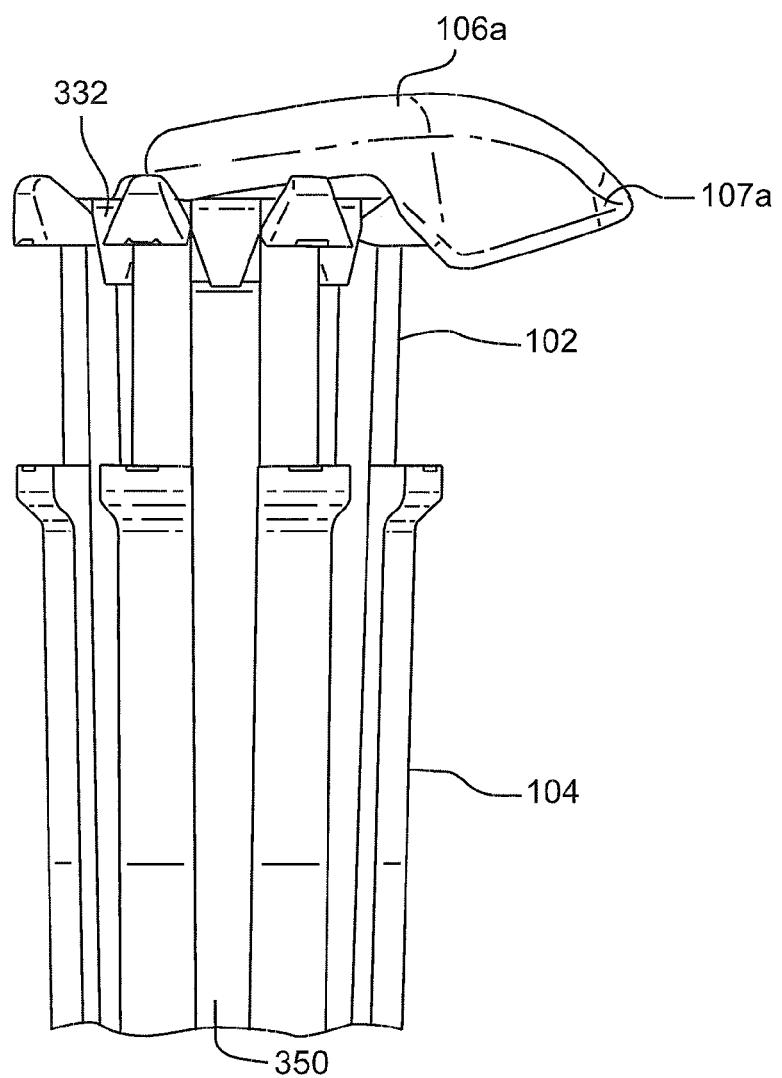
FIG. 26C is a perspective view of the device of FIGS. 23-26B in the expanded position.

In an alternative embodiment, shown in FIGS. 23, 26A and 26C, shoe 106a is preferably fabricated from a hard material. In this embodiment, shoe 106a does not deform, but rather, provision is made for shoe 106a to tilt and move out of the way during operation and removal of the device. Specifically, shoe 106a is attached to a spring 351, for example, via screw 105, as best seen in FIG. 26A. Spring 351 is, in turn, attached to threaded screw 338. This arrangement permits shoe 106a to move upward, radially outward and tilt relative to outer tube 104 during expansion, such as the position shown in FIG. 26C, and subsequently be removed through expanded connector 200.

It is also possible to fabricate shoe 106a and expander head 302 from a single material. In this embodiment, pull tube 352 is preferably flared as shown, for example, in FIG. 25, to increase stiffness of the conical part to provide support for the expansion of applicator 100, thus allowing deployment of connector 200, but the material from which tube 352 is made is flexible enough to allow removal of applicator 100 from connector 200 after the anastomosis is complete.

In another embodiment, the material selected for fabrication of shoe 106a is such that it is capable of forming a chemical bond with the material of expander head 302 to further reinforce the connection between shoe 106a and expander head 302. Alternatively, a mechanical connection and/or an adhesive can be employed for this purpose.

Figure 26D:
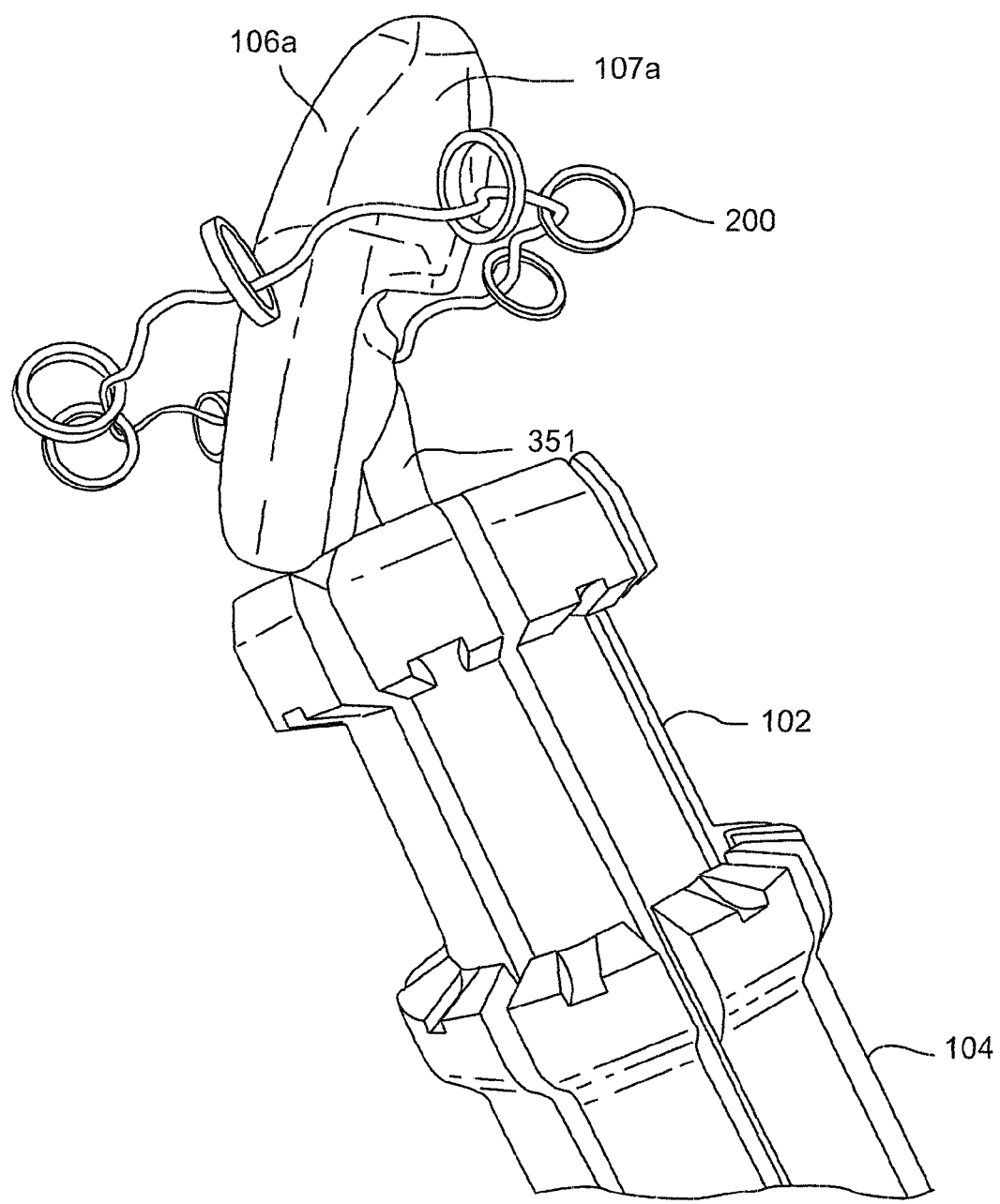
FIG. 26D is a perspective view of the distal end of the applicator of FIG. 26C with the attached shoe in removal position.

In the embodiments shown in FIGS. 24-25, the shoe 106a is formed separately from expander head 332 of FIG. 24, and expander head 342 of FIG. 25, and may be connected to the applicator 100 with a band or cord or thread, which may be elastic, or via a spring 351. In this way, shoe 106a can move from a first, insertion position, which is more radially oriented relative to the central axis of the applicator 100, to a second, removal position, which is more parallel to the central axis, as shown in FIG. 26D, thus reducing the size of the shoe in a plane perpendicular to the applicator. The connecting band or spring 351 is attached to shoe 106a, for example by using a screw through hole 111, and may, but does not need to, run through the entire length of hollow expander rod 350, to be attached at its proximal end.

To allow additional stability of shoe 106a on expander head 332 of FIG. 24, and expander head 342 of FIG. 25, during insertion, shoe 106a can be provided with a key 113 which mates with a corresponding notch 334 or 344 in expander head 332 or expander head 342. Expander head 332 of FIG. 24 has two protuberances 334 for this purpose. FIG. 26B shows the underside of shoe 106a. Shoe 106a includes a recess 111 for engagement with the distal end of expander 300 and keys 113 that mate with corresponding protuberances 334 or 344 in expander heads 332, 342, respectively. Alternatively or additionally, magnetic force can be used to generate additional stability between shoe 106 and expander head 332.

Figure 27E:
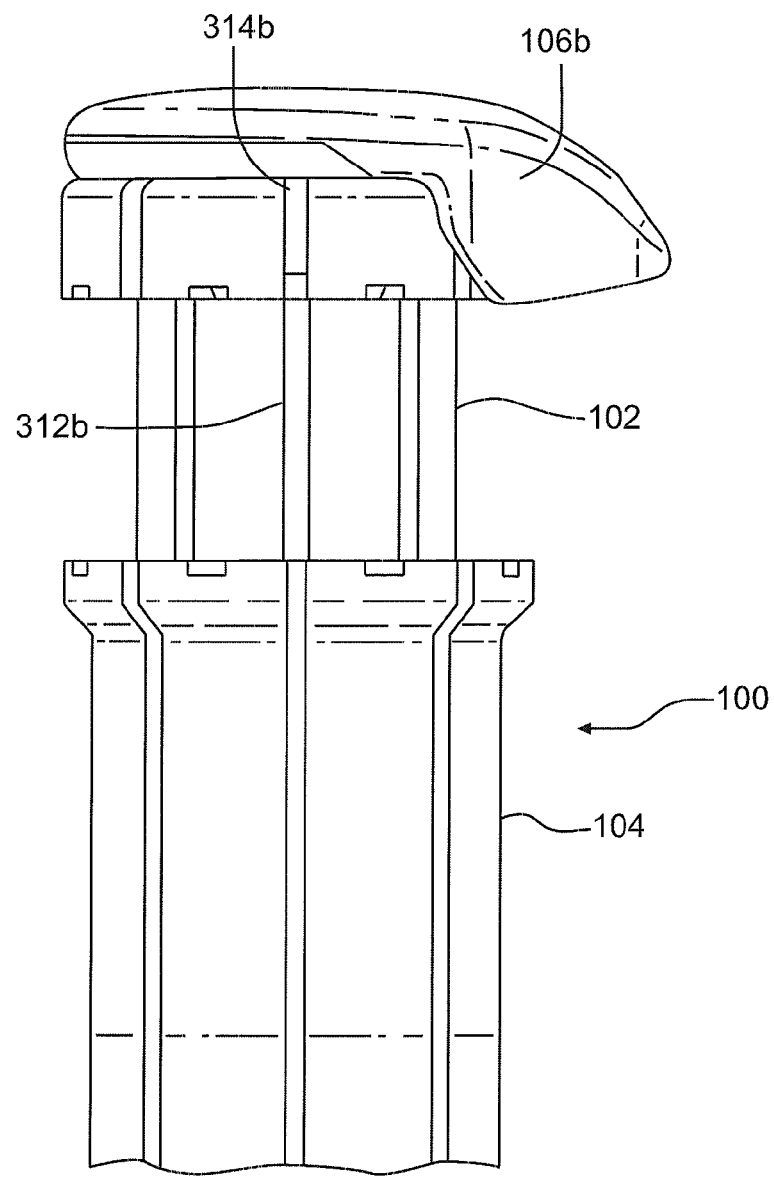
FIG. 27E is a perspective view of the expander of FIGS. 27A-27D in the insertion position.

Referring to FIGS. 27A-27F, there is shown an embodiment of the invention which does not require an expander head. Expander 300b is formed from a combination of expander tube 312b and a flange 314b at the distal end thereof as shown in FIG. 27B. Expander rod 312b may be a hollow tube as shown in FIG. 27D. The proximal end of expander tube 300b may include a threaded connection 338b as shown in FIGS. 27C-27D, or alternatively the spring 351 may be laser-welded or the like, to the expander tube 312b. The device of this embodiment also includes a shoe 106b, shown in FIG. 27A which may be attached via a screw 105b to a spring 351b which may, but need not, run the length of expander tube 312b, as shown in FIG. 27D. The proximal end of spring 351b may be attached to a threaded screw 338b, as shown in FIG. 27D. Shoe 106b is preferably made from a hard material in this embodiment since the whole of shoe 106b moves during expansion, as discussed below.

Figure 27F:
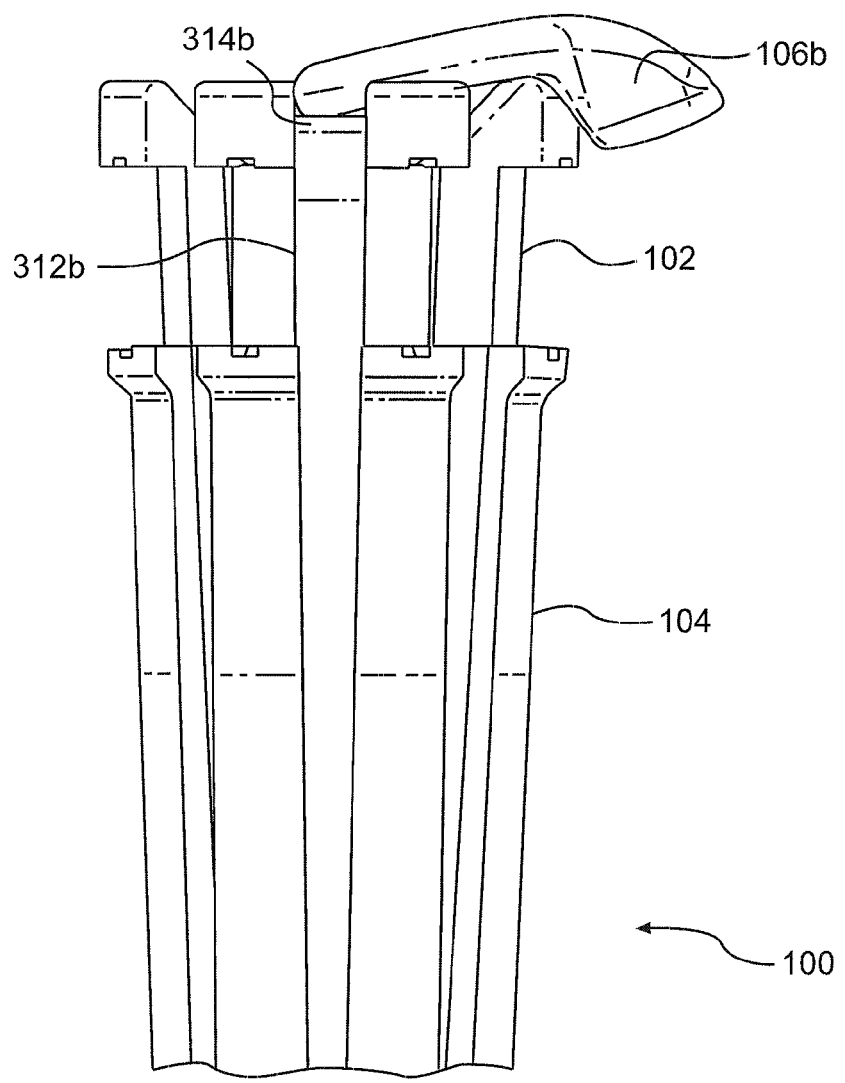
FIG. 27F is a perspective view of the expander of FIGS. 27A-27E in the expanded position.
Figure 28E:
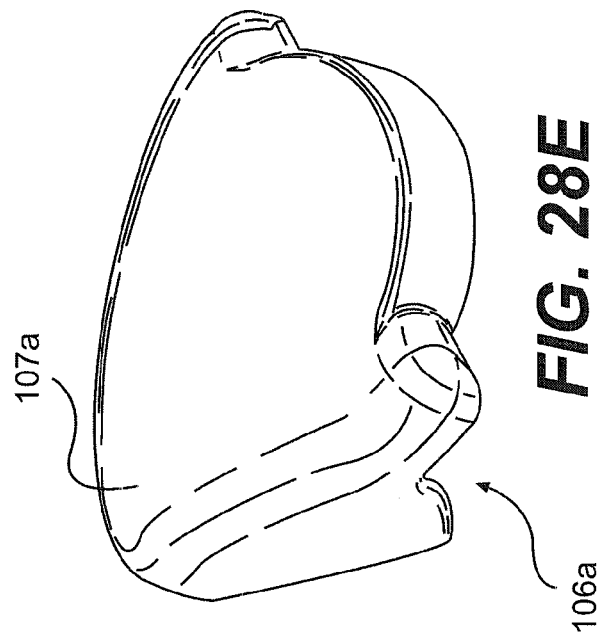
FIG. 28E is a perspective view of the top of the shoe shown in FIGS. 28A-28D.

In the embodiment of FIGS. 27A-27F, expander 300b is pulled proximally to cause expansion of the applicator 100 from the insertion position of FIG. 27E to the expanded position of FIG. 27F. Flange 314b rides on mating surfaces of inner tube 102 to cause expansion of inner tube 102 which, in turn, causes expansion of outer tube 104, as can be seen in FIG. 27F. Since shoe 106b is attached to spring 351b, it is permitted to move from the position shown in FIG. 27E to the position shown in FIG. 27F during expansion. Referring now to FIGS. 28A-28F, there is shown an alternative embodiment of an expander 300a in accordance with the present invention. Expander 300a is formed from a combination of expander head 302a and expander tube 312a. Expander tube 312a may be a hollow tube, as shown, and is provided with a flange 314a at the distal end thereof. The proximal end of expander tube 312a may include a threaded connection 316a as shown in FIG. 28C. Preferably, expander tube 312a is insert molded into expander head 302a to provide a reliable connection between expander tube 312a and expander head 302a to prevent expander head 302a from disengaging from expander tube 312a during use of the applicator 100. For this purpose, flange 314a provides structure for mating with a corresponding structure of the expander head 302a to provide a mechanical bond between expander tube 312a and expander head 302a. In a preferred embodiment, the surface of flange 314a is defined to maximize the bonding force. In another preferred embodiment, the expander head 302a is over-molded onto tube 312a. Expander head 302a is preferably made from a hard material which is capable of expanding inner and outer tubes 102, 104 under the load required to accomplish the expansion.

The shoe 106a is separate from expander head 302a and is over-molded onto a spring wire 117a that provides a mechanical connection between the shoe 106a and the expander tube 312a, and also acts as a hinge that allows shoe 106a to rotate toward a more axial position relative to the center-line of the applicator. Shoe 106a can be made of any biocompatible material, hard or soft, because shoe 106a can move to its second, removal position, without having to rely on deformation of the shoe 106a.

Figure 28D:
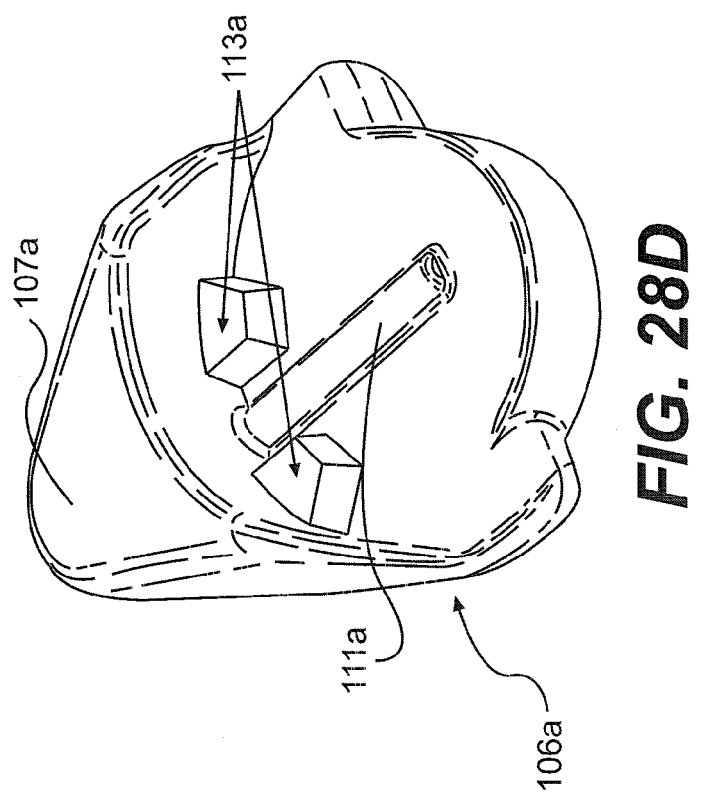
FIG. 28D is a perspective view of the underside of the shoe shown in FIGS. 28A-28C.
Figure 28F:
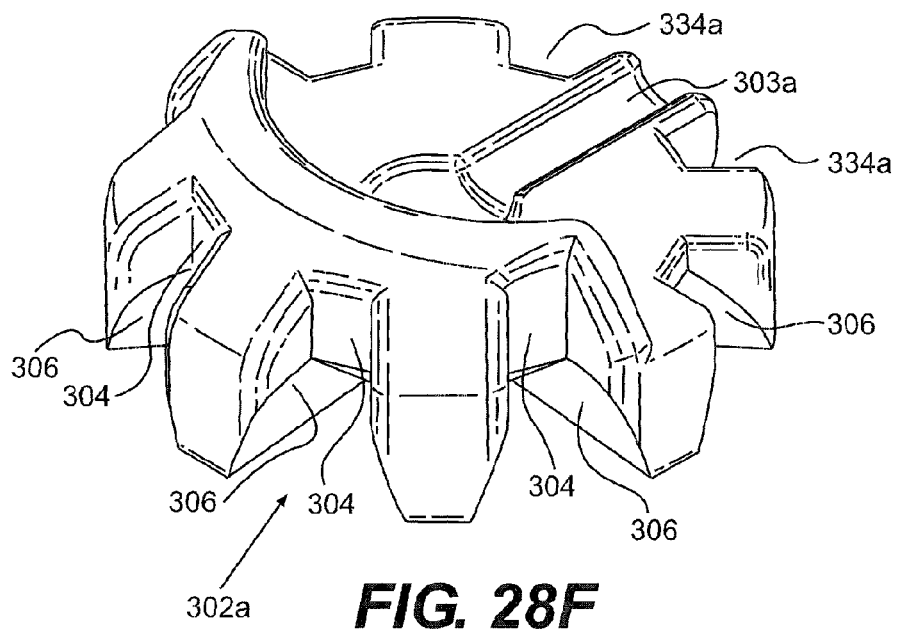
FIG. 28F is a perspective view of the expander head of the expander shown in FIGS. 28A-28C.
Figure 28G:
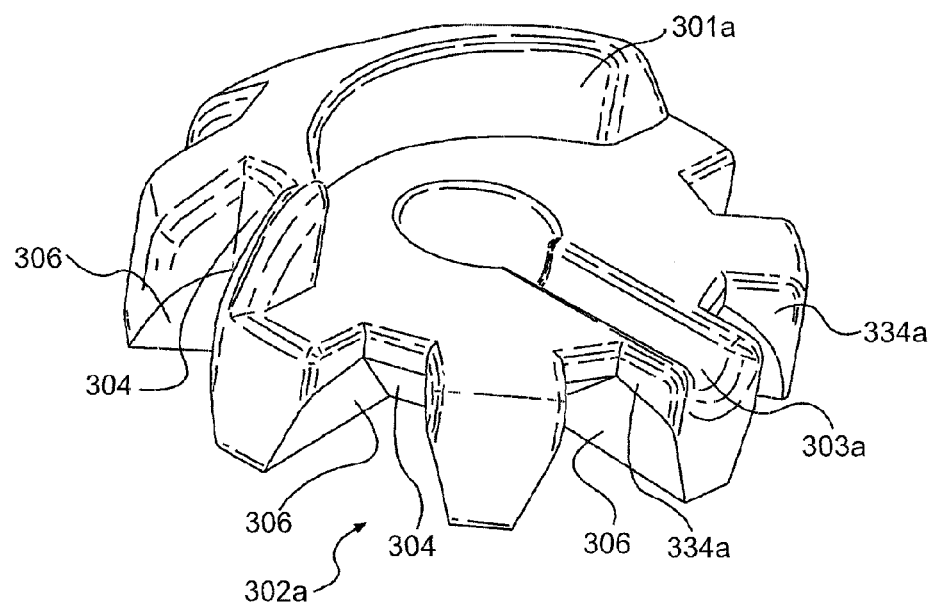
FIG. 28G is another perspective view of the expander head of FIG. 28F.

As shown in FIGS. 28D and 28F-28G, shoe 106a need not include a heel, and thus differs from shoe 106 of FIG. 26B. The advantage of this design is that any chance of inadvertently hooking the heel behind the expanded connector is avoided. To re-establish the streamlined contour, expander 302a includes heel 301a eccentrically on one side.

To provide shoe 106a additional stability relative to expander head 302a, during insertion, shoe 106a can be provided with protuberances 113a which press fit with a corresponding recesses 334a in expander head 302a. This arrangement helps maintain shoe 106a in position relative to expander head 302a during insertion of the device, but permits shoe 106a to move upwardly when anvils 112 of inner tube 102 contact protuberances 113a and thereby release protuberances 113a from recesses 334a during expansion of expander head 302a. Expander head 302a of FIGS. 28F-28G has two recesses 334a for this purpose. FIG. 28D shows the underside of shoe 106a. Shoe 106 includes a longitudinal key 111a for engagement with a slot 303a in the distal end of expander head 302a.

Figure 29C:
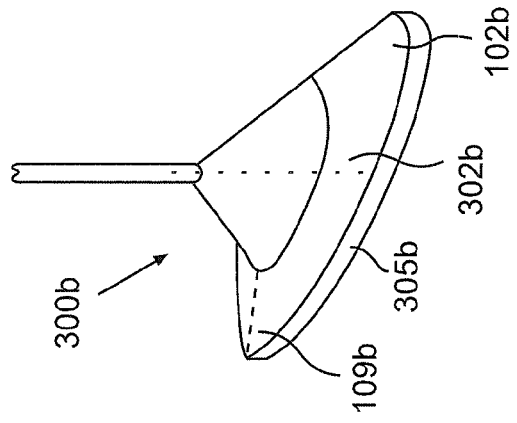
FIGS. 29A-29C show perspective views of an alternative embodiment of an expander designed for oval or elliptical anastomoses.
Figure 29B:
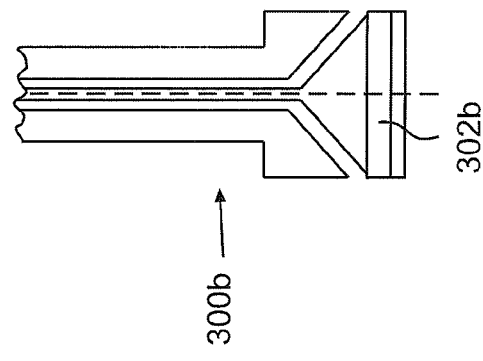
Figure 29A:
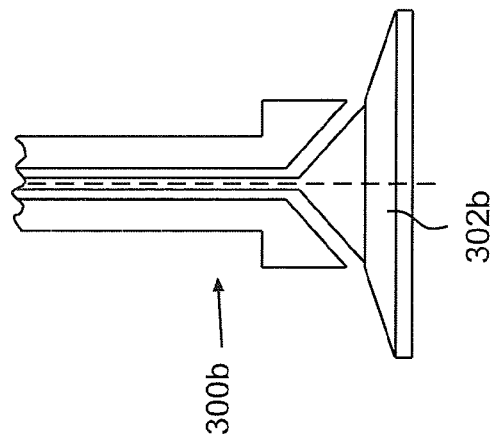

Referring now to FIGS. 29A-29C, there is shown an expander 300b which is suitable for carrying out an oval or elliptical anastomosis by further expanding the device in the axial direction of the target vessel than in the transverse direction. In this embodiment, the expander head 302b is made in an oval shape but is employed with a round applicator, for ease of manufacture. Thus, the conical expander head 302b has an oval ground plane which expands the applicator more in a first direction than in a direction perpendicular to the first direction. The outer edge 305b of the asymmetric expander 300b may be adapted to fit inside the contour of the fingers 118 of inner tube 102. An extra degree of over-expansion in one direction can be achieved by over-sizing the long axis of the expander 300*b*, as shown. Thus, the expander 300*b* also forms an insertion foot, in this case with a symmetrical toe 107*b* and heel 109*b* as a result of the increased size in one direction, which should be directed along the central axis of the target vessel. The initial arteriotomy in the target vessel can be larger, allowing easy insertion of the device using a method much like the perpendicular insertion method described below.

As discussed above, applicator 100 carries out a four-step process to accomplish an anastomosis. The first step is the expansion of inner and outer tubes 102, 104 from an initial state to an intermediate state to thereby expand connector 200. The second step is to move at least one of inner and outer tubes 102, 104 relative to the other of inner and outer tubes 102, 104 from the intermediate state to a release state to form connector 200 into the desired shape for making the anastomosis. The third step is to return inner and outer tubes 102, 104 to their original relative positions, and the fourth step is to return inner and outer tubes 102, 104 to the unexpanded final state. It is not necessary to perform all four steps sequentially, and thus, for example, the third and fourth steps could potentially be combined into a single simultaneous motion of the various moving parts to achieve the objectives of returning inner and outer tubes 102, 104 to their original positions and unexpanded state.

In a preferred embodiment, one component of applicator 100 is held static and other components of applicator 100 are moved relative to the static component. Preferably, outer tube 104 is maintained as the static component since this may simplify the mechanics of the actuation of applicator 100. The following embodiments of drive mechanisms or actuators in accordance with the present invention are described in relation to actuation of an applicator that maintains outer tube 104 in a static position and moves inner tube 102 relative to outer tube 104. Of course, persons of skill in the art are capable of applying the basic concepts of the various actuators described below to embodiments where, for example, inner tube 102 is maintained in a static position and outer tube 104 is moved relative to inner tube 102, or to embodiments where both inner and outer tubes 102, 104 are moved relative to one another.

Drive Mechanisms

In performing the anastomosis procedure, a connector is deployed via two systems, the activation mechanism and the drive mechanism or actuator. Energy, which may be mechanical, hydraulic, pneumatic, electrical, etc., is input into the activation mechanism. The activation mechanism then translates the input energy into a motion that drives the drive mechanism. Preferably, the activation mechanism translates the input energy into either a pulling motion or a pulling and then a releasing motion that drives the drive mechanism. There are four basic types of drive mechanisms described below, a dual-cam drive mechanism, a single-cam/single-spring drive mechanism, a dual-spring drive mechanism and a shape memory alloy mechanism. Each system is compatible with one type of output motion from the activation mechanism, either pull or pull-and-release. The drive mechanism or actuator utilizes this motion to manipulate the tubes and deploy the connector.

Dual-Cam Actuation

Figure 30A:
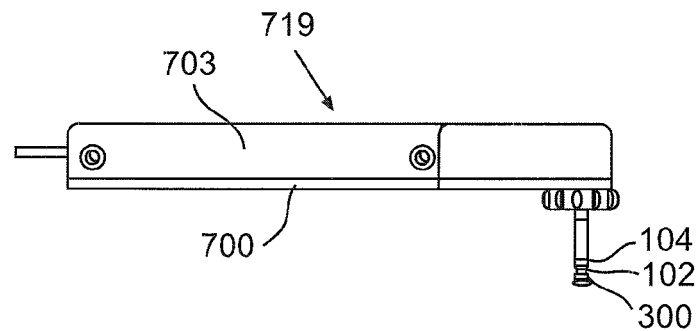
FIG. 30A is a perspective view of a dual-cam actuator in accordance with the present invention.

In a mechanism that utilizes dual-cam, direct actuation, the amount of expansion of the connector and the compression of the staple elements are independently governed by cam tracks. Once the inner and outer tubes 102, 104 have deployed the connector, the cam tracks force the inner and outer tubes 102, 104 back to their original position, allowing for positive return of the device to its original position without the use of stored energy. This configuration generally employs a continuous pull from an activation mechanism. Each face of the cam may have a unique cam track. The geometry of the cam tracks dictates the timing of, and controls the two distinct motions required for the anastomosis. Referring to FIG. 30A, there is shown a device 719 for controlling the relative positions of outer tube 104, inner tube 102 and expander 300 relative to each other comprising a cover 703 and a lever and cam actuator 700.

Figure 30B:
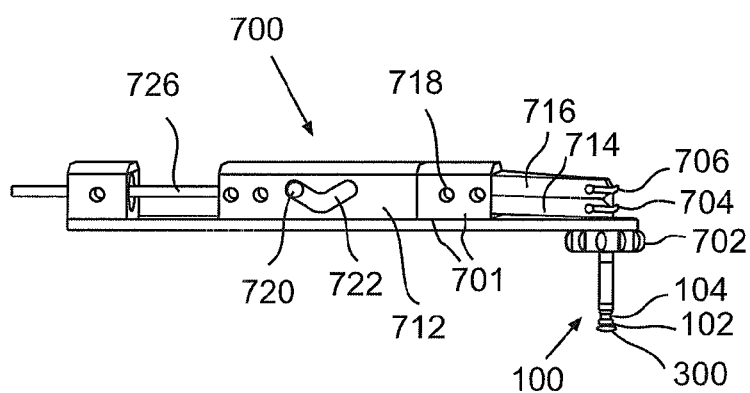
FIG. 30B is a perspective view of one side of the dual-cam actuator of FIG. 30A with the housing removed.
Figure 30C:
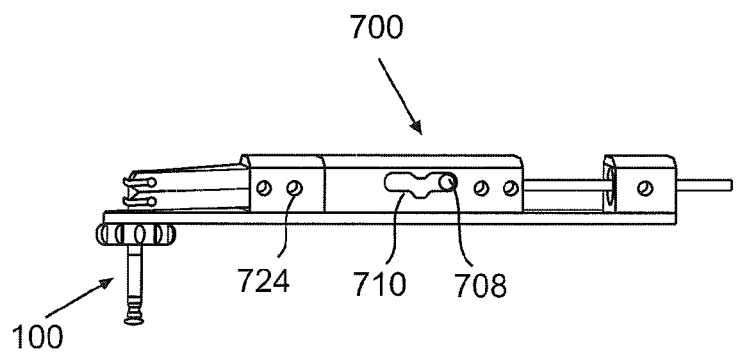
FIG. 30C is a perspective view of opposite side of the dual-cam actuator of FIG. 30B with the housing removed.

Referring to FIG. 30B, there is shown a lever and cam actuator 700. Lever and cam actuator 700 is connected to applicator 100. Outer tube 104 is connected to rotatable connection 702. Inner tube 102 is fixedly connected to disk 704. Expander 300 is fixedly connected to disk 706. Rotatable connection 702 can freely rotate 360 degrees relative to lever and cam actuator 700. Disc 706 can freely rotate 360 degrees relative to lever 716. Disc 704 can freely rotate 360 degrees relative to lever 714. This allows the user to suitably position applicator 100 and lever and cam actuator 700 relative to the anastomosis site.

In this embodiment, the proximal end of expander 300 is connected to disk 706, via threaded connector 316. Disks 704, 706 are positioned as shown in FIG. 30B to engage with levers 714 and 716, respectively, whilst being permitted to rotate about the axis of applicator 100. Levers 714, 716 are adapted for lateral movement at a substantially 90-degree angle relative to disks 704, 706 being pivotally mounted in pivot points 724, 718 respectively. Pivot points 724, 718 are contained in chassis 701. Respectively levers 714 and 716 include cam followers 708 and 720, adapted to ride in cam tracks 710 and 722. Said cam tracks are housed in shuttle 712. Shuttle 712 is attached to a cable 726, or other actuation means. Cover 703 is fastened in place to chassis 701 thereby limiting the movement of shuttle 712 to one along the length thereof.

In operation, translation of cable 726 in a proximal direction causes translation of shuttle 712 in a proximal direction, which causes cam tracks 710 and 722 to subsequently cause the translation of cam followers 708 and 720 as dictated by the unique configuration of the cam tracks. Respectively, translation of cam followers 708 and 720 cause levers 714, 716 to pivot about pivot points 724, 718. Since levers 714, 716 are pivotally mounted at pivot points 724, 718, distal movement of the proximal portions of levers 714, 716, as shown in FIG. 30B, translates to proximal movement of the distal portions of levers 714, 716 which, in turn, translates to proximal movement of inner tube 102 and expander 300. Similarly, proximal movement of the proximal portions of levers 714, 716 translates to distal movement of inner tube 102 and expander 300 as a result of the pivotal mounting of the levers 714, 716.

As a result, in the starting position, cam followers 708, 720 are located at the distal-most position within cam tracks 710, 722. As cam followers 708, 720 are pulled proximally within cam tracks 710, 722, cam followers 708, 720 move downwardly at different times to first cause lever 716 to pull the expander proximally relative to outer tube 104, and then cause lever 714 to pull inner tube 102 proximally relative to outer tube 104. A second embodiment of a dual-cam actuation mechanism is depicted in FIGS. 31-37. Front-end portion 960 shown in FIG. 31 includes a housing 964. Dual-cam 961 is mounted at its center point 965 for rotational movement in housing 964. Each side of cam 961 has a cam track 966, 967 as shown in FIGS. 35 and 37, respectively. Cam tracks 966, 967 are generally c-shaped (but are not identical) and are designed to produce coordinated linear movements of inner tube 102 and pull tube 352 that cause the expansion and compression of connector 200, and then return inner tube 102 and pull tube 352 to their starting positions. Pull tube cam track 966 includes a first section 966a, a second section 966b and a third section 966c. Similarly, inner tube cam track 967 includes a first section 967a, a second section 967b and a third section 967c. Thus, as seen in FIGS. 34-37, pulling a cable 950 attached to cam 961 in the direction indicated by arrow A causes cam track 966 to rotate in a clockwise direction about center point 965, and cam track 967 (as depicted in FIG. 37) to rotate in a counter-clockwise direction about center point 965. Inner tube 102 is connected to inner tube bracket 968, which is provided with a first cam follower 969 that is constrained to ride in cam track 967 of cam 961. Pull tube 352 is connected to pull tube bracket 970, which is provided with a second cam follower 971 that is constrained to ride in cam track 966 of cam 961. As a result, rotation of cam 961 will cause the brackets 968, 970 to linearly move inner tube 102 and pull tube 352, as shown in FIGS. 33A-33C.

To allow rotation of front-end portion 960 relative to applicator 100 and expander 350, special connections are provided between pull tube 352 and pull tube bracket 970 and between inner tube 102 and inner tube bracket 968. More specifically, pull tube 352 is provided with a disk 972 at or near the proximal end of pull tube 352. Pull tube bracket 968 is affixed to pull tube disk 972 to prevent relative movement between pull tube bracket 968 and pull tube disk 972 in a longitudinal direction, but to allow relative rotational movement between pull tube bracket 968 and pull tube disk 972. Similarly, inner tube 102 is provided with an inner tube disk 973 at or near the proximal end of inner tube 102. Inner tube bracket 970 is affixed to inner tube disk 973 to prevent relative movement between inner tube bracket 970 and inner tube disk 973 in a longitudinal direction, but to allow relative rotational movement between inner tube bracket 970 and inner tube disk 973. In this manner, front-end portion 960 is permitted to freely rotate relative to applicator 100 to thereby allow front-end portion 960 to be positioned at a variety of different orientations relative to applicator 100.

Figure 32:
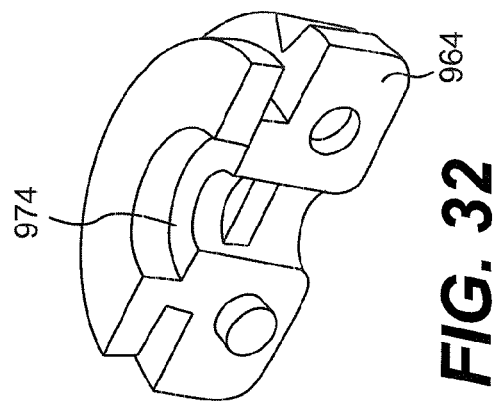
FIG. 32 is a perspective view of a portion of the applicator of FIG. 31 showing details not shown in FIG. 31.
Figure 31:
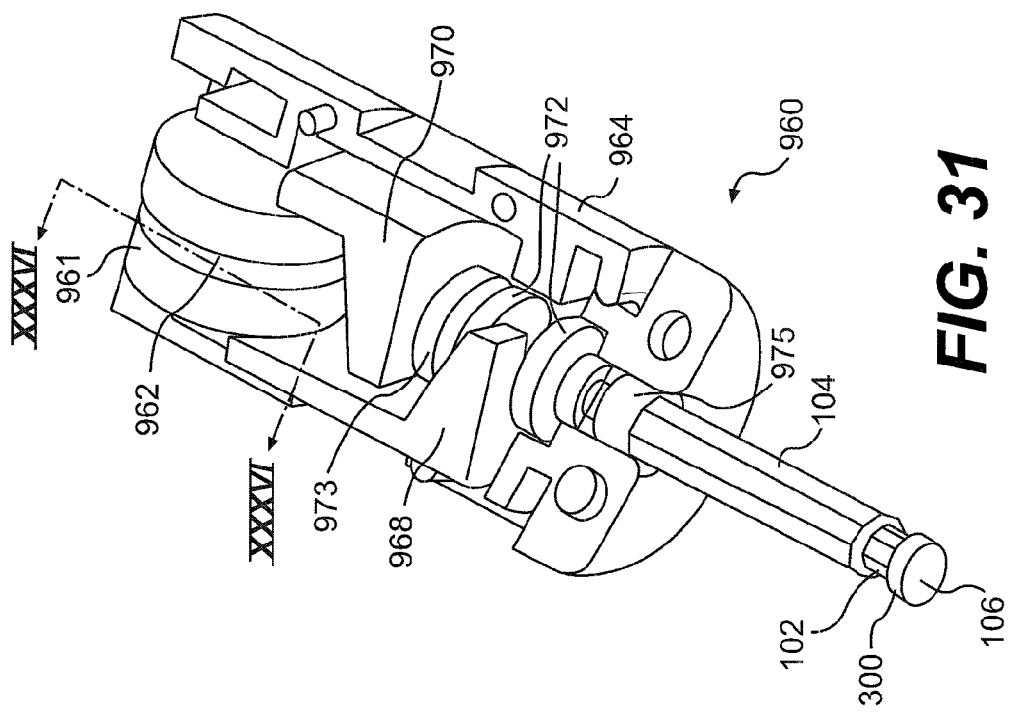
FIG. 31 is a partial cutaway view of an alternative embodiment of a dual-cam applicator.

Referring to FIG. 32, it is shown that housing 964 includes a step 974 for holding outer tube 104 in place against the pulling and expansion forces exerted during the anastomosis procedure. Outer tube 104 may include an outer tube disk 975 for resting against step 974.

Figure 52A:
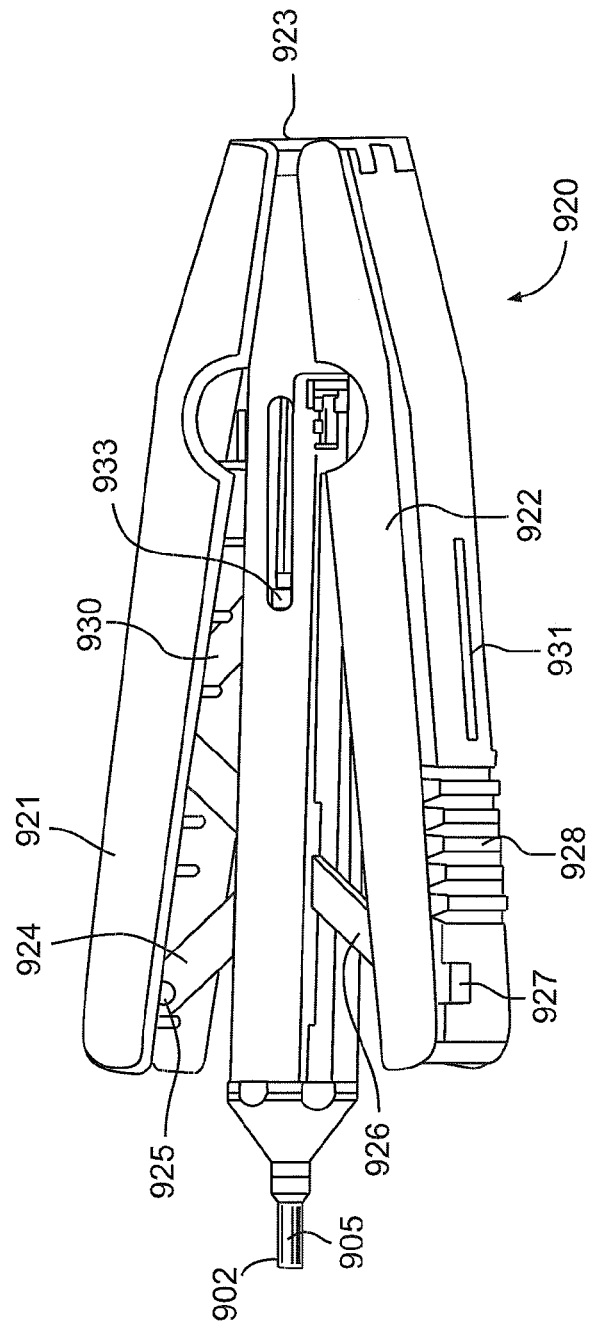
FIGS. 52A-52C are perspective views of one embodiment of a handle portion of the actuator of either of FIGS. 1-2.

Referring to FIGS. 33A-33C and 34-37, the operation of the current embodiment is depicted. A user can impart a pulling motion on cable 950 (FIG. 36) by squeezing grips 921, 922 of a handle portion 920 (FIG. 52A). The initial pull of cable 950 moves the parts of front-end portion 960 from the initial state shown in FIG. 33A, where cam follower 969 resides within section 967a (FIG. 37) and cam follower 971 resides within section 966a (FIG. 35), to an expansion state shown in FIG. 33B, where cam follower 971 resides within section 966b at a position where the distance $x_2$ between cam track 966 and the perimeter of cam 961 is greater than the distance $x_1$ between cam track 966 and the perimeter of cam 961 at position 966a. During this initial movement, rotation of cam 961 causes bracket 970 and hence pull tube 352 to move proximally relative to outer tube 104 from the position of FIG. 33A to the position of FIG. 33B thereby expanding connector 200. During this movement, cam follower 969 has not reached second section 967b of cam track 967, and as a result, both inner and outer tubes 102, 104 are held stationary. A dwell in cam 961 can be designed prior to movement from the initial state to the expansion state so as to allow for bracket clearance and kinking in cable 950.

As the user continues to pull on cable 950, cam 961 continues to rotate causing inner tube cam follower 971 to enter second section 967b of cam track 967 and pull tube cam follower 969 to travel farther along second section 966b of cam track 966, at which point front-end portion 960 moves from the expansion state to the compression state. As a result, both pull tube 352 and inner tube 102 simultaneously move proximally relative to outer tube 104, thereby compressing connector 200 between inner tube 102 and outer tube 104. Pull tube 352 is moved proximally with inner tube 102 to ensure that connector 200 is maintained in its expanded condition as connector 200 is compressed between inner tube 102 and outer tube 104.

As cable 950 is further pulled, cam 961 continues to rotate until inner tube cam follower 971 enters third section 967c and pull tube cam follower 969 travels farther along section 966b of cam track 966, at which time pull tube 352 and inner tube 102 simultaneously move distally relative to outer tube 104, thereby releasing connector 200 from slots 128, 138 of inner and outer tubes 102, 104. Finally, as cable 950 is further pulled, pull tube cam follower 969 enters third section 966c, at which point pull tube 352 is moved distally with respect to the inner and outer tubes 102, 104, thereby unexpanding inner and outer tubes 102, 104.

The use of dual cam 961 converts a cable pull motion into a series of motions: first moving inner tube 102 proximally to cause connector 200 to expand; then moving both inner tube 102 and pull tube 352 proximally to compress connector 200; then followed by moving both inner tube 102 and pull tube 352 distally to release connector 200 from slots 128, 138; and finally moving pull tube distally to unexpand inner and outer tubes 102, 104.

Dual Spring Actuation

The second type of drive mechanism is a dual-spring mechanism. This mechanism has two features that allow for precise and adjustable control over the amount of connector expansion and the amount of compression of the staple elements of the connector. The dual-spring device relies on stored energy to return the inner tube and pull tube to their initial positions. The dual-spring mechanism generally requires a pull and release actuation source. Radial expansion of the connector is dictated by the gap between an expansion disk and the fingers on the front-end bracket. The distance between the compression disk and the interior shoulders on the turn grip determines the amount of compression of the staple elements.

Figure 38:
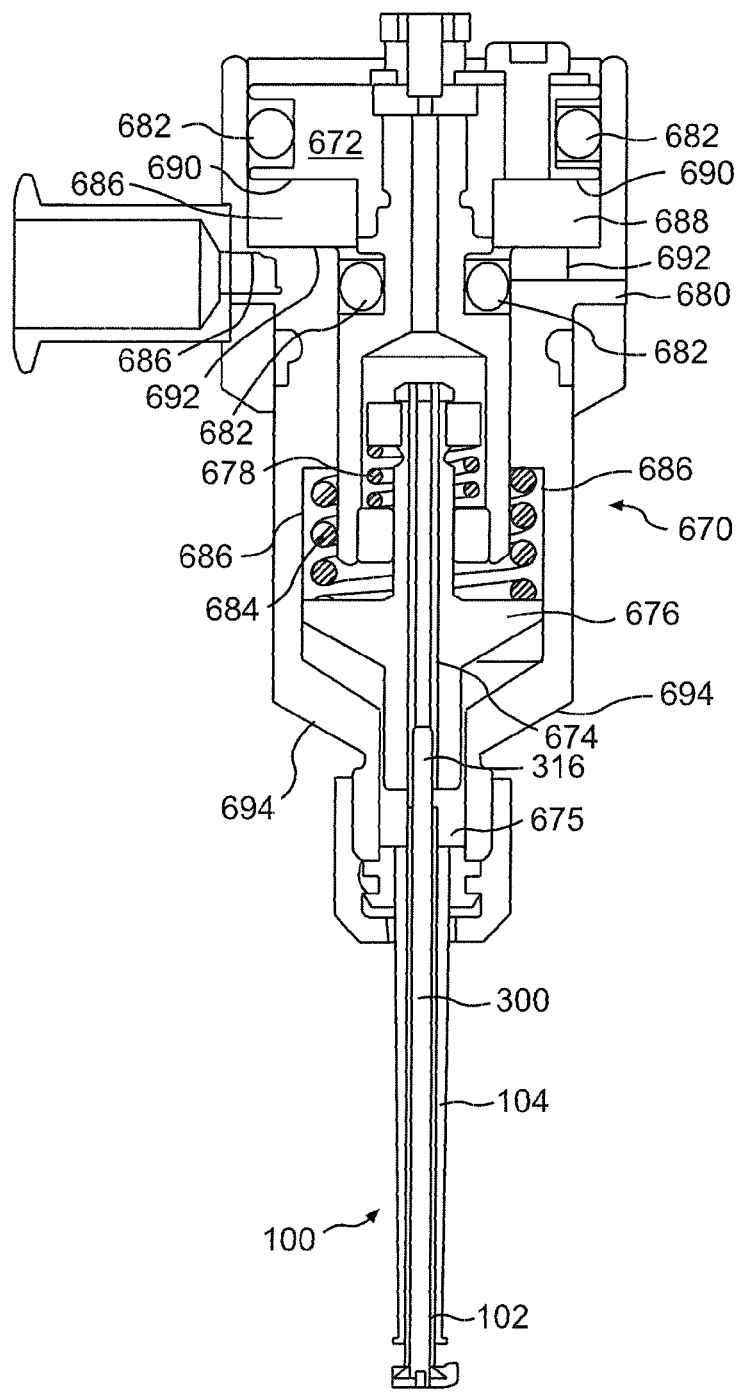
FIG. 38 is a cutaway view of a hydraulic actuator for an applicator in accordance with the present invention.

Referring now to FIG. 38, there is shown a dual-spring hydraulic actuator 670 in accordance with the present invention. Similar hydraulic actuators can be used to pull a cable connected to an expander, but hydraulic actuator 670 shown in FIG. 38 operates applicator 100 in a different manner than other hydraulically actuated embodiments described below. More particularly, in the embodiment of FIG. 38, hydraulic actuator 670 is capable of separately moving expander 300 and inner tube 102. Expander 300 may be directly connected to a first movable section 672 (which may be a piston) via a rod 674. Preferably rod 674 is connected to expander 300 by a threaded connection 316. Hydraulic actuator 670 is also connected to, or engaged with, inner tube 102 of applicator 100 via second movable section 676 (which may also be a piston) at location 675. As a result, hydraulic actuator 670 is capable of directly moving both inner tube 102 and expander 300.

The embodiment of FIG. 38 employs differential spring force to obtain the required movements of expander 300 and inner tube 102 from a single injection of hydraulic fluid. More specifically, first movable section 672 is connected to second movable section 676 via a first spring 678 and first movable section 672 is mounted to be freely movable relative to housing 680 by a series of fluidly sealed mounts 682. Second movable section 676 is positioned for free movement within housing 680 but is biased distally relative to outer tube 104 by the force of second spring 684 mounted against a lower surface 686 of housing 680. Second spring 684 exerts a stronger downward force than first spring 678 when hydraulic actuator 670 is in its initial position.

In operation, hydraulic fluid is injected via inlet 686 into fluid chamber 688 of housing 680. The hydraulic fluid exerts an upward force against contact surface 690 of first movable section 672 to move first movable section 672 proximally relative to outer tube 104, which pulls expander 300 proximally to thereby expand applicator 100. Proximal movement of first moveable section 672 also compresses first spring 678 until the proximal force of compressed first spring 678 equals the distal force applied by second spring 684 at which point the intermediate state is reached.

Once the proximal force of compressed first spring 678 equals or exceeds the distal force of second spring 684 the proximal movement of first movable section 672 is transferred via first spring 678 to second movable section 676. This results in proximal movement of both expander 300 and inner tube 102 to expand connector 200. Hydraulic fluid continues to be injected at the same rate until the release state is reached. The release state is reached when the proximal force exerted by the hydraulic fluid on contact surface 690 equalizes with the combined distal force exerted by compressed first and second springs 678, 684. At this point, the hydraulic fluid is discharged and hydraulic actuator 670 returns to its final (and original) position by first uncompressing inner tube 102 and outer tube 104 by moving expander 300 and inner tube 102 distally relative to outer tube 104, and then unexpanding inner tube 102 and outer tube 104 by moving expander 300 distally relative to outer tube 104. Surfaces 692 and 694 of housing 680 ensure that hydraulic actuator 670 returns to a consistent position in the final state.

Referring to FIGS. 39A-39C, there is shown the operation of a device similar to the device of FIG. 38, the only exception being that the hydraulic fluid is replaced by pulling a cable 696 to move first movable section 672. A significant advantage of the embodiment of FIGS. 39A-39C is that the arrangement shown, due to its radial symmetry, does not constrain rotation of applicator 100 relative to the actuator and thus, the user has a greater degree of freedom in positioning the actuator relative to applicator 100 for difficult to reach anastomosis sites. In this embodiment, applicator 100 can rotate 360 degrees relative to the actuator. In a preferred embodiment, a locking mechanism or frictional resistance can be employed to hold applicator 100 in a specific position relative to the actuator once the desired anastomosis site is selected. Such a locking mechanism or frictional resistance may be employed in any of the embodiments of the invention that permit free rotation of the actuator relative to the applicator, for this purpose.

Figure 40C:
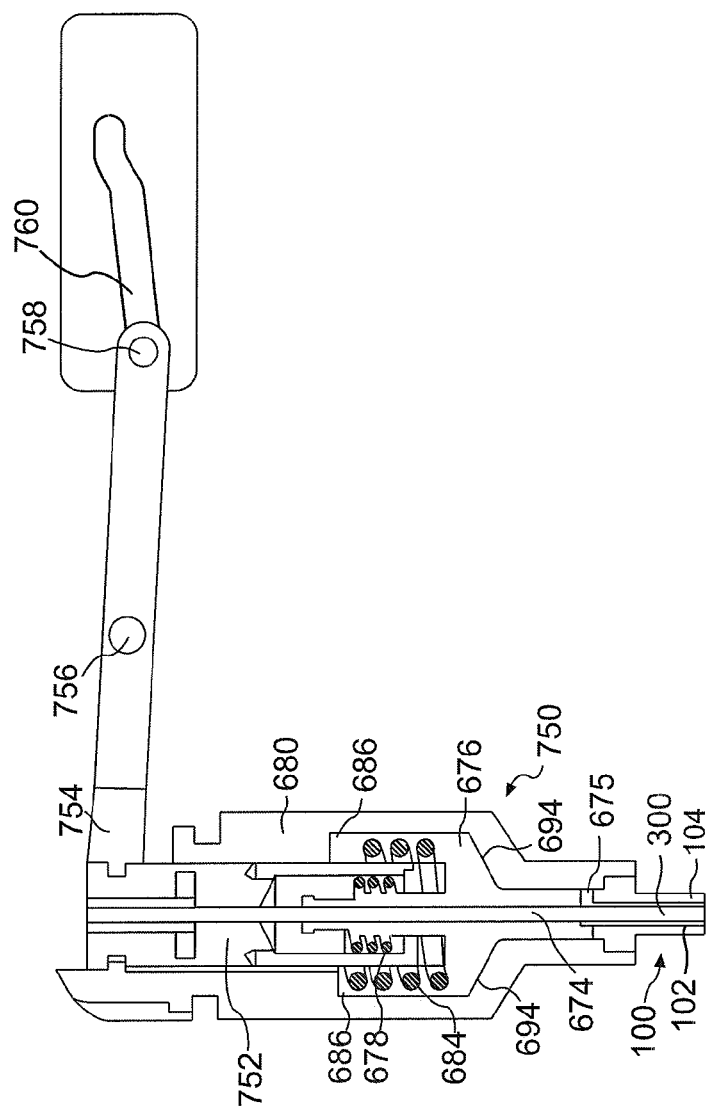

Referring now to FIGS. 40A-40C, there is shown the movement of a dual spring single lever straight cam actuator 750. Actuator 750 is essentially the same as actuator 670 of FIG. 38, except that a single lever straight cam is employed to provide the distal movement of first movable portion 752 of the actuator 750, rather than the use of hydraulic fluid as in the embodiment of FIG. 38.

To provide the distal movement of first movable portion 752, the single lever straight cam actuator 750 employs a lever 754 connected to first movable portion 752. Lever 754 is pivotally mounted at pivot point 756 and includes a cam follower 758 adapted to follow cam track 760. Cam track 760 is attached to a cable 762.

To go from the initial state of FIG. 40A to the expanded state of FIG. 40B, cam track 760 is pulled proximally relative to cable 762 to cause cam follower 758 to move the proximal side of lever 754 downwardly. Due to the pivotal mounting of lever 754 at pivot point 756, this motion causes the distal side of lever 754 to move upwardly, thereby pulling first movable portion 752 proximally relative to outer tube 104 against the force of first spring 678. At this position, pull tube 352 is drawn back proximally relative to outer tube 104. As cam track 760 is moved further proximally relative to cable 762, actuator 750 moves from the expanded state of FIG. 40B to the compression state of FIG. 40C, thereby causing first movable portion 752 to again move proximally relative to outer tube 104. This movement, in turn, causes second movable portion 676 to move proximally relative to outer tube 104 by virtue of the connection of the first and second movable portions via first spring 678. To return to the final state, cam track 760 is moved back to the distal or initial position shown in FIG. 40A, thereby first uncompressing inner tube 102 and outer tube 104 by moving expander 300 and inner tube 102 distally relative to outer tube 104, and then unexpanding inner tube 102 and outer tube 104 by moving expander 300 distally relative to outer tube 104. This type of cam and lever actuator can be adapted for use with any of the other embodiments of the invention described above by a person of ordinary skill in the art.

Figure 41:
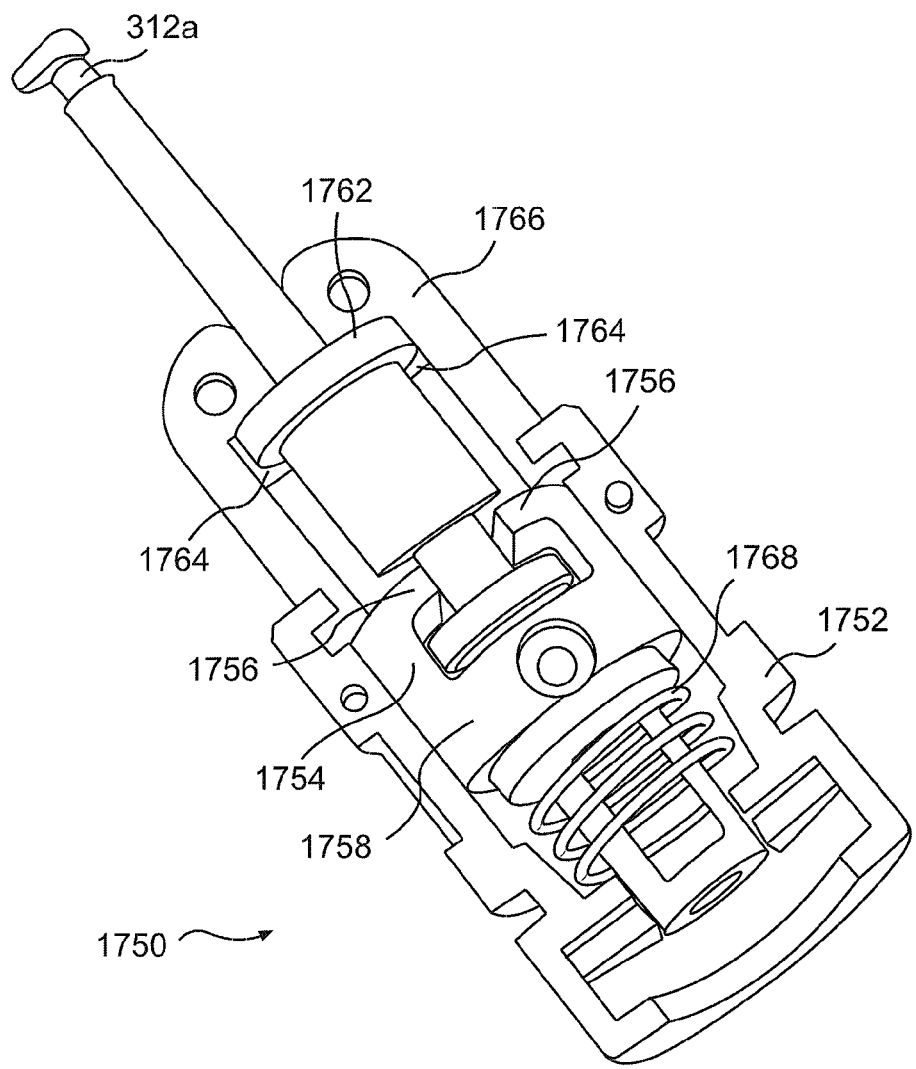
FIG. 41 is a cutaway view of an alternative embodiment of a dual-spring actuator.
Figure 42A:
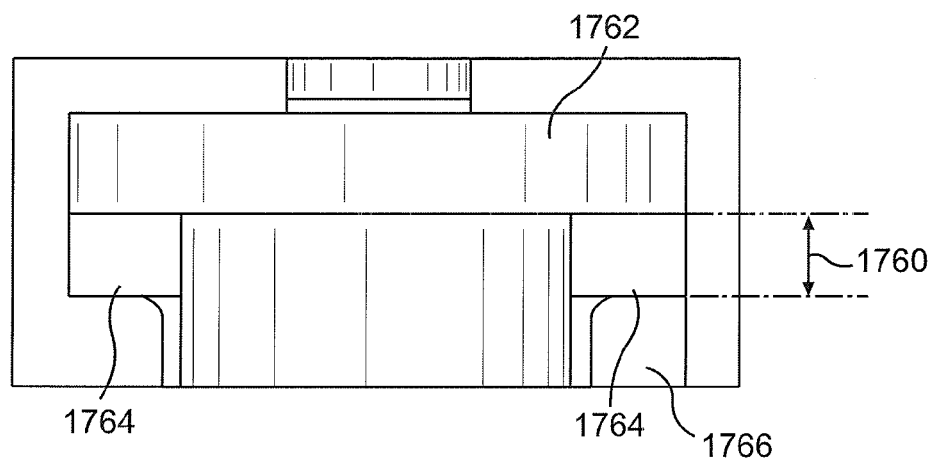
FIGS. 42A-42B show details of portions of the dual spring actuator of FIG. 41.

Referring now to FIG. 41 there is shown a cutaway view of another embodiment of a dual-spring actuator 1750 in accordance with the present invention. The dual-spring applicator 1750 includes a housing 1752. Radial expansion of the connector 200 is dictated by movement of an expansion disk 1754 and fingers 1756 on the front-end bracket 1758. The amount of staple finger compression is determined by the distance 1760, shown in FIG. 42A, between the compression disk 1762 and interior shoulders 1764 on the turn grip 1766 of housing 1752.

Figure 42B:
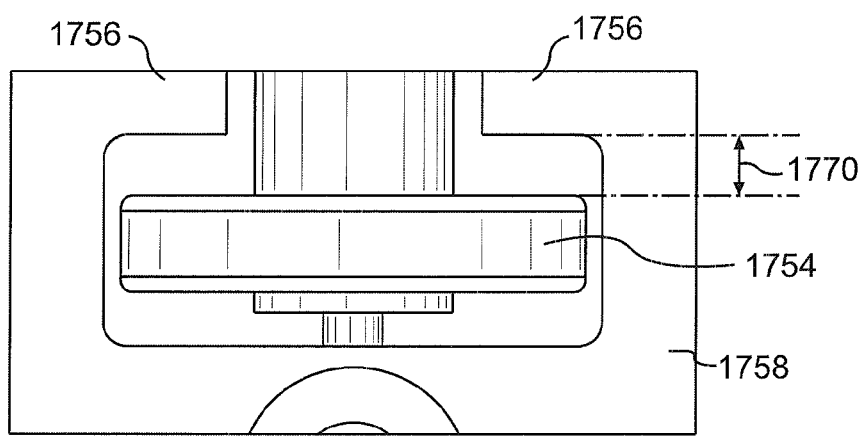

Compression disk 1762 is threaded onto a proximal portion of inner tube 102. Front-end bracket 1758 is threaded onto a proximal portion of expander rod or tube 312a. The expansion disk 1754 is connected to the compression disk 1762. A pre-tensioned spring 1768 rests between the inside face of the compression disk 1762 and an interior wall in turn grip 1766. As the front-end bracket 1758 translates proximally, the expander rod or tube 312a will move with it. After connector 200 is fully expanded by movement of distance 1770 shown in FIG. 42B, fingers 1756 on the front-end bracket 1758 contact expansion disk 1754. Once this occurs, inner tube 102 move in tandem with expander rod or tube 312a (and front-end bracket 1758) and translate until compression disk 1762 contacts shoulders 1764 of turn grip 1766, at which time compression of the connector 200 is complete.

Figures 43A, 43B, 43C, 43D:
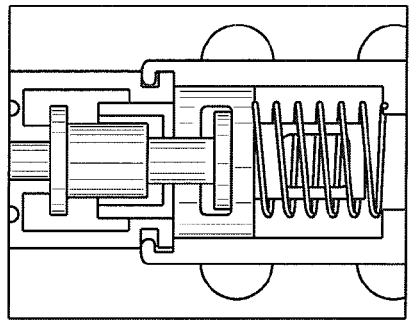
FIGS. 43A-43D show the movements of the dual spring actuator of FIG. 41.

The full movement sequence of the embodiment of FIG. 41 is shown in FIGS. 43A-43D. FIG. 43A shows the initial position of applicator 1750. FIG. 43B shows the connector expansion step. FIG. 43C shows the connector compression step and FIG. 43D shows the applicator returned to its initial position.

For optimal maneuverability under port access conditions, and especially when working transvascularly, the activating mechanism should be as small as possible, preferably built within a catheter tip. One way to realize this is the device 1500 shown in FIG. 44, which effects the desired sequence of first expanding the anvils to a larger diameter, and then moving together the paired anvils by simply pulling rod 1502. Device 1500 includes an outer tube having a bore and has a diaphragm 1508 disposed therein, an inner tube 102 having a bore and being disposed within the bore of outer tube 104, and a pulling rod 1502 disposed within the bore of inner tube 102 and outer tube 104. Pulling rod 1502 includes an expansion cone 1504 on the distal end and a ring 1506 fixed more proximally. A primary, relatively weak spring 1510 is disposed between ring 1506 of pulling rod 1502 and diaphragm 1508 of outer tube 104. A secondary, larger and stronger spring 1512 encircles primary spring 1510 and is disposed between the back end of inner tube 102 and diaphragm 1508 of outer tube 104.

In operation device 1500 works as follows. Pulling central rod 1502 relative to outer tube 104 initiates compression of primary spring 1510. The stiffness of secondary spring 1512 is chosen in such a way that inner tube 102 remains at the same position relative to outer tube 104. Inner tube 102 and outer tube 104 and connector 200 start to expand. When expansion cone 1504 reaches a certain locking position with inner tube 102, the secondary spring 1512 will start to be compressed. The force required to pull the central rod 1504 will of course increase. Now, expansion cone 1504 together with the inner tube 102 will start moving relative to the outer tube 104, and the joining means, e.g. staples, clips or the like, of connector 200 will be deformed, while the expanded state is maintained. After thus deploying connector 200, central rod 1502 is released. Consequently, first the anvils will move to their starting positions and finally the primary spring 1510 will reverse the expansion, permitting withdrawal of device 1500.

It will be understood that the mechanism can take different configurations, while still relying on the same principles. For example, device 1500 can be adapted in such a way that springs 1510 and 1512 are not positioned concentrically, but serially, or in another, different position. Also, the axial force in the distal direction, generated by the elastic deformation of inner tube 102 upon expansion, can be used instead of spring 1510. Ring 1506 and spring 1510 can thus be omitted without compromising functionality. Also, by tailoring the characteristics of spring 1510, other sequences of anvil expansion and moving the paired anvils towards each other can be effected, if desired.

Single-Cam/Single-Spring Actuation

A feature of this actuation mechanism is that it allows for precise and adjustable control of the amount of connector expansion. The cam track guides the pull tube from its initial position, to the expansion and compression positions, and back to its initial position, without the use of stored energy. The single-cam/single-spring actuation device generally requires a continuous pull from an actuation source for operation.

The sequence of radial expansion of the connector followed by axial compression of the staple elements is governed by the amount of gap between the inner tube disk and the pull tube bracket, as well as the geometry of the cam track. The inner tube disk may be threaded onto the pull tube. A pre-tensioned spring rests between the inside face of the inner tube disk and an interior wall in the turn grip. Both sides of the cam have the same cam track in this device. The bosses on the bracket are constrained to follow the cam tracks. As the cam rotates, the bracket translates and pulls the pull tube with it. After the connector has expanded, the fingers on the bracket come in contact with the shoulder on the inner tube disk to cause the inner tube to move in tandem with the pull tube. The geometry of the turn grips and the pull tube bracket permit the front end to articulate. The dwell in the cam allows for bracket clearance and kinking in the cable.

Figure 45:
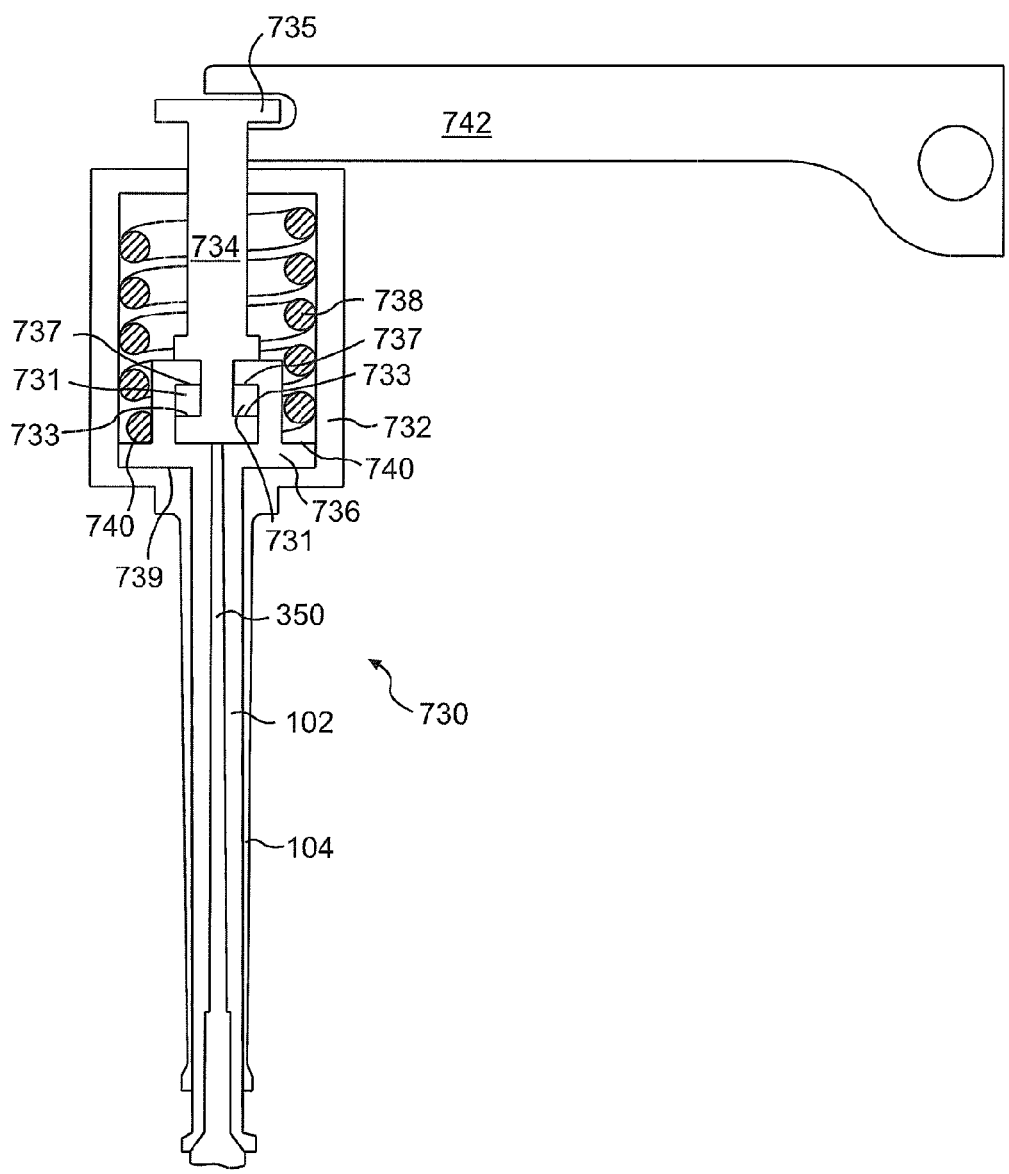
FIG. 45 is a cutaway view of a single-spring, single-cam actuator in accordance with the present invention.

Referring now to FIG. 45, there is shown a cutaway view of a single-spring actuator 730 in accordance with the present invention. The single-spring actuator 730 includes a housing 732 connected to outer tube 104 of applicator 100. Located within housing 730 is a first movable portion 734 which is attached to expander 350. Also located within housing 730 is a second movable portion 736 which is attached to inner tube 102. A spring 738 having a predetermined strength is located within housing 732 and mounted to resist upward movement of second movable portion 736 by virtue of contact between upper contact surface 740 of second movable portion 736 and the lower surface of spring 738.

The single-spring actuator 730 of FIG. 45 is shown in the initial state. To go from the initial state to the intermediate state, a proximally directed force is exerted on connection means 735 of first movable portion 734 by any suitable method. The method shown is a lever 742. Initial proximal movement relative to outer tube 104 of connection means 735 will pull only expander 350 proximally since first movable portion 734 moves proximally through chamber 731 until upper contact surface 733 of first movable portion 734 contacts lower contact surface 737 of second movable portion 736. At this point, applicator 100 is in the intermediate state.

To go from the intermediate state to the deployed state, connection means 735 is pulled further proximally causing further proximal movement of first movable portion 734. By virtue of the contact between contact surfaces 733, 737, first movable portion 734 pulls second movable portion 736 proximally relative to outer tube 104 to the deployed state thereby compressing spring 738 by virtue of surface 740. Second movable portion 736 is, in turn, connected to inner tube 102 and thus the proximal movement of second movable portion 736 causes proximal movement of inner tube 102 relative to the outer tube 104 (which is mounted to housing 732). The deployed state is reached when either the proximal force on pull rod 742 equalizes with the distal force exerted by spring 738, the spring is fully compressed, or a stop is reached.

To return from the deployed state to the final state, connection means 735 is returned to its distal position, either by an external force or by removing the proximal force. In a preferred embodiment, surface 739 of second movable portion 736 returns to its original position in contact with housing 732 by way of the distal force supplied by spring 738 acting upon surface 740. In this way, surfaces 733 and 737 maintain contact and first movable portion 734 and second movable portion 736, and correspondingly expander 350 and inner tube 102, return to the intermediate state in unison. Continued distal movement of connection means 735 under an external force causes first movable portion 734 to move through chamber 731 in second movable portion 736 until first movable portion contacts surface 740, at which point expander 350 and inner tube 102 are restored to their original positions. The relative distances moved by expander 350 and inner tube 102 are set by the relative locations of the contact surfaces involved.

Activation Mechanism

As discussed above, connector 200 is deployed via two systems, the activation mechanism and the drive mechanism or actuator. The activation mechanism translates an input energy into a motion that drives the drive mechanism. The input energy may be any type known to one skilled in the art, and can include mechanical, hydraulic, pneumatic, electrical, or any other suitable energy. Preferably, the activation mechanism translates the input energy into either a pulling motion or a pulling and then a releasing motion that drives the drive mechanism. Different types of activation mechanisms are depicted graphically in FIGS. 46-51. Specific embodiments of activation mechanisms or handles are depicted in FIGS. 52-54 and 55-58.

Referring now to FIGS. 46A-46D, there is shown a spring driven activator 400 for providing the required movements to expander 350 using a cable 402 connected to the proximal end of expander 350 using, for example, a threaded screw 338. In the ready state of FIG. 46A, a compression spring 404 is connected to cable 402. Compression spring 404 is under compression against surface 406 on one side, and is held under compression by first motion switch 408 holding cable 402 in position by any suitable mechanical means. The entire activator 400 may be anchored in a fixed position at 410.

Figure 46A:
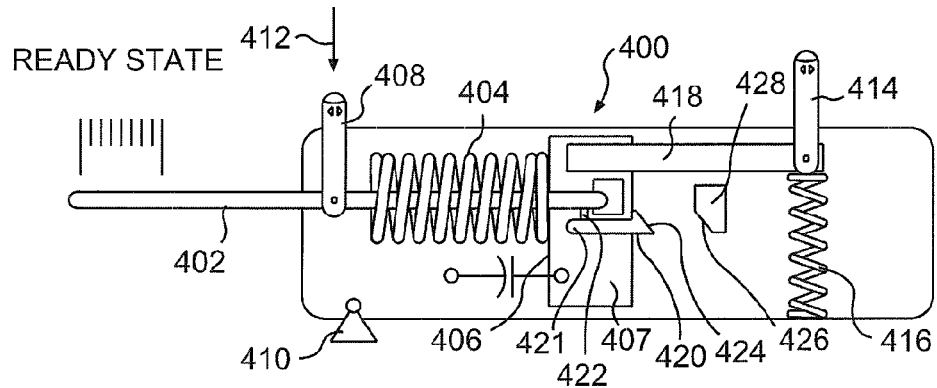
FIGS. 46A-46D are four cutaway views showing the movements of one embodiment of an actuator which pulls against a spring in accordance with the present invention.
Figure 46B:
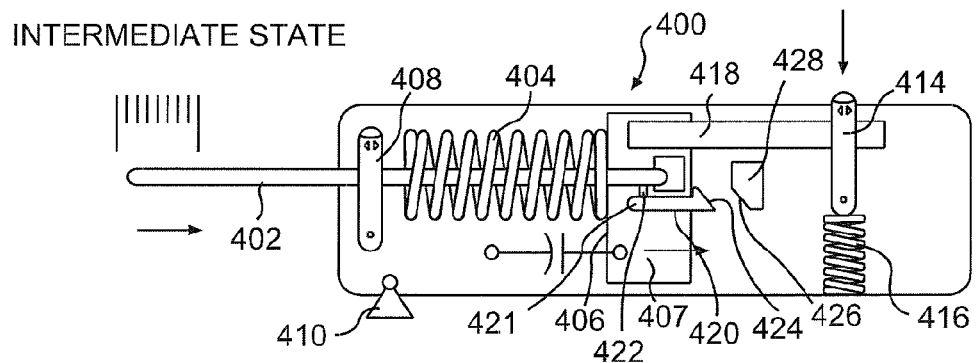

To go from the initial state of FIG. 46A to the intermediate state of FIG. 46B and thereby cause expansion of inner tube 102, the user depresses first motion switch 408 in the direction of arrow 412 of FIG. 46A from the position shown in FIG. 46A to the position shown in FIG. 46B. Depression of first motion switch 408 releases cable 402 to permit the force of compression spring 404 to pull cable 402 a limited distance proximally as shown in FIG. 46B. Once the forces equalize, proximal motion stops and activator 400 reaches the intermediate state of FIG. 46B. To go from the intermediate state to the release state, second motion switch 414 is depressed against spring 416 as shown in FIG. 46B to release the force on surface 406 and thereby permit compression spring 404 to pull cable 402 further proximally to the position shown in FIG. 46C. Second motion switch 414 achieves this by restricting the motion of bar 418 until second motion switch 414 is depressed. Second motion switch 414 returns to its original position in the release state shown in FIG. 46C by virtue of the action of spring 416 for the purpose of locking bar 418 in a fixed position.

Figure 46C:
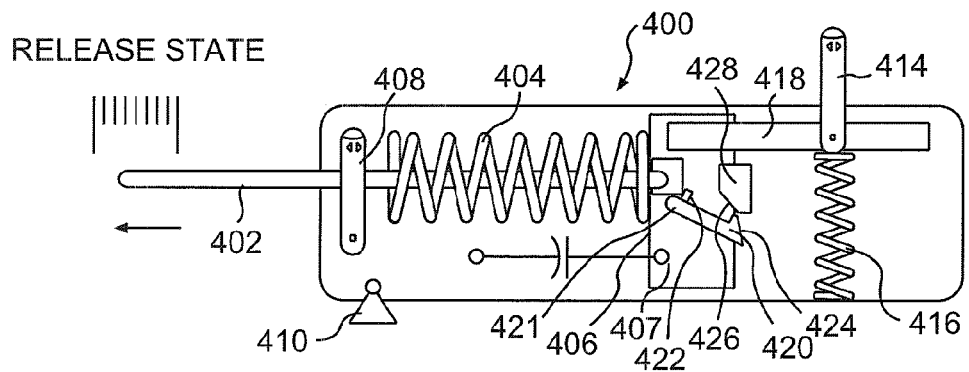
Figure 46D:
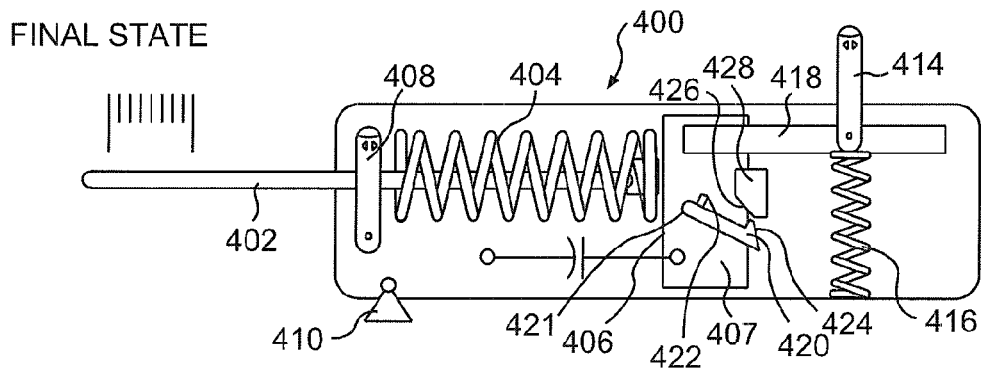

Cable 402 is then released back to the final state by the action of release mechanism 420. More specifically, release mechanism 420 is pivotally connected to plate 407 at pivot point 421. Release mechanism 420 is also attached to cable 402 by protrusion 422 as shown in FIG. 46A. Release mechanism 420 includes an inclined surface 424 which interacts with inclined surface 426 of mechanical stop 428 as shown in FIG. 46C to cause protrusion 422 to release cable 402 and allow cable 402 to return to the final state shown in FIG. 46D, at which point expander 350 and inner tube 102 return to their original positions.

Figure 47A:
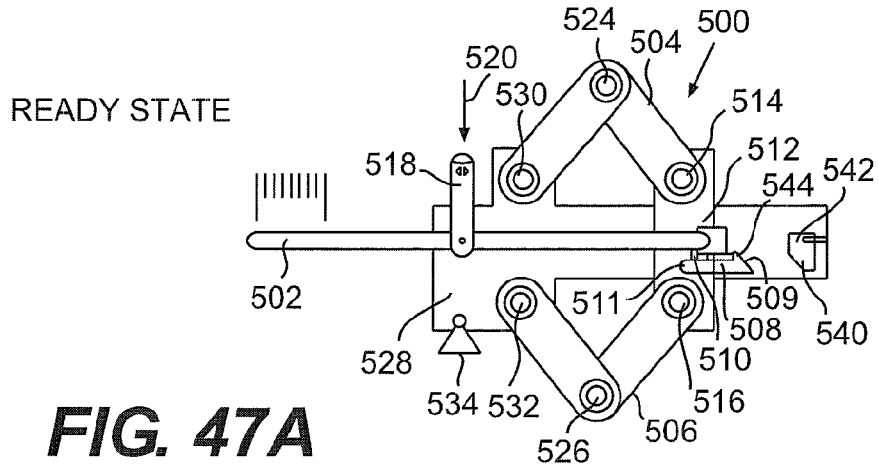
FIGS. 47A-47C are three cutaway views showing the movements of another embodiment of an actuator which employs hinged arms in accordance with the present invention.
Figure 47B:
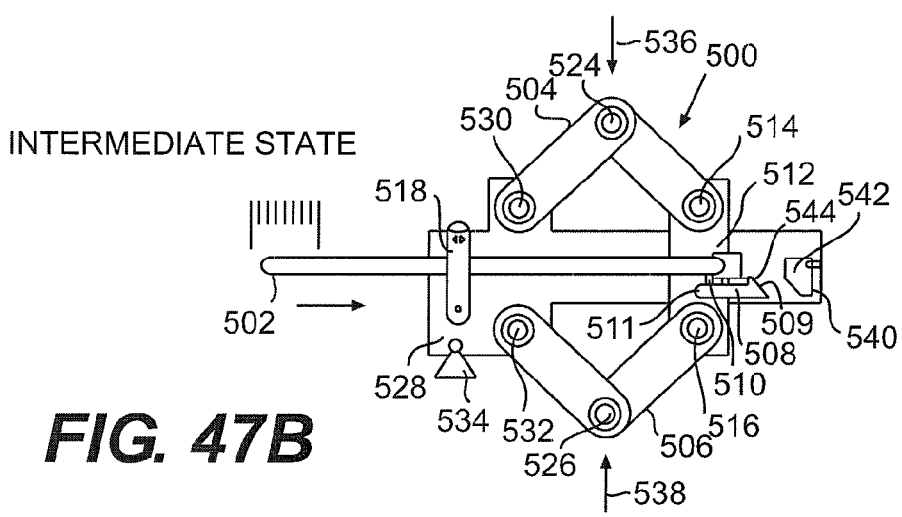
Figure 47C:
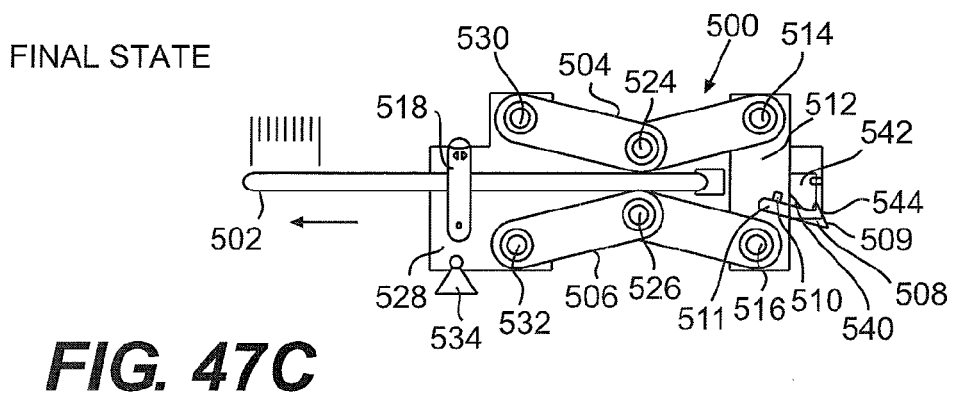

Referring now to FIGS. 47A-47C, there is shown another embodiment of an activator 500 which employs two hinged arms 504 and 506 to generate the required motion of expander 350 using a cable 502 connected to the proximal end of expander 350 by, for example, a threaded screw 338. In this embodiment, cable 502 is held under tension by hinged arms 504, 506 in the ready state via the connection of release mechanism 508 to cable 502 via protrusion 510, and the pivotal connection of release mechanism 508 to piston 512 at pivot point 511. Piston 512 is, in turn, pivotally connected to hinged arms 504, 506 by pivotal connections 514, 516. Hinged arms 504, 506 also include pivotal connections 524 and 526 and are also pivotally connected to a fixed housing 528 by pivotal connections 530, 532. Housing 528 may be fixed at anchor point 534.

First motion switch 518 holds cable 502 in position in the initial state of FIG. 47A. Depression of first motion switch 518 in the direction of arrow 520 of FIG. 47A releases cable 502 and allows the tension exerted by hinged arms 504, 506 to pull cable 502 a short distance proximally to the intermediate state of FIG. 47B.

To go from the intermediate state of FIG. 47B to the final state of FIG. 47C, force is exerted at pivotal connections 524 and 526 in the direction shown by arrows 536, 538 in FIG. 47B either directly by the user or via a suitable mechanical, electrical or other device which can be actuated by the user. The exertion of force at pivotal connections 524, 526 causes hinged arms 504, 506 to fully extend to the position shown in FIG. 47C. Initially, extension of hinged arms 504, 506 pulls cable 502 further proximally until inclined surface 509 of release mechanism 508 contacts inclined surface 540 of stop mechanism 542. At that point, release mechanism 508 is caused to disengage from cable 502, at which point cable 502 returns to its original position shown in FIG. 47C. In this embodiment, release mechanism 508 also includes a lock mechanism 544 which engages with stop mechanism 542 as shown in FIG. 47C to prevent piston 512 from moving distally to its original position when cable 502 moves distally.

Figure 48A:
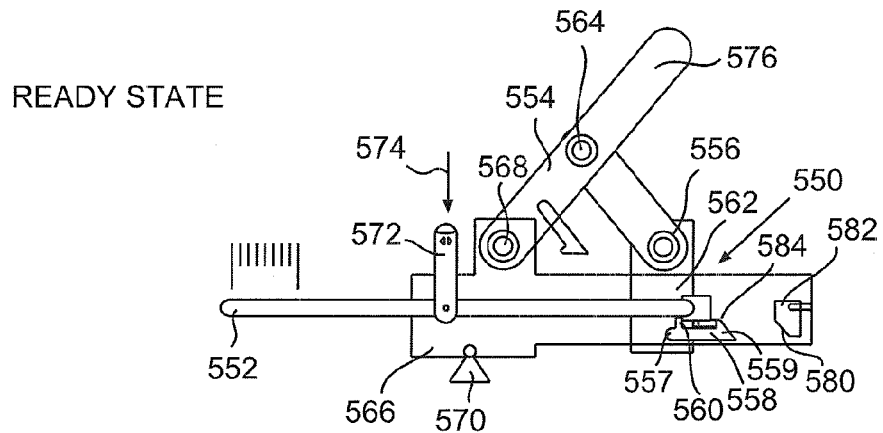
FIGS. 48A-48C are three cutaway views showing the movements of an embodiment of an actuator which employs a hinged arm in accordance with the present invention.
Figure 48B:
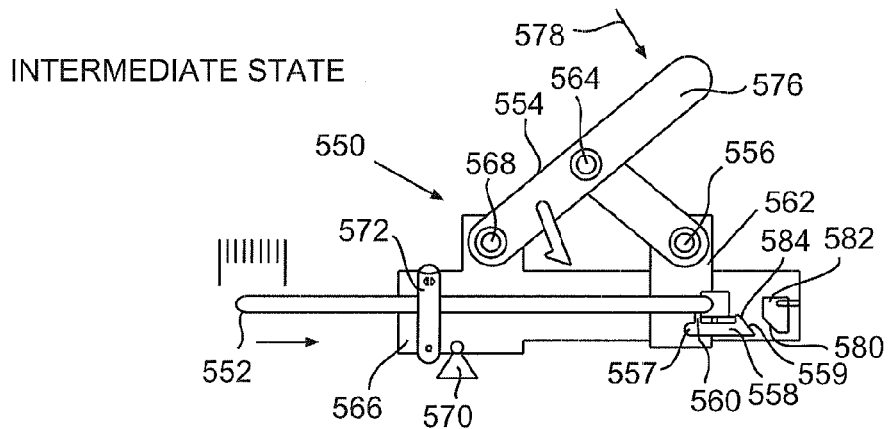
Figure 48C:
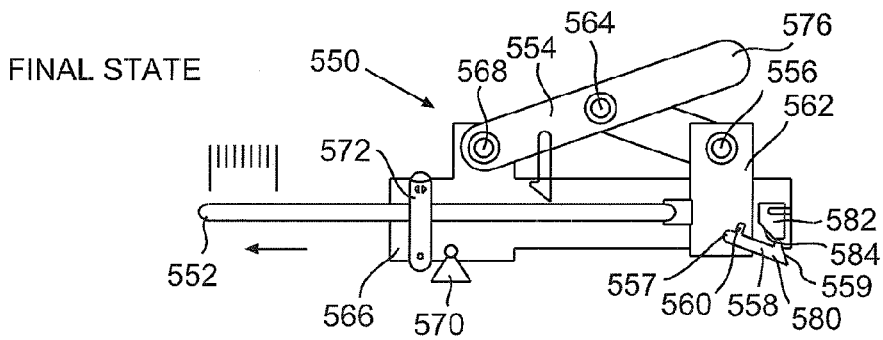

Referring now to FIGS. 48A-48C, there is shown yet another embodiment of an activator 550 in accordance with the present invention which employs a single hinged arm to generate the required motion of expander 350 by virtue of pulling a cable 552 which may be connected to the proximal end of expander 350 by, for example, a threaded screw 338. In this embodiment, cable 552 is held under tension by hinged arm 554 in the ready state via the connection of release mechanism 558 to cable 552 via protrusion 560, and the pivotal connection of release mechanism 558 to piston 562 at pivot point 557. Piston 562 is, in turn, pivotally connected to hinged arm 554 by pivot 556. Hinged arm 554 also includes pivot 564 and is also pivotally connected to housing 566 at pivot 568. Housing 566 may be fixed at anchor point 570.

First motion switch 572 holds cable 552 in position in the initial state of FIG. 48A. Depression of first motion switch 572 in the direction of arrow 574 of FIG. 48A releases cable 552 and allows the tension exerted by hinged arm 554 to pull cable 552 a short distance proximally to the intermediate state of FIG. 48B.

To go from the intermediate state of FIG. 48B to the final state of FIG. 48C, force is exerted on arm extension 576 of hinged arm 554 in the direction of arrows 578 in FIG. 48B either directly by the user or via a suitable mechanical, electrical or other device which can be actuated by the user. The exertion of force on arm extension 576 causes hinged arm 554 to extend to the position shown in FIG. 48C. Initially, extension of hinged arm 554 pulls cable 552 further proximally until inclined surface 559 of release mechanism 558 contacts inclined surface 580 of stop mechanism 582. At that point, release mechanism 558 is caused to disengage from cable 552, at which point cable 552 returns distally to the position of the final state shown in FIG. 48C. In this embodiment, release mechanism 558 also includes a lock mechanism 584 which engages with stop mechanism 582 as shown in FIG. 48C to prevent piston 562 from moving back distally to its original position when cable 552 moves distally to the final state.

Referring now to FIGS. 49A-49D, there is shown another embodiment of an activator 600 in accordance with the present invention which employs a freewheel 604 to generate the required motion of expander 350 by virtue of pulling a cable 602 which may be connected to the proximal end of expander 350 by, for example, a threaded screw 338. In this embodiment, cable 602 is held under tension to freewheel 604 in the ready state via the connection of release mechanism 608 to cable 602 via protrusion 610, and the pivotal connection of release mechanism 608 to freewheel 604 at pivot point 606. Freewheel 604 is biased to rotate in a clockwise direction in FIGS. 49A-49D by, for example, a spring (not shown).

Figure 49A:
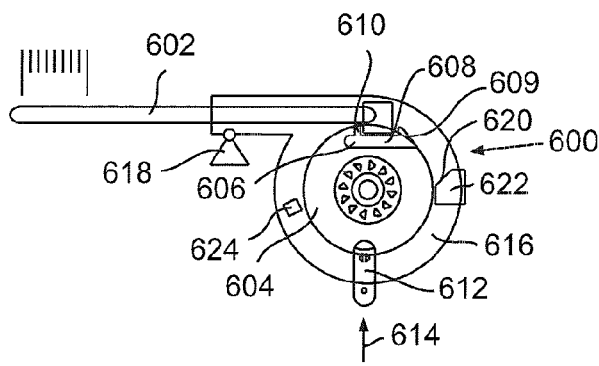
FIGS. 49A-49D are four cutaway views showing the movements of an embodiment of an actuator which pulls a cable in accordance with the present invention.

Freewheel 604 is initially held in position by motion switch 612 in the initial state of FIG. 49A by engagement of the ready switch 612 with both freewheel 604 and housing 616. Housing 616 may be fixed by anchoring it at anchor point 618. Depression of motion switch 612 in the direction of arrow 614 of FIG. 49A releases cable 602 and allows the tension exerted by spring-loaded freewheel 604 to pull the cable 602 a short distance proximally to the intermediate state of FIG. 49B by rotation of freewheel 604 in a clockwise direction.

Figure 49B:
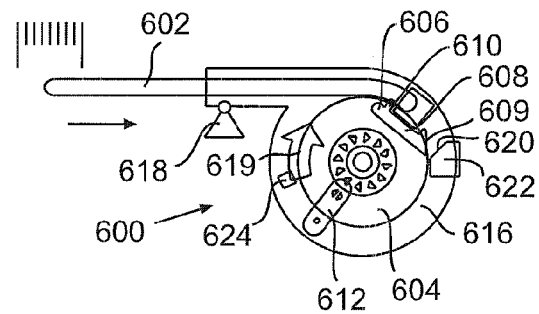
Figure 49C:
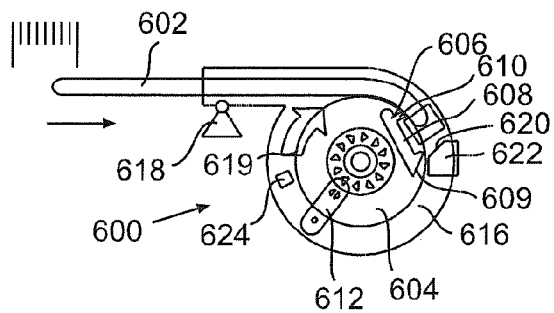

To go from the intermediate state of FIG. 49B to the release state of FIG. 49C, force is exerted by the user on freewheel 604 in the direction of arrow 619 of FIG. 49B to cause further clockwise rotation of freewheel 604 to the release state of FIG. 49C to thereby cause cable 602 to move further proximally. Force 619 can be exerted either directly by the user or via a suitable mechanical, electrical or other device which can be actuated by the user.

Figure 49D:
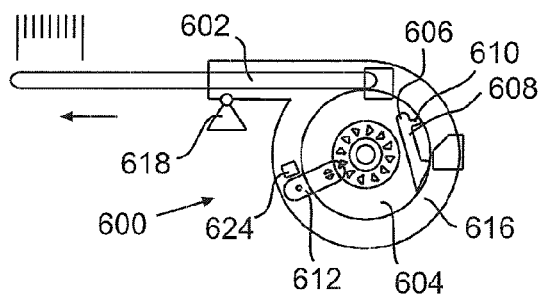

To go from the release state of FIG. 49C to the final state of FIG. 49D, the user continues to exert force in the direction of arrow 619 to cause further clockwise rotation of freewheel 604. Further rotation of freewheel 604 causes inclined surface 609 of release mechanism 608 to contact inclined surface 620 of stop mechanism 622. At that point, release mechanism 608 is caused to disengage from cable 602 by pivoting about pivot point 610 at which point cable 602 returns distally to the position of the final state shown in FIG. 26D. In this embodiment, housing 616 preferably includes a mechanical stop 624 to prevent motion switch 612 and thus freewheel 604 from rotating in a clockwise direction beyond the position reached in the final state of FIG. 49D.

Figure 50A:
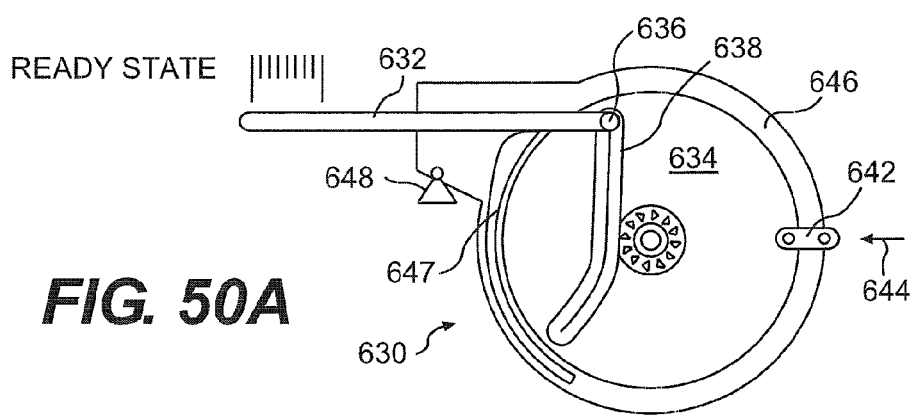
FIGS. 50A-50C are three cutaway views showing the movements of a cam-operated actuator in accordance with the present invention.
Figure 50B:
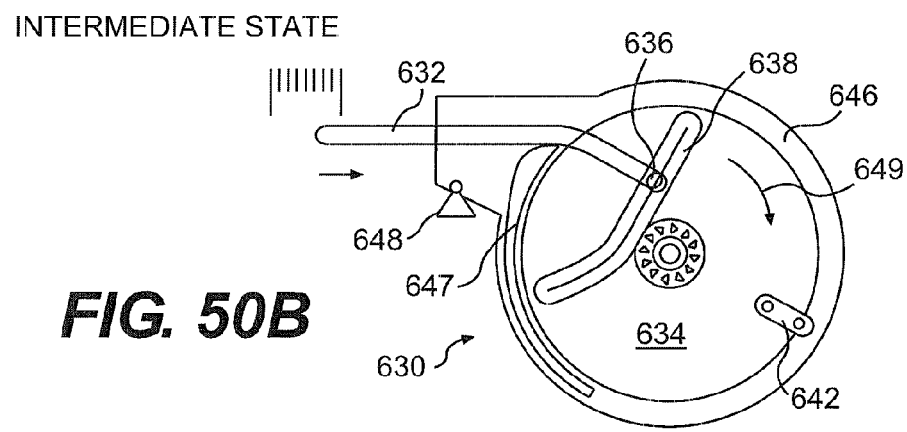
Figure 50C:
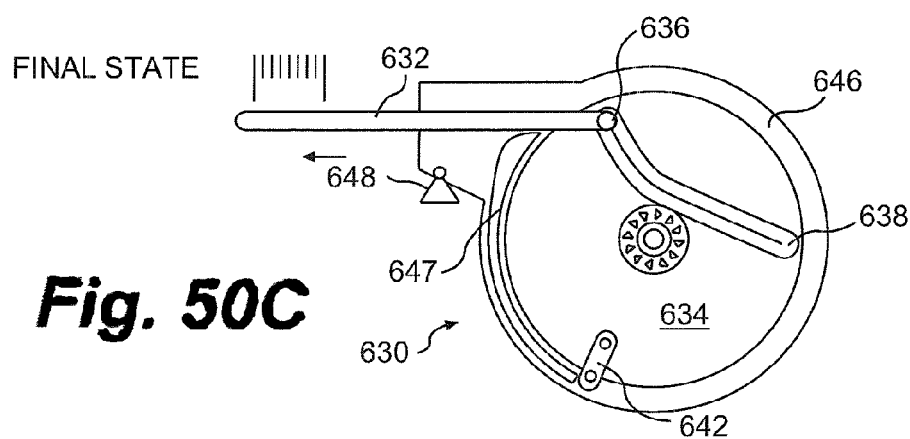

Referring now to FIGS. 50A-50C, there is shown another embodiment of an activator 630 in accordance with the present invention which employs freewheel 634 to generate the required motion of expander 350 by virtue of pulling cable 632 which may be connected to the proximal end of expander 350 by, for example, a threaded screw 338. In this embodiment, cable 632 is held under tension to freewheel 634 in the initial state via the connection of cable 632 to cam follower 636 located in cam 638 of freewheel 634. Freewheel 634 is biased to rotate in a clockwise direction in FIGS. 50A-50C by, for example, a spring (not shown).

Freewheel 634 is held in position by motion switch 642 in the initial state of FIG. 50A by engagement of motion switch 642 with both freewheel 634 and housing 646. Housing 646 may be fixed by anchoring it at anchor point 648. Depression of motion switch 642 in the direction of arrow 644 of FIG. 50A releases cable 632 and allows the tension exerted by spring-loaded freewheel 634 to pull cable 632 a short distance proximally to the intermediate state of FIG. 50B by rotation of freewheel 634 in a clockwise direction as shown by arrow 649. Rotation of freewheel 634 pulls cable 632 by movement of cam follower 636 in cam 638 of rotating freewheel 634. The initial movement of the cam follower 636 in cam 638 pulls cable 632 over mechanical stop 647 which is attached to housing 646, thereby moving cable 632 a short distance proximally as shown in FIG. 50B.

To go from the intermediate state of FIG. 50B to the final state of FIG. 50C, cam follower 636 reaches a point shown in FIG. 50B where the tension on cable 632 will cause cam follower 636 to continue movement along cam 638 and cause further rotation of freewheel 634 in a clockwise direction to the position of FIG. 50C. Due to the nature of cam 638, cable 632 returns to the final state shown in FIG. 50C by the action of cam follower 636 following cam 638. Mechanical stop 647 extends downwardly as shown in the figures to prevent motion switch 642, and thus freewheel 634, from rotating in a clockwise direction beyond the position reached in the final state of FIG. 50C.

Referring now to FIGS. 51A-51D, there is shown another embodiment of an activator 650 in accordance with the present invention which employs a freewheel 654 to generate the required motion of expander 350 by virtue of pulling a cable 652 which may be connected to the proximal end of expander 350 by, for example, a threaded screw 338. In this embodiment, cable 652 is held under tension to freewheel 654 in the initial state via the connection of cable 652 directly to freewheel 654 by a pivotal connection 656. Freewheel 654 is biased to rotate in a clockwise direction in FIGS. 51A-51D by, for example, a spring (not shown).

Freewheel 654 is initially held in position by motion switch 662 in the ready state of FIG. 51A by engagement of motion switch 662 with both freewheel 654 and housing 666. Housing 666 may be fixed by anchoring it at anchor point 668. Depression of motion switch 662 in the direction of arrow 664 of FIG. 51A releases cable 652 and allows the tension exerted by spring-loaded freewheel 654 to pull cable 652 a short distance proximally to the intermediate state of FIG. 51B by rotation of freewheel 654 in a clockwise direction as shown by arrow 669. Rotation of freewheel 654 pulls cable 652 by movement of pivotal connection 656 of rotating freewheel 654. The initial movement of pivotal connection 656 pulls cable 652 a short distance proximally as shown in FIG. 51B.

To go from the intermediate state of FIG. 51B to the release state of FIG. 51C, further rotation of freewheel 654 causes pivotal connection 656 to reach a point shown in FIG. 51C where cable 652 moves distally and returns to the final state shown in FIG. 51D. Mechanical stop 667 prevents motion switch 662, and thus freewheel 654, from rotating in a clockwise direction beyond the position reached in the final state of FIG. 51D.

In addition to the embodiments described schematically in FIGS. 46-51, a rack and pinion and extension spring system may be employed to pull on a cable or pulling tube 350. In this embodiment, the cable or pulling tube 350 is pivotally attached to a lever, which, in turn, is pivotally attached to a rack that is housed within a housing. A spring-loaded pinion is rotatably mounted to the housing and is provided with pinion teeth for engagement of the rack. The pinion may be held in the initial position by any suitable mechanical or electrical actuation device. To operate such a rack and pinion device, the pinion is initially held in a first position. The pinion is released, whereupon the pinion 832 rotates and pulls the rack which, in turn, causes the cable or pull tube to move proximally to expand the inner tube 102 and then compress connector 200. The pinion continues to rotate until the pinion teeth disengage from the teeth of rack, thereby allowing the rack and thus the cable or pull tube 350 to return to its initial position. A return spring may be provided on the rack to help return the rack to its original position.

Shape Memory Mechanism

In addition to the embodiments described above, an activator can be designed using shape memory alloys. Shape memory alloys may be made from nickel and titanium, an example being Nitinol. These alloys have a unique ability to contract when heated. The shape memory alloys return to their original state upon cooling to room temperature. The contractibility allows the shape memory alloy wires to exert a force that can be exploited to drive one of the mechanisms described above, or to drive the pull tube and inner tube directly. For example, a shape memory alloy wire or an array of shape memory alloy wires could be directly attached to each of the inner and pull tubes. Electrical means could be used to heat the shape memory alloy material. The resultant decrease in the length of the shape memory alloy of the wires would then be employed to independently drive the movements of the inner and pull tubes, including the movement required for deformation of the staple elements of the connector. Since the shape memory alloy wires return to their original length upon cooling, no additional means is required to return the inner and pull tubes to their original position once anastomosis is complete. One potential advantage of the shape memory alloy activator, is that it would permit a miniaturized or compact activator that could be suitable for use, for example, in endoscopic procedures.

Handles

Figure 52B:
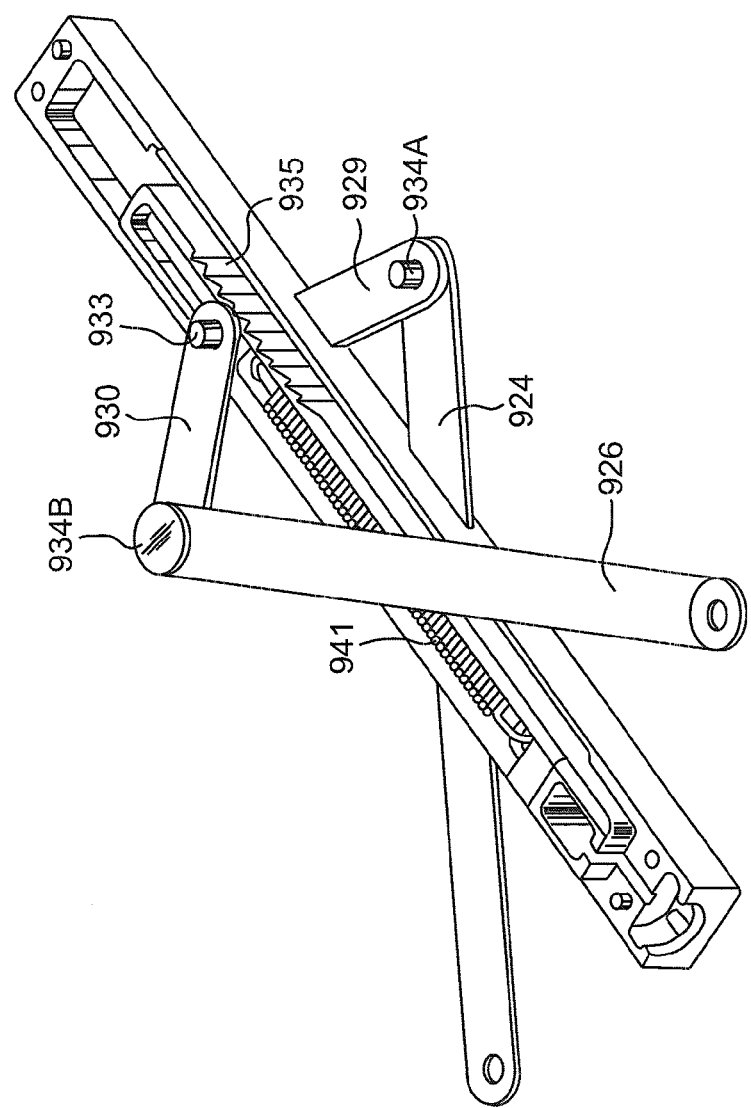
Figure 52C:
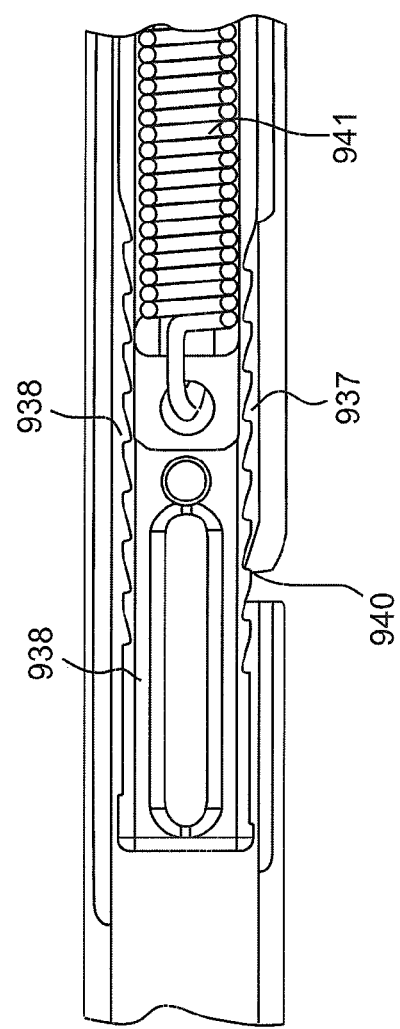
Figure 53:
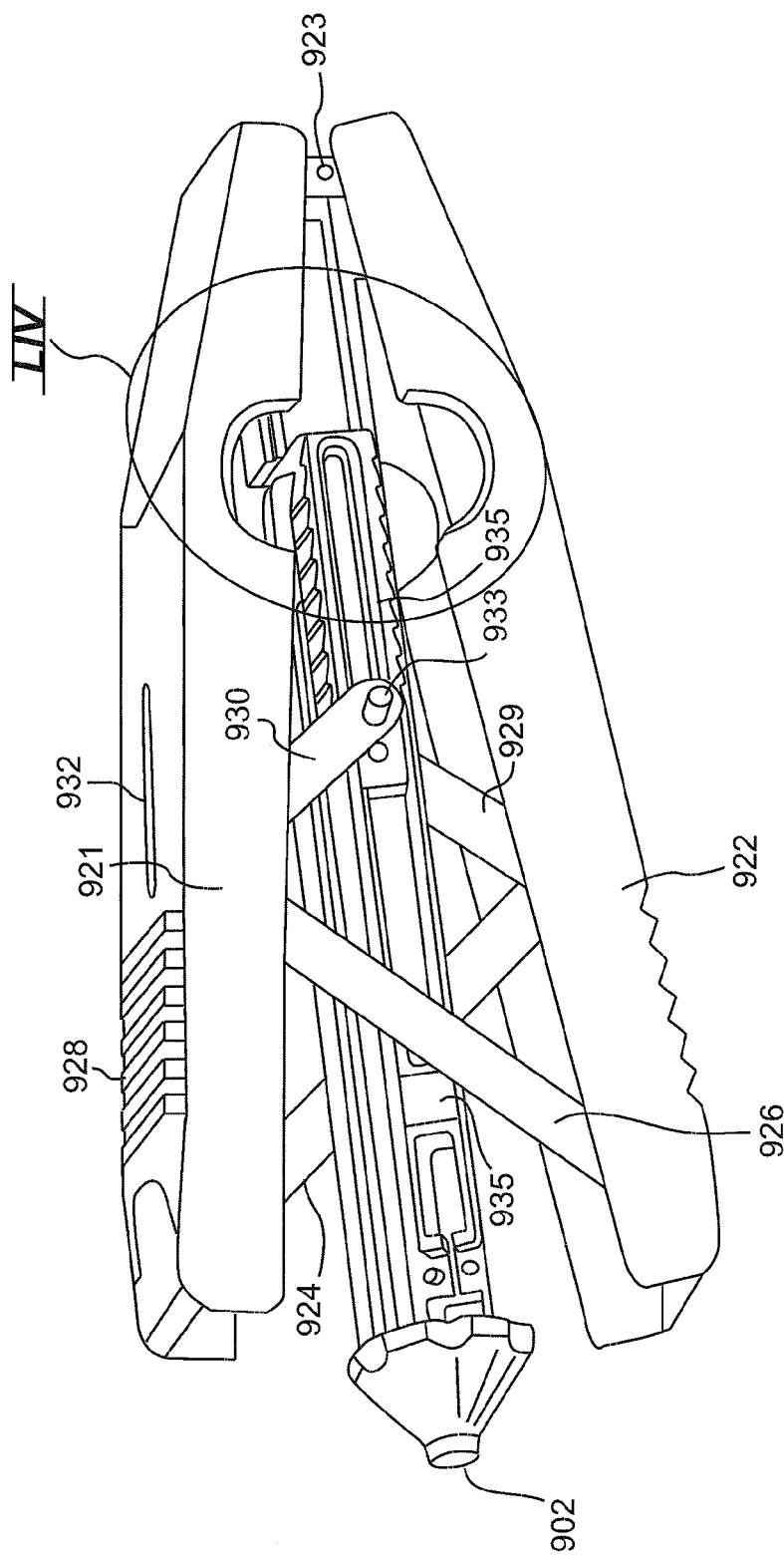
FIG. 53 is another perspective view of the handle portion of FIGS. 52A-52B with the side cover of the housing removed to expose some of the internal parts.

Referring to FIGS. 52-54, there is shown details of a handle portion 920 of activator 900 or 901 (FIGS. 1-2). Handle portion 920 of this embodiment has the advantage that it provides direct, positive feedback to the user indicative of the motions of front-end portion 960. As a result, the user has more control of the process and can be informed of the current state of the anastomosis by handle portion 920.

Handle portion 920 includes two grips 921, 922 hingedly attached to one another at the rear 923 of handle portion 920. Handle portion 920 can be fabricated to any suitable size but is preferably fabricated such that grips 921, 922 can each be actuated by pressure exerted by the hand of the user. As a result, squeezing grips 921, 922 of handle portion 920 between the thumb and the middle and index finger of the user can actuate handle portion 920. Grips 921, 922 may include a roughened or textured portion 928 on the surface thereof to facilitate gripping by the user.

As seen in FIGS. 52A-52B grip 921 has a linkage 924 fixedly connected to grip 921 by a pivotal connection 925 which allows linkage 924 to pivot relative to grip 921. Grip 922, has a linkage 926 fixedly connected to grip 922 by a pivotal connection 927 which allows linkage 926 to pivot relative to grip 922. Referring to FIG. 52B, linkage 924 connects to a sliding join 934a with linkage 929 and linkage 926 connects to a sliding join 934b with linkage 930. The sliding join 934a between linkage 924 and linkage 929 is mounted for sliding movement in a slot 931 of grip 922. Similarly, the sliding join 934b between linkage 926 and linkage 930 is mounted for sliding movement in a slot 932 (FIG. 53) of grip 921.

The mounting of sliding linkages in slots 931, 932 provides two advantages for handle portion 920. First, the movement of sliding linkages in slots 931, 932 provides direct feedback to the user indicating the extent of movement of the applicator 100 and/or expander 300 or 350 since the user can view or feel the position of the sliding linkages in slots 931, 932 while using the activator 900 or 901. Second, the connection of linkages 924, 926, 929 and 930 to both grips 921, 922 helps to ensure that both sets of linkages move together at the same pace to provide a consistent motion of the various moving parts of activator 900. Such a movement is ensured because the connection of linkages 924, 926, 929 and 930 to both grips 921, 922 require that grips 921, 922 move together simultaneously and will thereby substantially prevent movement of one of grips 921, 922 without corresponding movement of the other of grips 921, 922.

Referring to FIG. 52B, linkages 929, 930 are mounted on a slidable linkage 933, which also requires linkages 929, 930 to move together as a unit. Slidable linkage 933 is fixedly mounted in rear shuttle 935. Handle portion 920 includes a front shuttle 936 in addition to rear shuttle 935. Rear and front shuttles 935, 936 together form a reciprocating element which is capable of reciprocating motion within handle portion 920. Front shuttle 936 is connected to rear shuttle 935 by a spring 941 which permits a slight separation between front shuttle 936 and rear shuttle 935 for the purpose of absorbing slack in the system. In this manner, a smooth even pull of cable or pull tube 352 can be ensured even though handle portion 920 may be connected via a flexible connection 903 to front-end portion 960.

Handle portion 920 may also include a leaf spring ratchet as shown in FIG. 52C connected to spring 941 and composed of a track 937 and an engagement device 938 which rides in track 937 to ensure one-way movement of the cable or pull tube. Engagement device 938 of the leaf spring ratchet is located in a fixed position except that engagement device 938 has the ability to move up and down to slide along track 937. As the rear shuttle portion 935 slides proximally as shown in FIGS. 53-54, track 937, which is part of rear shuttle portion 935, also slides proximally allowing engagement device 938 to ride up slopes 939 of track 937 until engagement device 938 reaches the proximal-most edge of the next slope 939 and drops into one of the slots 940 of track 937. The dropping of engagement device 938 into a slot 940 in track 937 prevents the rear shuttle 935 from moving distally during the anastomosis procedure and thus prevents a reversal of the motion of cable or pull tube 352 in the middle of the procedure in the event the user stops the application of force to handle portion 920 for any reason. This ratchet feature allows the user to hand handle portion 920 to another person during the procedure, for example.

Handle portion 920 is connected via connection 902, 903 to front-end portion 960 as shown in either FIG. 1 or FIG. 2. A cable 950, shown in FIG. 36, connects front shuttle 936 of handle portion 920 to cam 961 of front-end portion 960. As shown in FIG. 36, cable 950 is positioned inside a slot 962 in cam 961 in such a manner that pulling on cable 950 will cause rotation of cam 961 through an arc of preferably about 100 degrees. The end 951 of cable 950 is fixed in hole 963 in cam 961. This arrangement allows remote actuation of front-end portion 960 by handle portion 920 in, for example, the embodiment of FIG. 2.

Figure 55A:
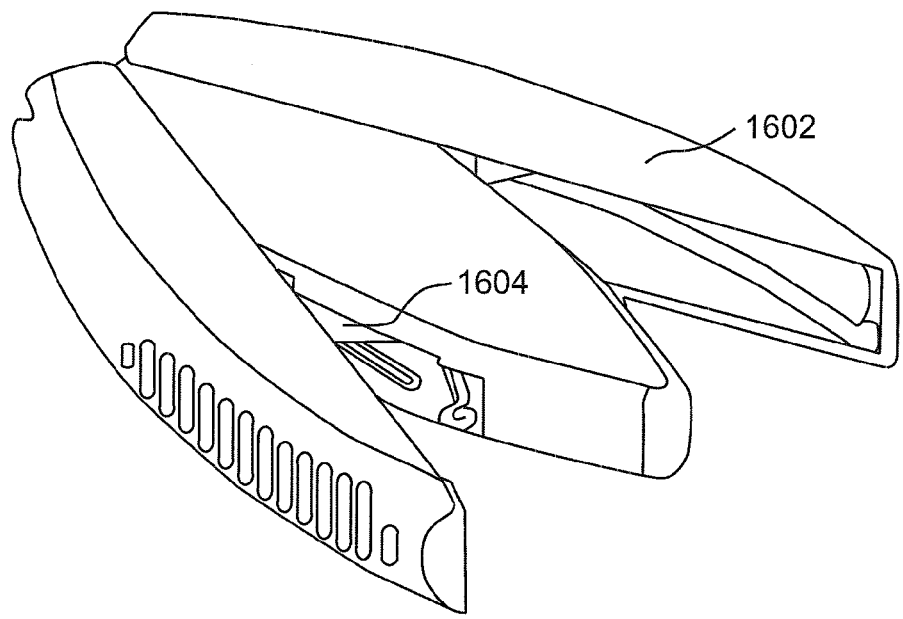
FIGS. 55A-55B depict an isometric view of an alternative embodiment of a squeeze and release actuator in accordance with the invention.
Figure 55B:
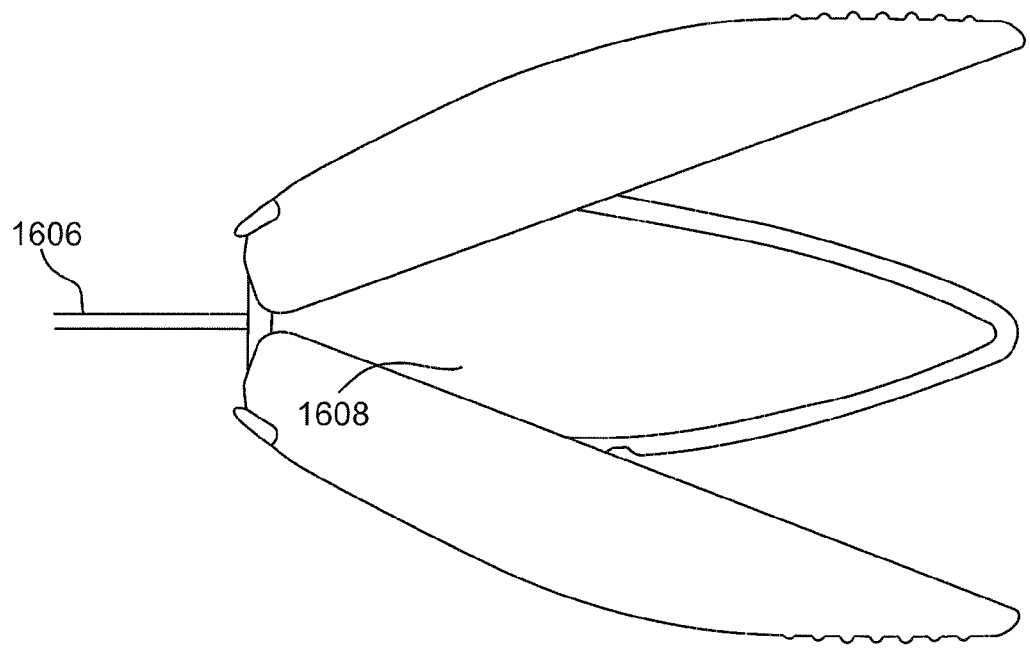
Figure 56A:
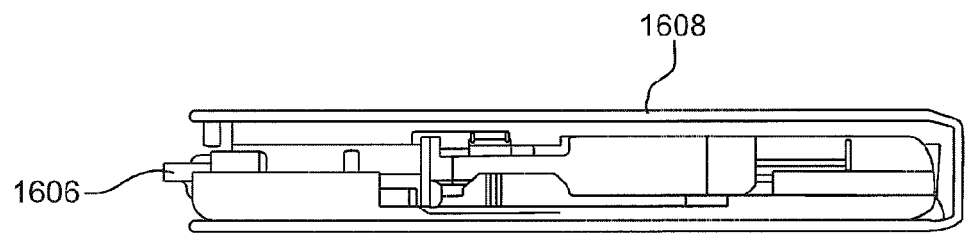
FIGS. 56A-56E depict the internal parts of the actuator of FIGS. 55A-55C
Figure 56B:
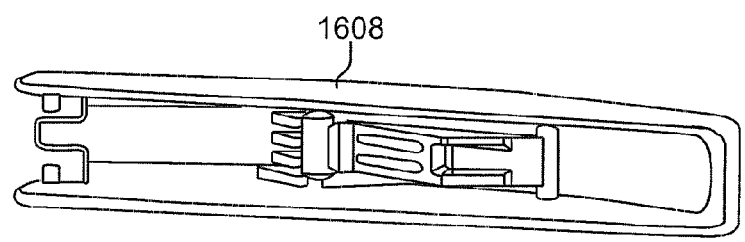
Figure 56C:
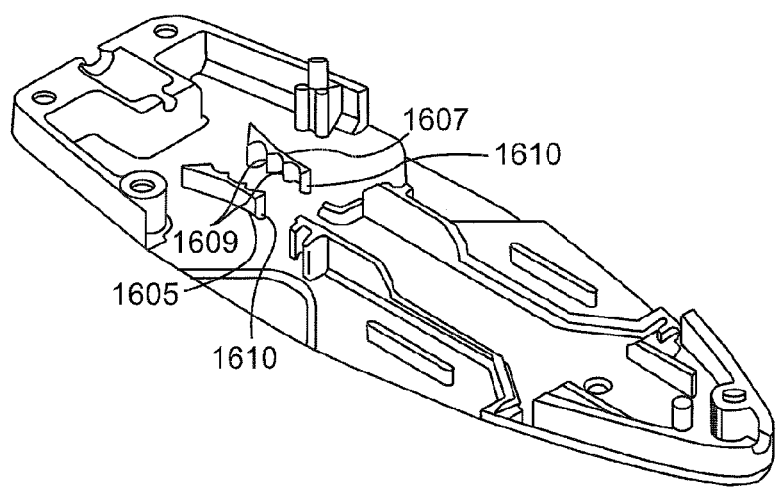
Figure 56D:
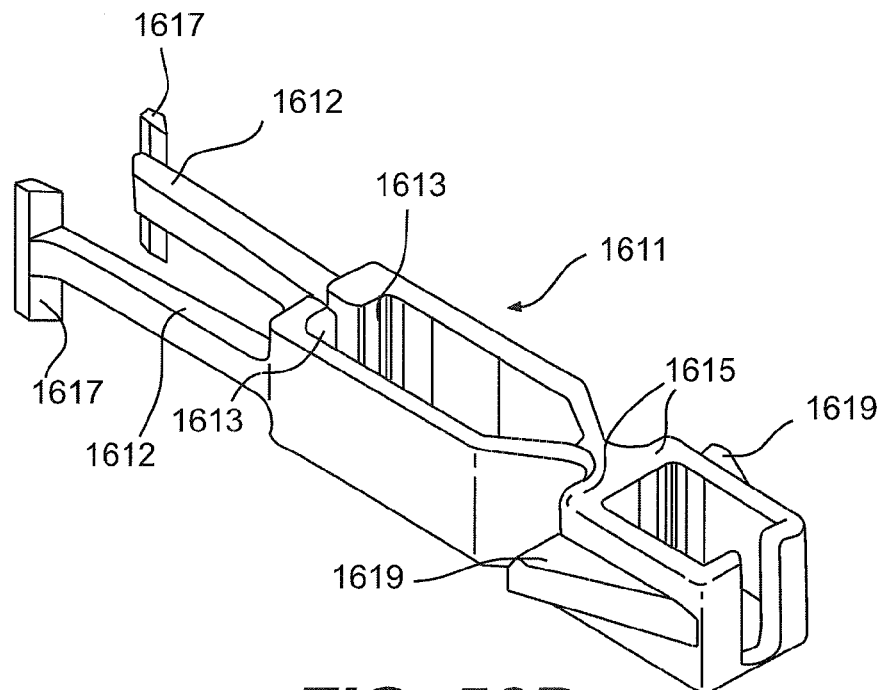
Figure 56E:
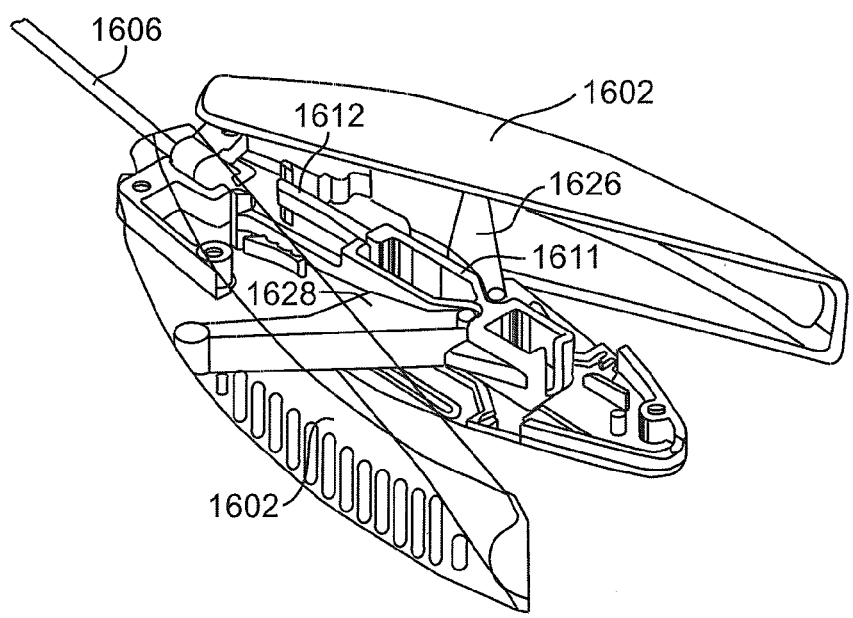

Referring now to FIGS. 55A-55B, there is shown an alternative embodiment of an activator 1600 which employs a squeeze and release design. As shown in FIGS. 55A-55B, activator 1600 includes a lever 1602, a link 1604, a sheath 1606 and a housing 1608. The interior parts of activator 1600 of FIGS. 55A-55B are shown in FIGS. 56A-56E.

The handle of activator 1600 is designed for actuation by a single squeeze and release to accomplish all of the necessary motions to complete an anastomosis. In a preferred embodiment, activator 1600 is designed for use with a dual-spring mechanism to pull cable 1620 a predetermined distance and then permit cable 1620 to return to its initial position by releasing cable 1620.

Figure 57A:
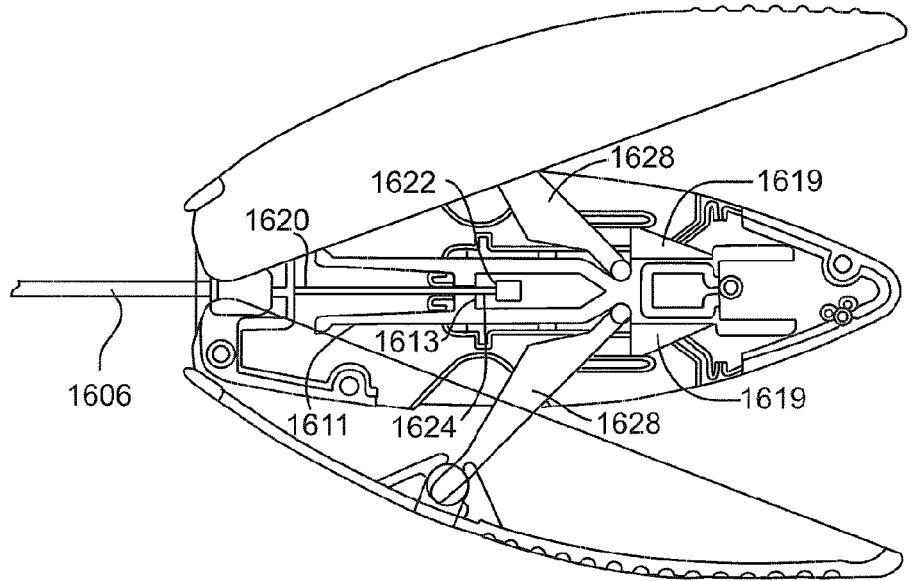
FIGS. 57A-57D depict the movement sequence of the actuator of FIGS. 55A-56E.

Referring to FIG. 57A, which shows the initial position of activator 1600, it can be seen that cable 1620, which extends through sheath 1606, includes a crimp 1622. A gap 1624 exists between crimp 1622 and a surface 1613 of a movable body portion 1611 when activator 1600 is in the initial position of FIG. 57A. The gap 1624 allows for relative motion between the crimp 1622 and surface 1613 that occurs when flexible sheath 1606 is bent during normal use. Bending sheath 1606, which contains cable 1620, causes relative motion between the two components. Gap 1624 prevents the relative motion between the cable 1620 and sheath 1606 from initiating the actuation of the drive mechanism before squeezing the levers 1602 of the handle. Thus, the initial squeeze of levers 1602 closes gap 1624 between surface 1613 and crimp 1622 by the pushing force exerted by links 1626, 1628 against the surface 1615 of body portion 1611 to move body portion 1611 to the position shown in FIG. 57B. As a result of the movement of body portion 1611 proximally from the position of FIG. 57A to the position of FIG. 57B, feet 1617 of legs 1612 of body portion 1611 move relative to ratchet 1610, as shown. Ratchet 1610 prevents body portion 1611 from moving back distally since feet 1617 (FIG. 56D) of body portion 1611 engage with teeth 1609 of ratchet 1610. Once gap 1624 is closed, the pulling force exerted on body portion 1611 will be transferred to cable 1620 via surface 1613 of body portion 1611. Legs 1612 will flex in, and allow feet 1617 to ride on teeth 1609 of ratchet 1610 during closure of levers 1602.

Figure 57B:
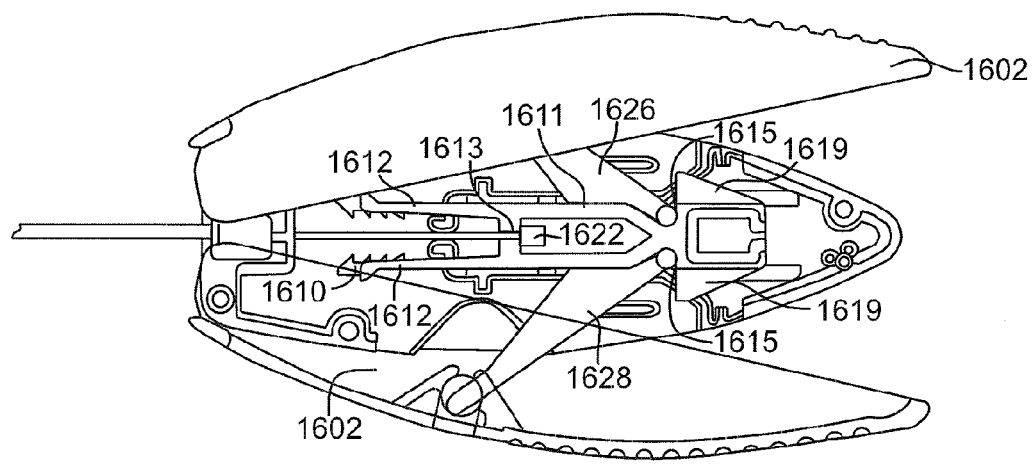
Figure 57C:
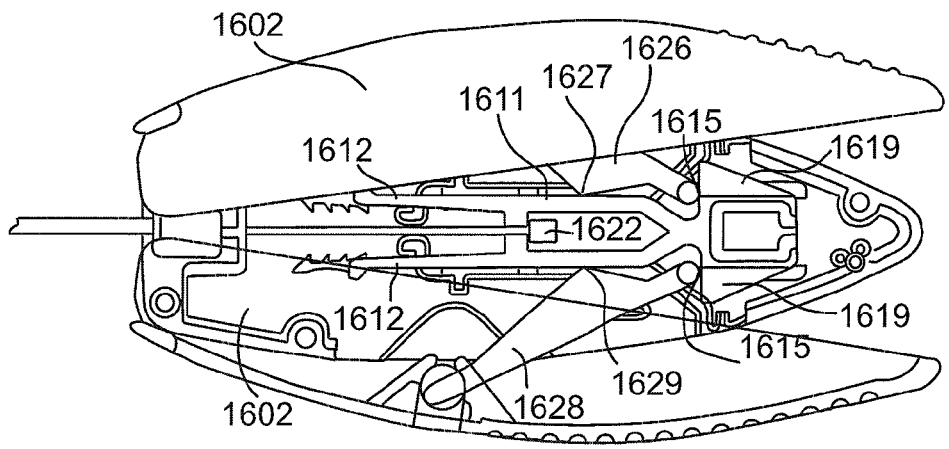

Continuing to squeeze levers 1602 moves activator 1600 from the position shown in FIG. 57B to the position shown in FIG. 57C. During this phase of actuation, fulcrum points 1627, 1629 (FIG. 57C) on links 1626, 1628 engage with body portion 1611 to cause links 1626, 1628 to be deflected from a position parallel to body portion 1611, as shown in FIG. 57B, to a position at an angle to body portion 1611, as shown in FIG. 57C. This deflection of links 1626, 1628 causes links 1626, 1628 to ride up on surface 1615 of fins 1619 of body portion 1611 to an intermediate position shown in FIG. 57C, while at the same time exerting a further force on surface 1615 of body portion 1611 to continue movement of body portion 1611 proximally. Legs 1612 continue to flex inwardly to allow feet 1617 to continue to ride on teeth 1609 of ratchet 1610 during this phase of movement.

Figure 57D:
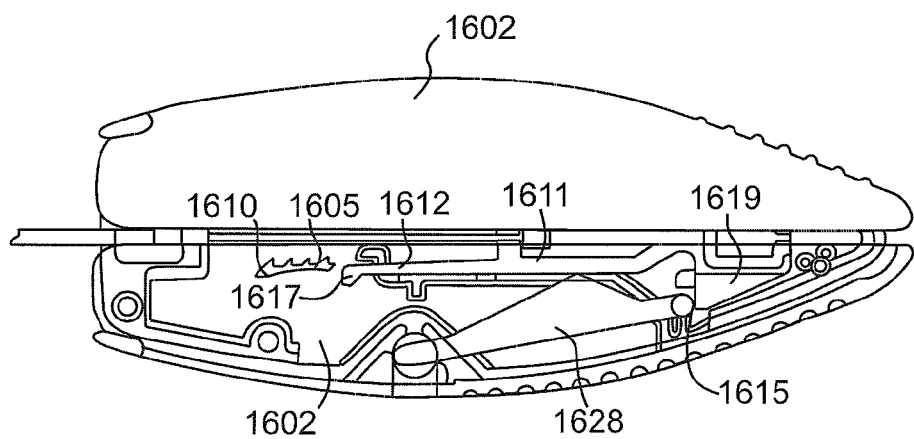

The final phase of actuation causes movement of activator 1600 to the position shown in FIG. 57D. As can be seen from FIG. 57D, body portion 1611 has traveled further proximally from the position shown in FIG. 57C and links 1626 and 1628 have ridden further along surface 1615 of body portion 1611 to allow levers 1602 to be fully closed. In the position of FIG. 57D, legs 1612 and feet 1617 of body portion 1611 have come free of ratchet 1610. Since legs 1612 were biased inwardly by ratchet 1610 while riding in ratchet 1610, once legs 1612 are free of ratchet 1610 they expand freely to a width that exceeds the width of ratchet 1610, as shown in FIG. 57D. This action permits activator 1600 to be returned to the initial position of levers 1602 since feet 1617 of legs 1612 can now ride on smooth outer surfaces 1605, 1607 of ratchet 1610 and thus feet 1617 will not engage with teeth 1609 of ratchet 1610 during the return movement. This permits the user to simply let go of the levers 1602 to release the device.

Return relies on the compression in the sheath 1606 and loads from the front-end mechanism. Specifically, sheath 1606 may be a relatively rigid, but compressible material such that sheath 1606 essentially maintains the spacing between the activator 1600 and a dual-spring mechanism employed to maintain tension on cable 1620. Sheath 1606 also has some compressibility to take up some excess travel of cable 1620 since at a certain point, depending on the initial bend in the sheath 1606, sheath 1606 will compress before cable 1620 can travel any further. In this arrangement, sheath 1606 functions similar to a relatively rigid spring.

Figure 58:
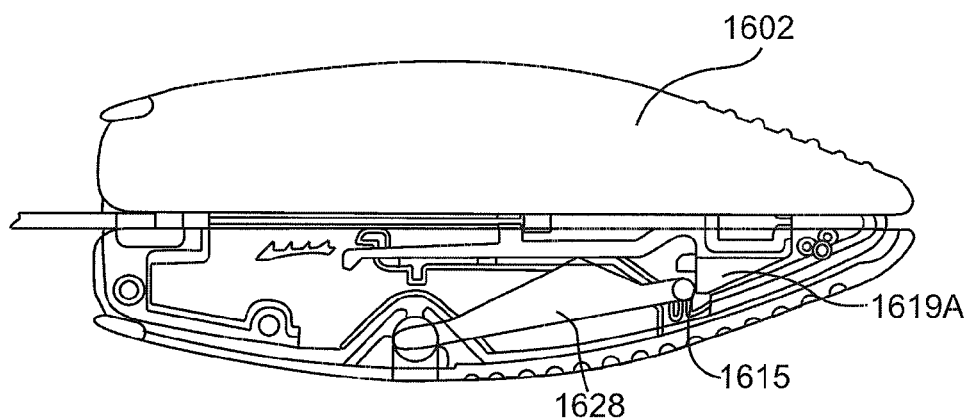
FIG. 58 depicts an embodiment of a single squeeze actuator in accordance with the invention.

FIG. 58 shows a single squeeze mechanism which allows the links 1626, 1628 to release from surface 1615 of body portion 1611. More particularly, the portion of links 1626, 1628 that engages surface 1615 of body portion 1611 rides to a location beyond the end of surface 1615 as shown in FIG. 58 so that body portion 1611 is no longer engaged with links 1626, 1628. As a result, body portion 1611 is permitted to return to the starting position as a result of the force in the compression of the sheath 1606. This embodiment employs thinner fins 1619a than the fins 1619 of the embodiment of FIGS. 55A-57D such that the body portion 1611 is free to return to the starting position.

The various embodiments of the devices of the present invention described above, can be interchanged to provide various combinations of the activator, expander and applicator. Thus, different activators can be used with different expanders and/or activators within the scope of the present invention and the person skilled in the art would be able to adapt a given activator for use with a particular expander or applicator.

Figure 59:
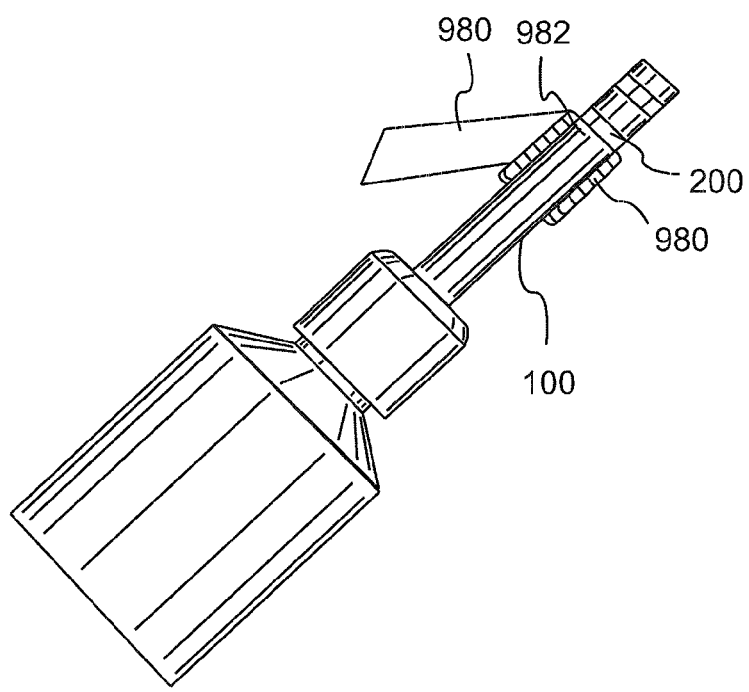
FIGS. 59-62 depict a pseudo end-to-side anastomosis procedure employing an anastomosis device in accordance with the present invention.

The use of the applicator, expander and activator of the present invention will now be described in relation to a pseudo end-to-side anastomosis procedure, while keeping in mind that this procedure is easily translated into a transluminal end-to-side or end-to-end anastomosis. What is meant by a pseudo end-to-side anastomosis is a side-to-side anastomosis, which is converted to an end-to-side anastomosis by closing the free end of the graft, downstream of the anastomosis, as described in U.S. Pat. No. 6,485,496. Referring to FIGS. 59-62, a pseudo end-to-side anastomosis procedure is depicted. In the first step of the procedure, applicator 100 is inserted into one end 981 of vessel graft 980, shown in partial cross-section in FIG. 59. Applicator 100 is then inserted through a hole 982 in the sidewall of graft 980, having dimensions in a range suitable for the size of applicator 100, while the proximal anvils 108 remain within the lumen of graft 980, such that the distal end of applicator 100 with distal anvils 112 protrudes from hole 982 in the sidewall of graft 980 as shown in FIG. 59. This is easily effected in a correctly sized hole, due to the elasticity of tissue, which results in a preferred position of the hole around the most slender part of applicator 100. As a result, staple-like elements 202 of connector 200 are correctly positioned relative to the edges of hole 982 in the sidewall of graft 980.

Figure 60:
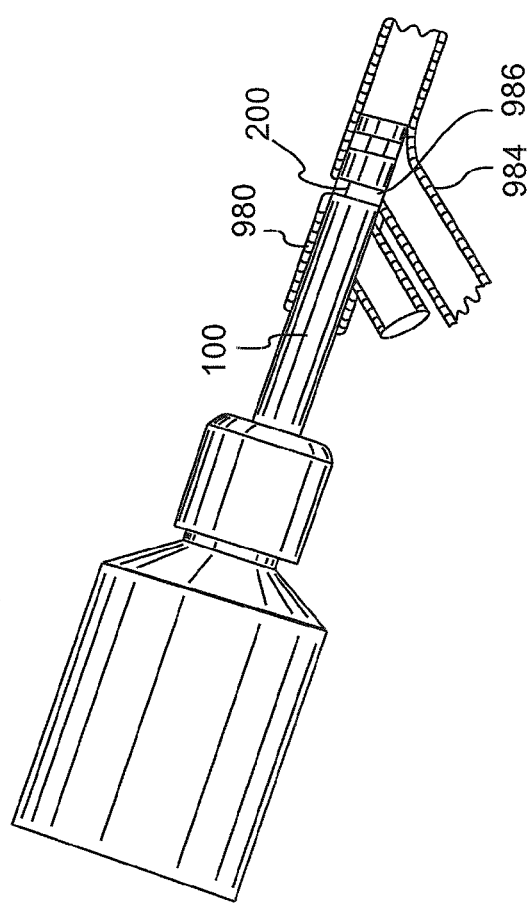
Figure 61:
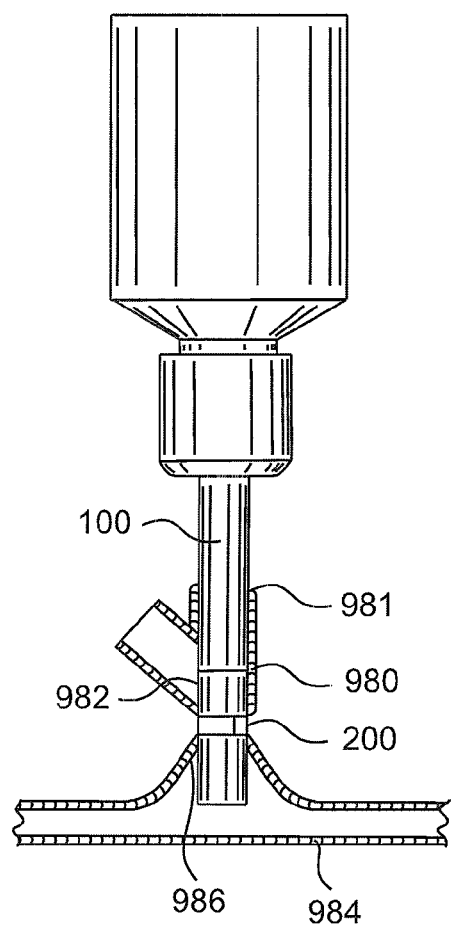

In the next step of the process, shown in FIG. 60, the distal end of applicator 100 is inserted into a hole 986 in the sidewall of target vessel 984, also having dimensions in a range suitable for the size of applicator 100, such that distal anvils 112 are completely inside the lumen of vessel 984. Again, as a result, staple-like elements 202 of connector 200 are consequently also correctly positioned relative to the edges of hole 986 in the sidewall of target vessel 984. At this point, applicator 100 is actuated to cause expansion and movement of inner tube 102 relative to outer tube 104 as discussed above. The combination of expansion and movement of inner tube 102 causes connector 200 to pierce and engage with the sidewalls of graft vein or artery 980 and artery 984 as described above. Applicator 100, in the release state, after expansion and staple closure of connector 200 is shown in FIG. 61. With connector 200 in its expanded and compressed position, a fluid connection is created between hole 982 in the sidewall of graft vein 980 and hole 986 in the sidewall of target vessel 984.

Figure 62:
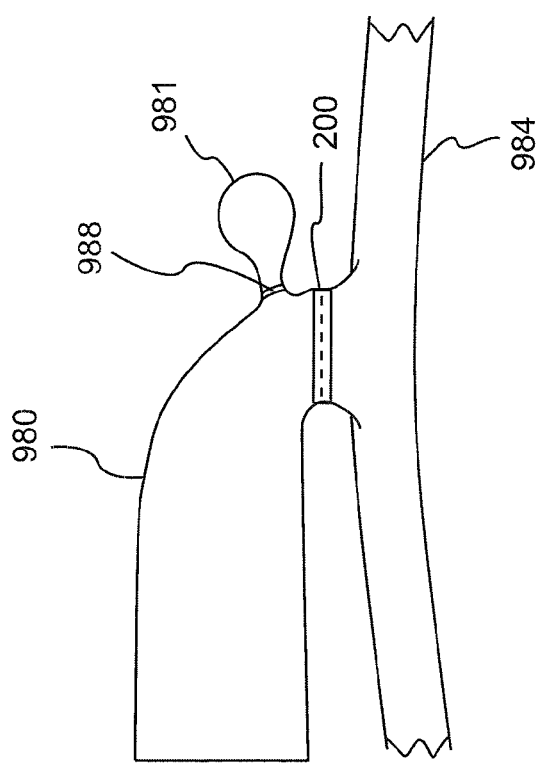

At this point, applicator 100 is removed to disengage connector 200 from applicator 100, and applicator 100 is removed from the anastomosis site via the end 981 of graft vein 980. In the final step, to complete the anastomosis, end 981 of graft vein 980 is sutured closed by sutures 988 as shown in FIG. 62, or alternatively clipped together by a hemoclip, or closed by an endoluminal plug, a suture loop or by any other means, such as diathermia or ultrasound known in the art to reliably close a blood vessel.

Figure 44:
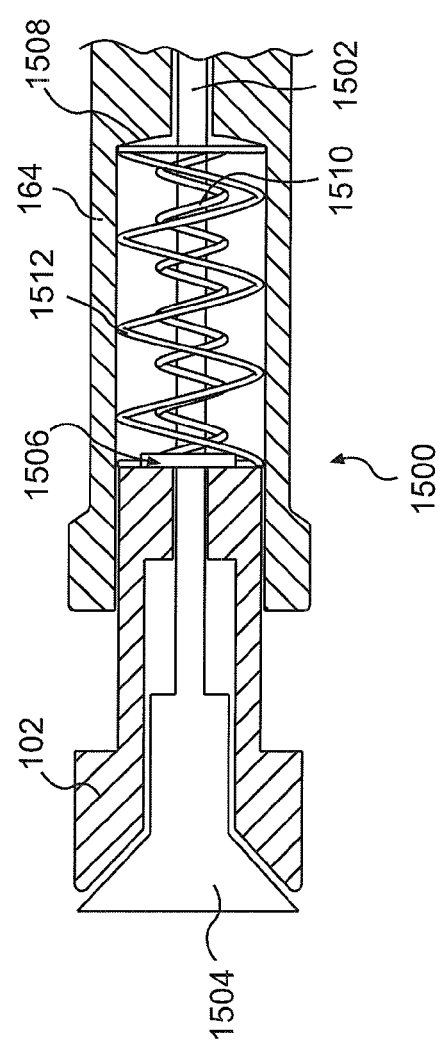
FIG. 44 is cross-sectional view of an alternative embodiment of a dual-spring actuator.

As mentioned, it will be understood that the same method can be used to realize a true end-to-side anastomosis, for example using a trans-luminal catheter-carrying device 1500 as shown in FIG. 44. In this case, device 1500, which is properly sized relative to the diameter of open end 981 of graft 980, is moved through graft 980 and positioned inside end 981, such that only the distal portion of device 1500 carrying distal anvils 112 is disposed out end 981. If necessary, the diameter of open end 981 can be reduced to better fit the diameter of applicator 100, for example, by slightly constricting it with a an elastic band or purse-string suture, which stretches or breaks upon the subsequent expansion. Device 1500 is then inserted into target vessel 984 and actuated as described above. Using the same principles, it is possible to create an end-to-end anastomosis with a properly dimensioned device like device 1500.

Internal Side-to-Side Anastomosis

Making internal side-to-side anastomosis requires two important steps: the creation of correctly sized holes in the vessels to be joined, and the subsequent introduction in the graft and in the target vessel of the device. The requirement of unobstructed blood flow through the resulting anastomosis, implicating an anastomotic orifice at least equal to the cross sectional area of the target coronary after potential recoil of the expanded ring, as well as after being covered with neo-intima as part of the body healing response, shows that the initial anastomotic orifice should be oversized relative to the target vessel. This over-sizing requirement generates additional difficulties, like the need for a bigger size applicator in a vessel, which is consequently more difficult to introduce. From a surgical point of view, the method should require minimal manipulation and be suitable for a reliable check of each subsequent step, like visual or echographic inspection to optimally and safely suit endoscopic or combined endoscopic and percutaneous transvascular application, or even total percutaneous application. Two deployment methods are described below that accomplish these goals.

Semi-Axial Introduction

Figure 63A:
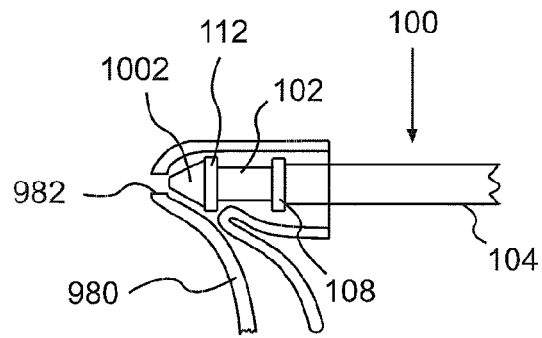
FIG. 63A shows a side view of the applicator with nosepiece inside the graft vessel in a first position.
Figure 63B:
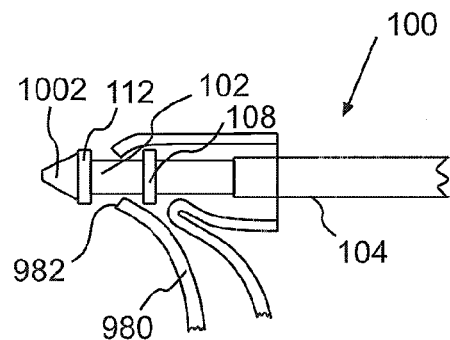
FIG. 63B shows a side view of the applicator with nosepiece penetrating the graft vessel in a second position.

Semi-axial introduction is a method for achieving internal side-to-side anastomosis. The semi-axial introduction method requires insertion of applicator 100, preloaded with graft 980, in an axial direction into target vessel 984, followed by a rotation to a substantially perpendicular position relative to target vessel 984. FIGS. 63A-63K show aspects of the semi-axial introduction method. FIGS. 63A and 63B show the steps of preloading applicator 100 with graft 980. Applicator 100 is inserted into the free end 981 of graft vessel 980, after making a hole or an incision 982 in the graft. At the distal end of applicator 100 is a nosepiece 1002 and several sets of anvil pairs 108, 112, depicted schematically. A connector 200, not shown, would be located on the outside of inner tube 102 between anvils 108 and anvils 112, as shown in other figures in the present application. Nosepiece 1002 is pressed against side hole 982. FIG. 63B shows nosepiece 1002 and anvils 112 pushed through side hole 982. In this embodiment, nosepiece 1002 is streamlined and conical in shape in order to facilitate pushing nosepiece 1002, distal anvils 112 and part of connector 200 through side hole 982.

Figure 63C:
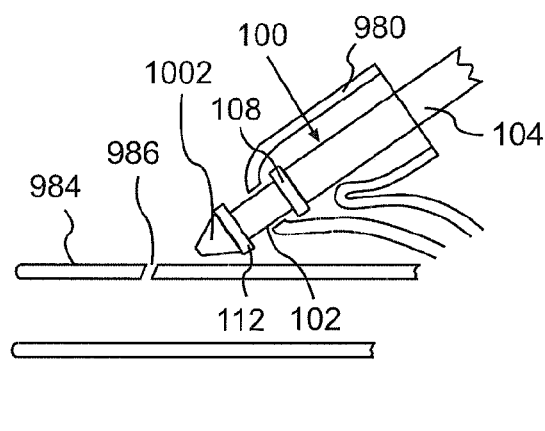
FIG. 63C shows a side view of the applicator with nosepiece and the target vessel in a third position.
Figure 63D:
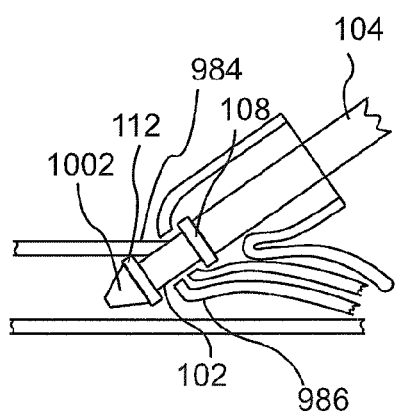
FIG. 63D shows a side view of the applicator with nosepiece penetrating the target vessel in a fourth position.

FIG. 63C shows nosepiece 1002 and applicator 100 being positioned substantially parallel to target vessel 984 and hole or incision 986 to thereby position connector 200 substantially parallel to the target vessel. FIG. 63D shows nosepiece 1002 and distal anvils 112 advanced to a position whereat a portion of connector 200 is advanced into hole 986.

Figure 63E:
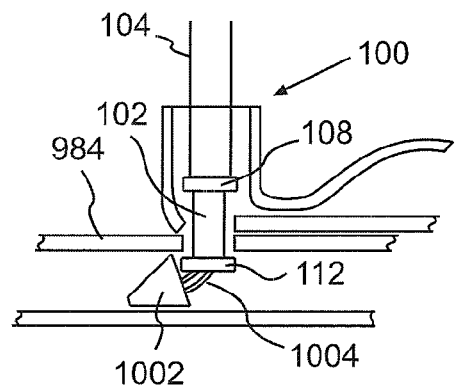
FIG. 63E shows a side view of the applicator with nosepiece being placed in a perpendicular position.

FIG. 63E shows applicator 100 in position for expansion and deformation of connector 200. Connector 200 is preferably actuated when it is positioned substantially perpendicular to target vessel 984 and hole 986. This requires applicator 100 to be brought from the substantially parallel position to a perpendicular position, relative to target vessel 984. At this point, applicator 100 is actuated to expand and cause movement of anvils 112 of inner tube 102 relative to anvils 108 of outer tube 104. The combination of expansion and movement of inner tube 102 causes connector 200 to expand and engage the sidewalls of graft vessel 980 and target vessel 984.

In order to avoid damage to the interior of target vessel 984, nosepiece 1002 is movable from a first position, parallel to the axis of applicator 100 during insertion, to a second position, at an angle to the axial line of applicator 100. In a preferred embodiment, during actuation of connector 200, nosepiece 1002 separates from connector 200 and remains attached to applicator 100 by a tether 1004. Tether 1004 provides mobility for nosepiece 1002 thereby preventing possible damage that may be caused during the actuation of connector 200. Tether 1004 may be constructed of either an elastic string, or a spring. Alternatively, nosepiece 1002 may be attached via a non-elastic cord that can be released before actuation of connector 200. Additionally, nosepiece 1002 can be constructed with a magnetic material and be released and attached to applicator 100 with magnetic force.

Figure 63F:
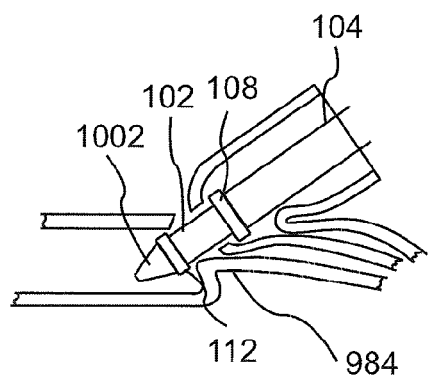
FIG. 63F shows a side view of the applicator getting caught in the target vessel.
Figure 63G:
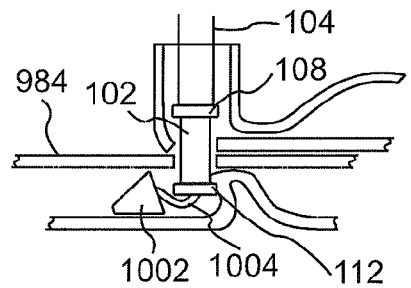
FIG. 63G shows a side view of the applicator getting caught in the target vessel and the back surface of the target vessel being attached to the graft vessel.

A potential problem with the method of rotating applicator 100 to a perpendicular position relative to the target vessel described above is that it requires the diameter of distal portion of applicator 100 to be smaller, or at most equal to the inner diameter of the target vessel 984. Otherwise, distal anvils 112 may become wedged into target vessel 984 and the back wall of target vessel 984 may become stuck around the distal end of applicator 100, as shown in FIG. 63F. This may cause the back wall of target vessel 984 to be pulled toward the upper wall of target vessel 984 and, as shown in FIG. 63G, through actuation of connector 200 become stapled to the upper wall of target vessel 984 and graft vessel 980, thus permanently closing the target vessel in one direction. This is undesirable, since in many situations, including surgical myocardial revascularization, the target vessel should be open in both directions. The described phenomenon tends to occur with large applicators, relative to the target vessel, and therefore interferes with the required over-sizing of the anastomosis as described above.

Figure 63H:
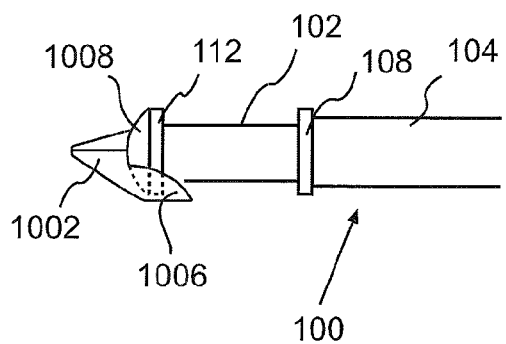
FIG. 63H shows a side view of the nosepiece with shield.
Figure 63I:
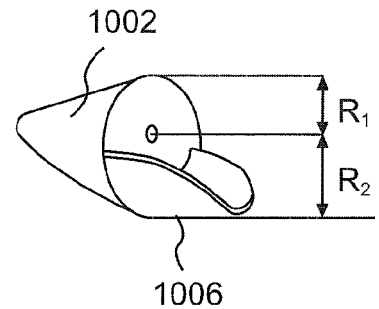
FIG. 63I shows an isometric view of the shield.
Figure 63J:
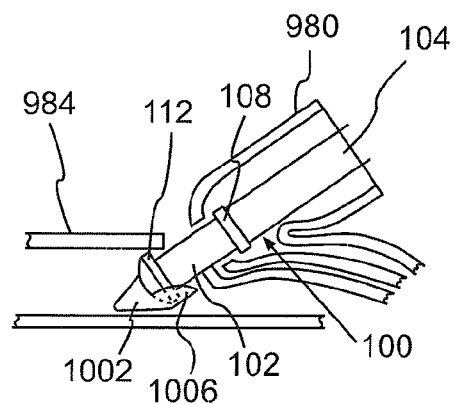
FIG. 63J shows a side view of the operation of the shield on the applicator in target vessel.
Figure 63K:
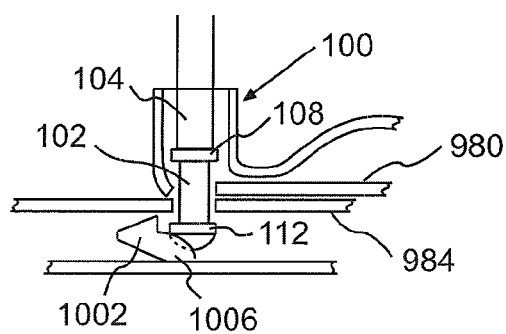
FIG. 63K shows a side view of the operation of the shield on the applicator when the applicator is placed in a perpendicular position.

One solution to the aforementioned problem is the addition of shield 1006 to nosepiece 1002, shown in FIGS. 63H and 63I. As shown in FIGS. 63J and 63K, shield 1006 prevents the back wall of target vessel 984 from holding onto distal anvils 112 by holding the vessel wall away from distal anvils 112.

To prevent nosepiece 1002 from becoming wedged within target vessel 984 and therefore complicating withdrawal, radius $R_1$ of nosepiece 1002 in the area of the rounded front portion 1008 of applicator 100 may be reduced in relation to the radius $R_2$ of the nosepiece 1002 in the area of the shield 1006, thereby resulting in an oval cross-section of nosepiece 1002, shown, for example, in FIG. 63H. Alternatively, nosepiece 1002 may have other means to reduce its diameter, for example by being deflatable, or by being deformable.

As shown in FIG. 63H, to facilitate the introduction of applicator 100 into target vessel 984, applicator 100 has a rounded front portion 1008, which streamlines the overall contour of the distal end of applicator 100. Nosepiece 1002 has a concave back that fits into front portion 1008. Additionally, the rounded front portion 1008 facilitates the pivoting motion of the nosepiece 1002 when applicator 100 is moved to the perpendicular position shown in FIG. 63K. As shown in FIG. 63K, when applicator 100 is in a perpendicular position, shield 1006 and nosepiece 1002 are substantially parallel to the back end of target vessel 984. Nosepiece 1002 and shield 1006 may be connected centrally to the distal end of applicator 100 by a string or flexible tubing, which may be elastic, or a spring, in a manner similar to the tether 1004 of FIGS. 63E and 63G. Alternatively, nosepiece 1002 and shield 1006 can be connected eccentrically via a connection from the tip of shield 1006 to a suitable part of applicator 100. In such a case nosepiece 1002 can be held in place by additional means, such as magnetic force. Additionally, connecting the nosepiece 1002 at the proximal tip of shield 1006 may facilitate withdrawal of applicator 100, by preventing shield 1006 from hooking under the connector 200.

Perpendicular Introduction

Perpendicular introduction is a second method for achieving internal side-to-side anastomosis. The perpendicular introduction method requires a motion in a direction, perpendicular to the axis of applicator 100, to insert toe 1010 (or anvil 112 in case of absence of insertion shoe 1010) of applicator 100, which is tilted only slightly relative to the target vessel and has been preloaded with graft 980, into hole 986 of target vessel 984, followed by a slight rotation back to a more perpendicular position relative to the target vessel. FIGS. 64A-64D show aspects of the perpendicular introduction method.

FIG. 64A shows applicator 100 inserted into the free end of graft vessel 980 and pushed through side hole or incision 982 inside out. The axially asymmetric insertion foot 1010 shown here is optional. An applicator 100 without any nosepiece or insertion foot may also be used with this technique. FIG. 64B shows the embodiment with an insertion shoe 1010. Insertion shoe 1010 is brought out through side hole 982 by passing out of the rounded part of shoe 1010 first.

Next, as shown in FIG. 64C, preloaded applicator 100 is brought to the target vessel 984 and tilted to some degree towards the toe of shoe 1010. The tip of shoe 1010 is then pushed into hole 986 of target vessel 984 until the anvils adjacent on that side of applicator 100 are inside the target vessel 984.

Next, as shown in FIG. 64D, applicator 100 is tilted backwards to a substantially perpendicular position to insert the heel of shoe 1010 and adjacent anvils on that side of applicator 100 as well. Applying some traction on the surrounding tissue with an instrument, like a surgical forceps, may facilitate proper introduction of applicator 100.

Figure 65A:
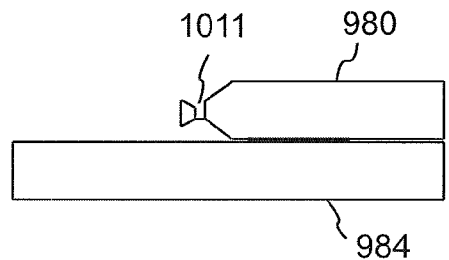
FIG. 65A shows a side view of a graft with a suture.
Figure 65B:
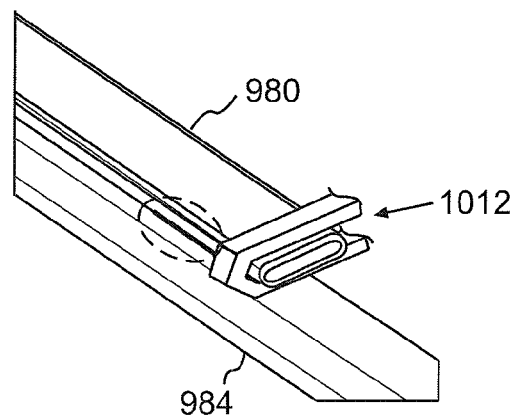
FIG. 65B shows a side view of a graft with a clip.

Using either the semi-axial introduction method or the perpendicular introduction method, applicator 100 is activated to realize the anastomosis, and applicator 100 is subsequently withdrawn, and the free end of graft vessel 980 is closed with suture 1011, as show in FIG. 65A, or clip 1012, as shown in FIG. 65B, or any other vessel closing means. Alternatively, an additional anastomosis can be made with the same graft further downstream in order to create a jump graft.

Part of the semi-axial introduction method or the perpendicular introduction method is the proper sequence of actions during actuation of connector 200, which causes stapling or connection of the graft vessel to the target vessel. Any of the following sequences can be used as part of the semi-axial introduction method or the perpendicular introduction method described hereunder: first expansion of the connector 200 via expansion, then deformation of the staples, clips or the like to clamp graft vessel 980 and target vessel 984 together; the simultaneous expansion and deformation of the staples, clips or the like to connect graft vessel 980 and target vessel 984; first deformation of the staples, clips or the like, followed by expansion of connector 200 and deformation of connector 200 without any expansion. The sequence of expansion first followed by deformation of connector 200 is the preferred sequence, however, due to the increased reliability of tissue positioning between the anvils before deformation of the connector 200, minimizing the chance of miscapture of tissue.

Also important is the precise way the tissue is engaged by connector 200. Any of the following ways can be used as part of the methods: complete tissue penetration of the tips of the connecting means; partial tissue penetration; or clamping of the tissue only, without tissue penetration. However, like hand suturing, complete tissue penetration is the preferred way due to the increased strength of the tissue bond that is effected, as well as the guaranteed capturing of all vessel wall layers (adventitia, media and intima), which is an important surgical principle to minimize the chance of complications like tissue escape or vessel wall delamination.

Figure 65C:
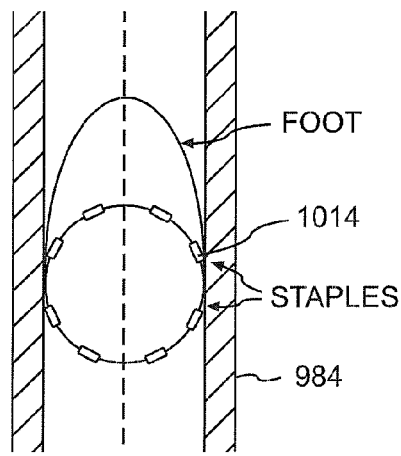
FIG. 65C shows a top view of the graft.

Also important is the orientation of the staples, clips or the like relative to the axis of the target vessel 984. Connectors 200 suitable for anastomoses with coronary arteries, will often feature eight pairs of staples, clips or the like, for example staples 1014 shown in FIG. 65C, spaced equally on connector 200. As discussed above, connector 200 may have more or less staple elements 202, depending upon the size of the anastomosis. For example, for smaller vessels, connector 200 may have seven or less staple elements 202, or for larger vessels, connector 200 may have nine or more staple elements 202. In each case, applicator 100 preferably would include a number of anvils 108, 112 that correspond to the number of staple elements 202. While any orientation may lead to good results, the orientation shown in FIG. 65C with the central axis of target vessel 984 between two adjoining staples is the preferred position. The orientation relative to the grafted vessel is generally less important.

Guide Wire Methods

The semi-axial introduction method and the perpendicular introduction method described above is also applicable to and can benefit from guide wire methods.

Semi Axial Introduction

Figure 66A:
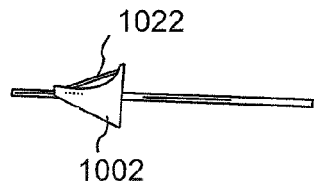
FIG. 66A shows a side view of a guide wire and guide tube.

Preloading is done by inserting guide tube 1018, as shown in FIG. 66A, with a rounded (non-traumatic) end into the lumen of graft vessel 980 through its free end. One end of guide tube 1018 is pushed against the wall of graft vessel 980 at the desired spot of the anastomosis, and stiff guide wire 1020 is advanced through guide tube 1018 and pushed to penetrate the wall of graft vessel 980 creating a hole 982. Guide tube 1018 is then removed from graft vessel 980.

Figure 66B:
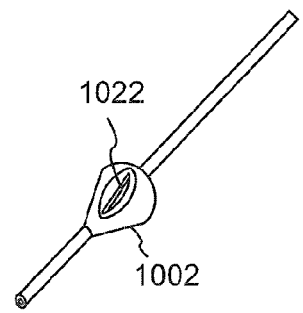
FIG. 66B shows a side view of a guide wire and applicator.

After removing guide tube 1018 from graft vessel 980, applicator 100 is advanced over guide wire 1020, as shown in FIG. 65B. The applicator 100 is provided with a properly dimensioned central cylindrical hole extending its entire length for accepting the guide wire. To facilitate the advancement of applicator 100, a cutting edge 1022, as shown in FIGS. 66A and 66B, may be built into nosepiece 1002. As shown in FIG. 66A, cutting edge 1022 is kept within the contour line of nosepiece 1002. Consequently, cutting edge 1022 can only cut when forced through a small hole and cannot damage the tubular inside of the target vessel 984.

Figure 65D:
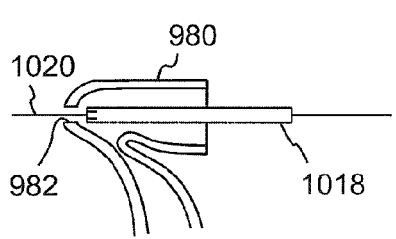
FIG. 65D shows a side view of an inserted guidewire.
Figure 65E:
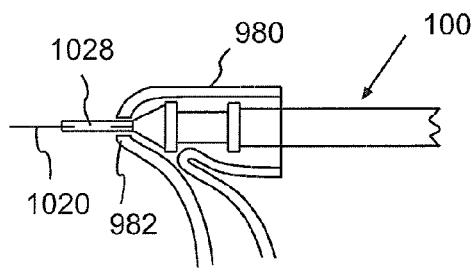
FIG. 65E shows a side view of a nosepiece attached to an applicator by a thin walled, flexible tube.
Figure 66C:
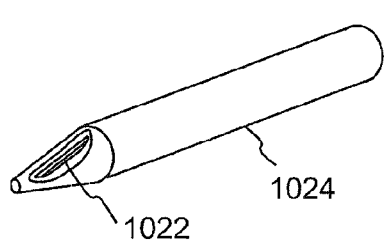
FIG. 66C shows a side view of the cutting edge.
Figure 66D:
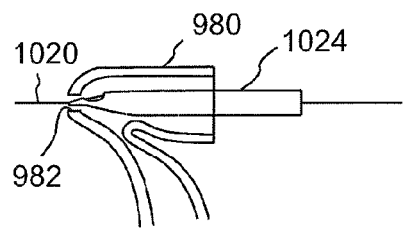
FIG. 66D shows a side view of the cutting edge on a nosepiece.

Alternatively, as shown in FIGS. 66C and 66D, cutting edge 1022 may be built into a separate, conical rod 1024, which is advanced over guide wire 1020 to create hole 982. Rod 1024 is then removed and applicator 100 is advanced over guide wire 1020. In alternative embodiments, nosepiece 1002 may be attached to applicator 100 by a thin walled, flexible tube 1028, shown in FIG. 65E. Preferably, tube 1028 extends some distance in front of nosepiece 1002. Also, thin shield 1006, shown in FIGS. 63H and 63I, may be added to the nosepiece 1002. Cutting edge 1022 may be attached to nosepiece 1002 or rod 1024. Cutting edge 1022 may also be used without guide wire 1020.

Figure 66E:
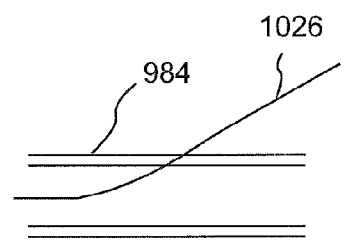
FIG. 66E shows a side view of a cutting edge and guide rod.

Guide wire 1020 will then penetrate the wall of the target vessel 984, or be inserted into a previously made arteriotomy. Alternatively, guide wire 1020 may be removed and the applicator 100 may be advanced over a second guide wire 1026 coming out of the target vessel 984, as shown in FIG. 66E. Second guide wire 1026 may be brought into the bloodstream at a location distant from the operative site, like a percutaneous insertion site in the femoral artery in the groin, and be steered to the desired spot and be made to penetrate the vessel wall there, or may be brought into the target vessel 984 at the anticipated site of the anastomosis from the operative field, through a hollow needle or some other method to create a hole in the wall.

After usage of guide wire 1020, a device for enlarging the hole in a controlled way is employed. In the preferred embodiment, guide rod 1024 with the built in cutting edge 1022, as shown in FIGS. 66C and 66D, is advanced over guide wire 1020 and removed thereafter.

Figure 66F:
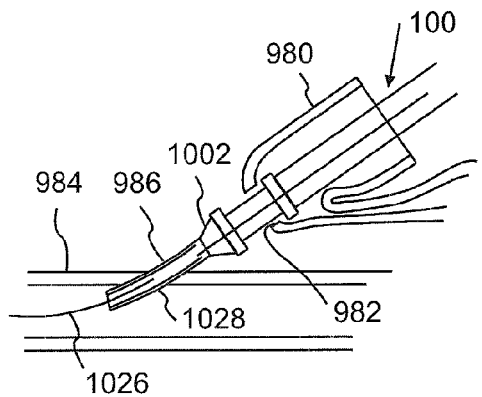
FIG. 66F shows a side view of the guide wire and guide rod inside the graft vessel in a first position.
Figure 66G:
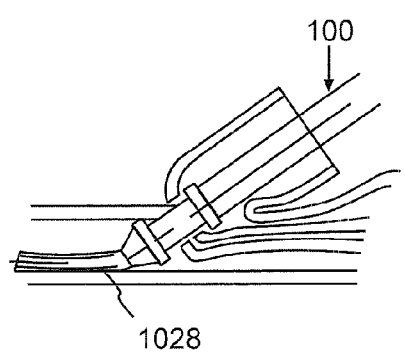
FIG. 66G shows a side view of the second guide wire inside the target vessel.
Figure 66H:
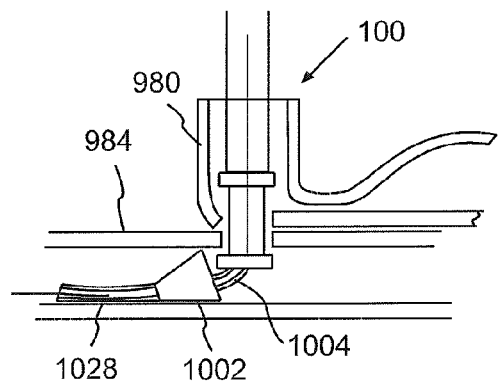
FIG. 66H shows a side view of the applicator using the guide wire and flexible tube in a second position.

Alternatively, as shown in FIG. 66F, applicator 100 with the nosepiece 1002 is advanced over guide wire 1020 directly to enlarge hole 986 during insertion, and pushed into target vessel 984 over either guide wire 1020 or guide wire 1026. As shown in FIG. 66G, guide wire 1020 is pulled back to enable the required pivoting movement of the nosepiece 1022, but it remains within the distally extending flexible tubing 1028 in the case of a percutaneous guide wire technique. In case stiff guide wire 1020 was brought in from the operative field, it is withdrawn into applicator 100. As shown in FIG. 66H, applicator 100 is then brought into a perpendicular position and is ready to be actuated.

Perpendicular Introduction

There are several ways to use guide wires with this insertion method.

One Wire Technique

As shown in FIGS. 67A and 67B, wire insertion shoe 1030 features a channel 1032 oriented perpendicularly to the axis of the applicator for providing access to a guide wire 1026 that extends from target vessel 984 as described above. After creating a controlled arteriotomy, for example by advancing guide rod 1024 with built in cutting edge 1022, or by advancing any alternative cutting device over guide wire 1020, as shown in FIG. 66D, applicator 100 can be advanced over guide wire 1020 and be manipulated into hole 986 in target vessel 984 by tilting it forward and backwards as described above, after removal of guide wire 1020 or retracting it into the target vessel such that the free end of guide wire 1026 that extends from the target vessel becomes located inside shoe 1030. Alternatively, a sharp, cutting edge 1022 may be built into wire insertion shoe 1030 to combine the creation of a controlled arteriotomy and insertion of applicator 100 in one movement.

Wire insertion shoe 1030 may also be equipped with a temporary lock mechanism 1034, such as shown in FIGS. 67C and 67D, to reversibly clamp wire insertion shoe 1030 and applicator 100 to a specific spot on guide wire 1026 that extends from target vessel 984. This permits movement of applicator 100 back and forth by manipulating guide wire 1026. In the case of a percutaneously introduced guide wire 1026, applicator 100 can be drawn into target vessel 984 and positioned by manipulating guide wire 1026, thus adding the potential to remotely control the positioning of applicator 100.

One embodiment of such a lock is shown in FIGS. 67C and 67D. Channel 1032 inside wire insertion shoe 1030 features a part with increased diameter, containing a short tube 1035, which can be pulled upwards by cable 1036 connecting wire insertion shoe 1030 to applicator 100. Guide wire 1026 is introduced through channel 1032 in wire insertion shoe 1030 while tube 1035 with the connecting cable 1036 is relatively lax. When the applicator 100 is at the desired spot on guide wire 1026, the connecting cable 1036 is pulled, thereby moving the short tube 1035 to a position eccentric to the central axis of the channel 1032, effectively clamping guide wire 1026. At the same time, wire insertion foot 1030 is rigidly connected to the front end of applicator 100. Releasing the connecting cable can reverse the process. A temporary lock mechanism 1034 may also be used in combination with a semi-axial introduction method.

Two Wire Technique

Figure 67E:
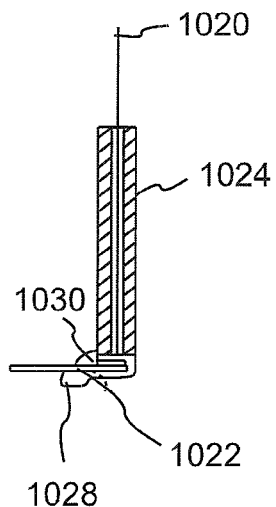
FIG. 67E shows a side view of a guide rod, applicator and second guide wire in a first position.

As shown in FIGS. 67A and 67B, wire insertion shoe 1030 features channel 1032 for guide wire 1020 or 1026 as described above. In another embodiment shown in FIG. 67E, wire insertion shoe 1030 is not yet mounted on applicator 100, but instead is mounted on a guide rod 1024. Guidewire 1020 can be connected to shoe 130, and is preferably disposed at least partially within guide rod 1024. Shoe 1030 has a channel 1032 extending lengthwise through shoe 1030 sized to accommodate guide wire 1026. Preferably, a piece of flexible tubing 1028 extends from the toe of shoe 1030, and optionally, a cutting edge 1022 is used to help gain access to target vessel 984.

Figure 67F:
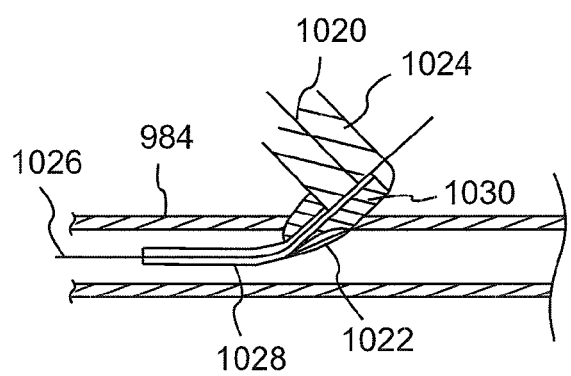
FIG. 67F shows a side view of the applicator entering the target vessel using a guide wire in a second position.

As shown in FIG. 67F, guide rod 1024 with shoe 1030 is advanced over the distal end of guide wire 1026, which extends from target vessel 984, until wire insertion shoe 1030 is partially introduced into the arteriotomy in target vessel 984. The arteriotomy is preferably formed in a longitudinal direction relative to target vessel 984. Guide wire 1026 is then pulled back into the target vessel or flexible tubing 1028 to permit insertion of the heel of wire insertion shoe 1030 into the target vessel.

Figure 67G:
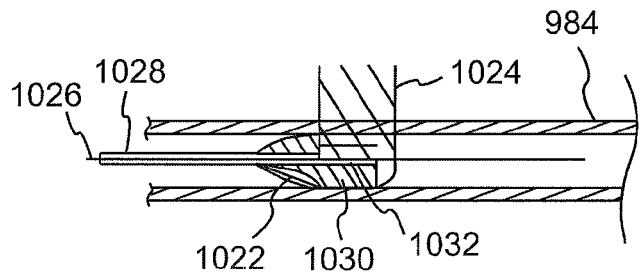
FIG. 67G shows a side view of the applicator and wire insertion shoe device inside the target vessel in a third position.
Figure 67H:
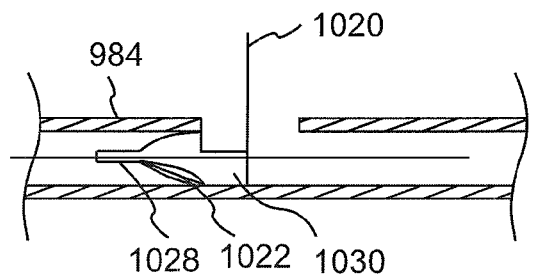
FIG. 67H shows a side view of the wire insertion shoe device and the second guide wire inside the target vessel in a fourth position.
Figure 67I:
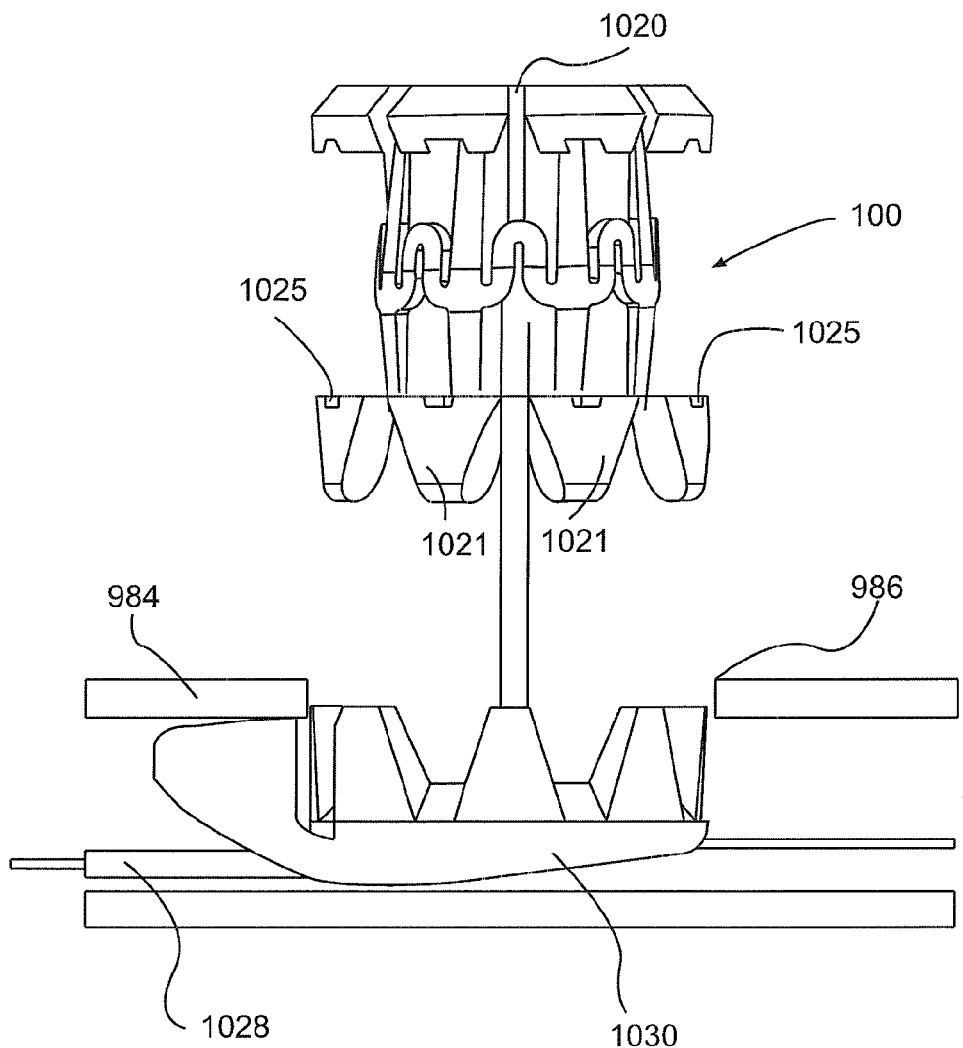
FIG. 67I shows a side view of the applicator inside the target vessel and graft vessel in a fifth position.

As shown in FIG. 67G, once shoe 1030 is disposed within target vessel 984, guide wire 1026 can then be advanced again through channel 1032 of insertion shoe 1030 to capture insertion shoe 1030 within opening 986 of target vessel 984. As shown in FIG. 67H, guide rod 1024 is then removed, exposing second guide wire 1020 originating from the wire insertion shoe 1030. As shown in FIG. 67I, applicator 100, now without any nosepiece, preloaded with graft 980 (not shown), is advanced over second guide wire 1020. In situ wire insertion shoe 1030 is disposed at least partially within opening 986 of target vessel 984. Protrusions 1025 extend proximally relative to second guidewire 1020 to assist in maintaining the arteriotomy in the open position. In this way, applicator 100 may be passed down guidewire 1020 to shoe 1030 from a position outside target vessel 984 to a position whereat at least a distal portion of applicator 100 is located within target vessel 984. In a preferred embodiment, shoe 1030 includes male or female features 1021 that are configured to mate with male or female features 1023 located on a distal portion of applicator 100. In addition or alternatively, shoe 1030 can maintain a clear path for applicator 100 by pushing the longitudinal arteriotomy in target vessel 984 open in a transverse direction from the inside, and applicator 100 can simply be maneuvered to a position whereat applicator 100 can be connected to shoe 1030.

Internal Mammary Artery

In one embodiment, graft vessel 980 can be the left or right internal mammary artery, commonly referred to as the IMA. The IMA can be dissected away from the chest wall and prepared for loading applicator 100 therethrough. The length of the pedicalized IMA should be sufficient so that the distal end of the IMA can be positioned outside of the body (with the proximal end still attached) through a properly located port. In a preferred embodiment of the method, the port or opening is located intercostally, but may be located outside the rib cage or can be created by removing part of a rib or by separating the ribs. Once the distal end of the IMA is located outside the body, guidewire 1020 can be inserted into the opening of the IMA distal end and can be used to create an arteriotomy in the side of the IMA in a manner similar to that shown in FIG. 65D. Alternatively, the arteriotomy can be created using a separate instrument from either the outer surface of the IMA or from the inner surface of the IMA via the open end.

The arteriotomy can be enlarged as described above using cutting edge 1022 or some other device to make it easier to pass the distal end of applicator 100 through the arteriotomy and to better size the arteriotomy for the anastomosis, if required. Cutting edge 1022 can also be used to create an arteriotomy better suited for an anastomoses, such as one having a more uniform appearance or having a particular shape. Alternatively, applicator 100 can be passed directly through the arteriotomy created by guidewire 1020. It is understood that, where a guidewire is said to create an arteriotomy, the guidewire may include a cutting surface to create the opening or the guidewire may be used in conjunction with a separate cutting or coring instrument.

Once properly positioned within the IMA, guidewire 1020 can be removed from applicator 100, and applicator 100 can be passed back into the patient's body through the port and positioned near a second arteriotomy made in target vessel 984 via a guidewire 1024 that extends from the arteriotomy. The second arteriotomy can be formed by guidewire 1024 that enters target vessel 984 directly at the second arteriotomy site (in which case the second arteriotomy is created from outside the target vessel 984 and into the interior of target vessel 984) or guidewire 1024 can enter target vessel 984 from a location spaced from the second arteriotomy (in which case the second arteriotomy is created from the interior or lumen of target vessel 984 and passes through the outer surface of target vessel 984). In the latter case, guidewire 1024 can enter target vessel 984 via a peripheral vessel that communicates with the target vessel or via the target vessel itself, at a position distal to the blockage or proximal to the blockage.

Applicator 100 can be loaded over guidewire 1024 through the same lumen vacated by guidewire 1020 or by a separate lumen formed in applicator 100. Applicator 100 may be loaded over guidewire 1024 at a location within the patient's body, but preferably applicator 100 is loaded over guidewire 1024 at a location outside the patient's body. In this way, the surgeon can load applicator 100 onto the graft vessel (an IMA) and then onto guidewire 1024 at a location where he or she can visually confirm the correct positioning. Following those steps, the surgeon can pass applicator 100 and graft vessel 980 down guidewire 1024 to the site of the distal or target vessel arteriotomy, whereupon the distal end of applicator 100 can be positioned within target vessel 984. As discussed above, applicator 100 is then manipulated to expand and compress connector 200 to complete the anastomosis between target vessel 984 and graft or bypass vessel 980. Applicator 100 and guidewire 1024 are then removed from the site, and, if needed, the distal end of the IMA is closed using a clip, suture or other means.

In an alternative method, guidewire 1020 can be used as a guide to locate the target vessel arteriotomy. In this case, once guidewire 1020 is passed through the open end of graft vessel 980, guidewire 1020 can be passed back into the patient's body through the port and then can be used to create an arteriotomy in the target vessel or simply to find the arteriotomy in the target vessel created by another means. In such a case, once the distal end of guidewire 1020 is disposed within target vessel 984, the surgeon can pass applicator 100 and graft vessel 980 distally along guidewire 1020 back into the patient's body via the port to the site of the distal or target vessel arteriotomy. As with the above method, the surgeon then positions the distal end of applicator 100 within target vessel 984, and manipulates applicator 100 to expand and compress connector 200 to complete the anastomosis between target vessel 984 and graft or bypass vessel 980. Applicator 100 and guidewire 1024 are then removed from the site, and, if needed, the distal end of the IMA is closed using a clip, suture or other means.

While the above anastomosis methods are described as being performed by applicator 100, it is understood that any type of connector device could used to perform the same method. Thus, for instance, a connector that is deployed by a balloon could also be positioned at the distal site via a guidewire 1022 or 1024. In either case, the guidewire could be loaded over the connector deployment device at a location external to the patient's body and then passed back to the location of the distal arteriotomy, where the balloon is passed through the distal arteriotomy and the connector deployed. In one embodiment, a guidewire is passed via a peripheral artery into the IMA.

The IMA is accessed via a port, preferably intercostally, pedicalized and dissected to create an open end. The guidewire is pushed out the open end of the IMA and passed out the port along with the pedicalized IMA. A connector of the type incorporated by reference above is then loaded onto the IMA and/or connected to the IMA. The connectors can include, for example, those depicted or described in U.S. Pat. No. 6,485,496, U.S. patent application Ser. No. 09/708, 617, International Published Patent Application No. WO 02/38055, or U.S. Patent Publication No. 2003/0045902, or an adhesive or nitinol clips, or any combination of the above or any other connector known to one skilled in the art. As described above, the connector and graft vessel are then passed over a guidewire that marks the location of the distal arteriotomy, back into the patient's body via the port, and distally along the guidewire until the connector and graft vessel are proximate the distal arteriotomy. At this stage, the connector is deployed using any method known to those skilled in the art to complete the anastomosis. Where the guidewire was placed peripherally, it may be removed by withdrawing it proximally via the peripheral vessel.

In an alternative embodiment, a guidewire is passed via a first port from outside the patient's body into a side branch of the IMA and into the IMA. As above, the IMA is then pedicalized and dissected (preferably from the first port, but possibly a second port) to form an open end. As described above, the connector is loaded onto the IMA outside the patient's body and passed back in via the port through which it had been removed. The connector is deployed to form the anastomosis, at which point the guidewire can be removed from the side branch of the IMA out the first port, unless it was removed at an earlier step in the method. The side branch of the IMA is then closed via a suture or clip or other method, and the port or ports are closed.

Alternatively, the IMA can be pedicalized and dissected and the guidewire can be passed through the open end of the IMA, passed out a dissected side branch of the IMA and then passed through a port. The open end of the IMA can be pulled outside a port to load a connector onto the open end either before or after passing the guidewire through the open end. Similar to the above method, the guidewire is then passed into an opening formed in the target artery and the IMA is guided via the guidewire to the anastomosis site. The connector is deployed to form the anastomosis, at which point the guidewire can be removed from the side branch of the IMA via the port, unless the guidewire was removed prior to deploying the connector. The side branch of the IMA is then closed via a suture or clip or other method, and the port or ports are closed.

While the anastomosis method described above uses an IMA (either right or left) as the bypass or graft vessel, the surgeon could use the gastro-epiploic or axillary artery in the same manner; i.e., free the vessel from internal tissue and position the distal end of the vessel outside the body (with the proximal end still attached) through a properly located port. In the alternative, the surgeon could use a branch of an IMA rather than the IMA, itself, to perform the procedure.

Finally, the surgeon may harvest a saphenous vein or radial artery or other vessel, or may use a synthetic or animal vessel as a bypass vessel. In such a case, the surgeon can anastomose one end of such a bypass vessel proximally to the aorta or distally to the blocked coronary artery using a connector or suture and then position the free end of the bypass vessel outside the body through a properly located port or opening. At this stage of the procedure, applicator 100 can be passed through the free or open end and out an arteriotomy formed in the bypass vessel in the manner described above, preferably over a guidewire. Alternatively, a connector can be attached to the free end of the graft. In this way, even a typical bypass procedure using a saphenous vein or the like can be conducted in a minimally invasive manner using a port or opening in the patient to access the free end of the graft vessel and load the connector or applicator over the free end at a position outside the patient's body. As described above, the free end of the bypass vessel, along with the applicator and/or the connector is then passed back through the port or opening into the patient's body and the anastomosis is completed.

Protective Rings

An anastomosis between the graft vessel and the target vessel, may be mechanically protected by an external protective ring 1100, as depicted in FIGS. 68a-68d. In positions susceptible to direct trauma, particularly the abdomen and limbs, potential permanent deformation or destruction of the expanded connector may result, which might obstruct the anastomosis. An additional external structure, like protective ring 1100, may be provided. Protective ring 1100 may have any suitable shape including, but not limited to, spherical, polygonal, elliptical, toroidal, and U-shaped. Protective ring 1100 is provided with a central hole or cavity 1112, which is large enough to fit around the anastomosis, and also provides an easy, unobstructed entry and exit for the joined vessels to the central hole 1112, for example, via indentations 1114. Protective ring 1100 protects the anastomosis by absorbing or deflecting forces that may cause trauma, thus improving the long-term safety and durability of the device. Protective ring 1100 may be made of one piece, in which case it should generally be brought into place before or during construction of the anastomosis, or may be made of several, interlocking pieces, in which case the ring can be placed after completion of the anastomosis. Besides protection, protective ring 1100 may have, but need not have, hemostatic functionality that can be provided by mechanically sealing the anastomotic line from the outside, or by coating protective ring 1100 on its inner surface, at least in the areas near or in contact with the anastomotic line, with one or more hemostatic substances for accelerating clot formation. Also, protective ring 1100 may be used as a matrix for the addition of biocompatible glue, to reinforce the anastomosis, to repair leaks or remedy oozing blood.

Figure 68B:
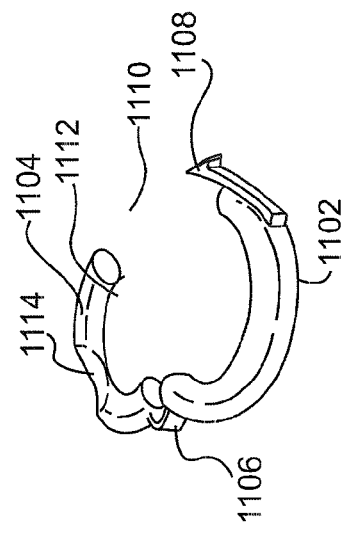
Figure 68D:
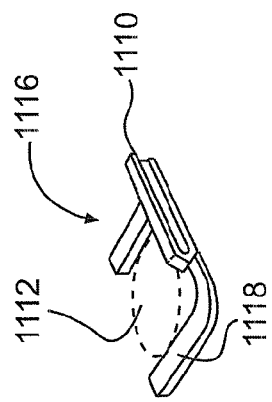
Figure 68A:
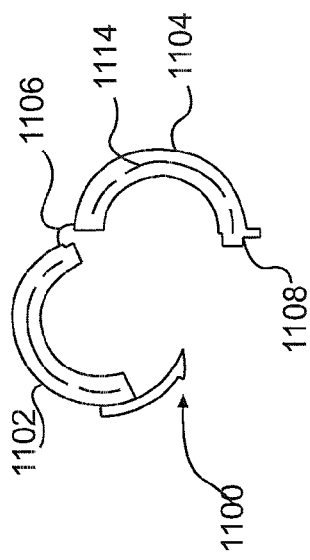
Figure 68C:
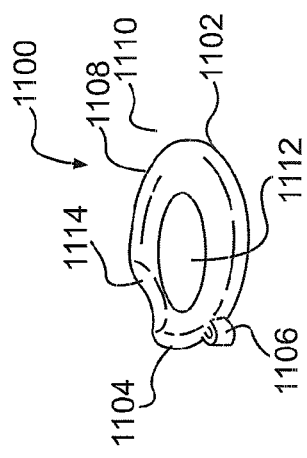

One embodiment, suitable for application after creation of the anastomosis with connector 200, is shown in FIG. 68a, which depicts external protective ring 1100 in an open position. External protective ring 1100 has two interlocking halves 1102, 1104. First anastomotic ring half 1102 and second anastomotic ring half 1104 are connected by hinge portion 1106. First anastomotic ring half 1102 and second anastomotic ring half 1104 are locked around a completed internal side-to-side anastomosis, after checking for hemostasis, by placing ring half 1104, for example, about one side of the anastomosis and pivoting ring half 1106 about the other side of the anastomosis, and then snapping together anastomotic ring locking portion 1108. External protective ring 1100 is preferably constructed of a stiff type of plastic (e.g. hard polypropylene), however it can be made of other materials.

FIG. 68b shows external protective ring 1100 placed around graft 1112, which is a completed internal side-to-side anastomosis, although it can be placed around other grafts as well and used in other procedures, such as, but not limited to, peripheral vascular surgery (fem-pop bypasses), intra-abdominal vascular procedures, hemo-dialysis shunt construction, and tissue auto transplantations in plastic surgery. First anastomotic ring half 1102 and second anastomotic ring half 1104 are locked around graft 1112, under graft clip 1110.

The surface of external protective ring 1100 may be roughened to improve tissue ingrowth, in order to better deflect forces from the anastomosis to surrounding tissue. The shape of external protective ring 1100 is adapted to accommodate graft 1112, having a saddle like indentation 1114. To accommodate a jump graft, two opposite indentations may be desirable. External protective ring 1100 can be deployed with standard instruments like a forceps, or preferably by a dedicated tool (like a modified clip applier).

FIG. 68d shows a partially open external protective ring 1116, integrated with graft clip 1110. Partially open external protective ring 1116 has a lock for securing the closure of graft clip 1110 (such as the Absolok® PDS clip). Wings 1118 make up the body of partially open external anastomotic ring 1116 and protect graft 1112 in a way similar to external protective ring 1100.

It will be understood that specific elements of the various methods described above, can be combined at will to suit specific purposes or situations. Also, as already indicated, with only slight modifications, the described methods are also applicable to true end-to-side and end-to-end anastomoses.

Certain embodiments of the device of the present invention are suitable for closed chest CABG procedures wherein a guide wire pierces the blocked coronary artery distal to the blockage and is extended some distance from the heart. The wire may then be inserted inside the central hole in the applicator. The device may then be advanced over the guide wire and thus follows the guide wire to the location of the anastomosis. The graft would have to be loaded onto the device before following the guide wire but this would not interfere with the function of the guide wire.

The foregoing detailed description of the various embodiments of the invention has been provided for the purpose of illustration and description only and is not to be construed as limiting the scope of the invention in any way. The scope of the invention is to be determined from the claims appended hereto.

What is claimed is:

1. A mechanism for actuating a stapling device comprising:
   a drive mechanism including first and second substructures for translating linear motion into a sequence of consecutive axial movements of at least first and second actuation parts relative to a part of the stapling device,
   said first actuation part connected to a part of said stapling device by said first substructure,
   said second actuation part connected to said part of said stapling device by said second substructure,
   a. said first substructure comprising:
      i. a cam having a cam track for guiding movement of the first actuation part in one axial direction over both a first travel distance between an initial position of the first actuation part and a second position of the first actuation part, and a second travel distance between said second position of the first actuation part and a third position of the first actuation part and said cam track also guiding movement of the first actuation part back to the initial position of the first actuation part, said cam being actuated to rotate by said linear motion,
      ii. said first actuation part having a first engaging portion, and said second actuation part having a second engaging portion for engaging said first engaging portion of said first actuation part, said first and second engaging portions being axially separated from each other when said first actuation part is located in the first position, said axial separation of said first and second engaging portions allowing said first actuation part to travel said first travel distance,
   b. said second substructure comprising:
      i. a first attachment point for attachment of a spring, mounted on the second actuation part,
      ii. a second attachment point for attachment of said spring, said second attachment point being mounted on said part of the stapling device, said second attachment point being axially separated from said first attachment point thereby allowing said second actuation part to travel said second travel distance, and
      iii. said spring being mounted co-axially with said part of the stapling device at a location between said first attachment point and said second attachment point.

2. The mechanism of claim 1, further comprising an activation mechanism for translating input energy into a linear pulling motion or a linear pulling and releasing motion, the input energy being selected from mechanical, hydraulic, pneumatic, electrical and shape memory energy.

3. The mechanism of claim 1, wherein the stapling device is an anastomotic device.

4. The mechanism of claim 1, wherein the linear motion is a pulling and releasing motion.

5. The mechanism of claim 1, wherein the linear motion is a pulling motion.

6. The mechanism of claim 1, wherein said first and second actuation parts and said part of the stapling device are mounted substantially co-axially.

7. A mechanism for actuating a stapling device comprising:
   a drive mechanism including first and second substructures for translating a linear motion into a sequence of consecutive axial movements of at least first and second actuation parts relative to a part of the stapling device,
   said first actuation part being connected to at least said part of the stapling device by a first substructure,
   said second actuation part being connected to at least said part of the stapling device by a second substructure,
   a. said first substructure comprising:
      i. a first cam having a first cam track for guiding movement of the first actuation part in an axial direction over a first travel distance between an initial position of the first actuation part and a second position of the first actuation part and back to the initial position of the first actuation part, said first cam being actuated into rotation by said linear motion,
      ii. said first cam having a second cam track positioned to interact with a second cam and to actuate the second cam after actuation of the first cam,
   b. said second substructure comprising:
      the second cam having a third cam track for guiding movement of the second actuation part in an axial direction over a second travel distance between an initial position of the second actuation part and a second position of the second actuation part and back to the initial position of the second actuation part, said second cam, being actuated into rotation by said first cam by means of said second cam track.

8. The mechanism of claim 7, further comprising an activation mechanism for translating input energy into a linear pulling motion or a linear pulling and releasing motion, the input energy being selected from mechanical, hydraulic, pneumatic, electrical and shape memory energy.

9. The mechanism of claim 7, wherein the stapling device is an anastomotic device.

10. The mechanism of claim 7, wherein the linear motion is a pulling and releasing motion.

11. The mechanism of claim 7, wherein the linear motion is a pulling motion.

12. The mechanism of claim 7, wherein said first and second actuation parts and the part of the stapling device are mounted substantially co-axially.

13. A mechanism for actuating a stapling device comprising:
   a drive mechanism including first and second substructures for translating a linear motion into a sequence of consecutive axial movements of at least first and second actuation parts relative to a part of the stapling device,
   said first actuation part being connected to at least said part of the stapling device by a first substructure, said first actuation part having a first attachment point for attaching a first spring, mounted on the first actuation part, said second actuation part being connected to at least said part of the stapling device by a second substructure, a second attachment point for attaching said first spring, mounted on the part of the stapling device, said second attachment point being axially separated from said first attachment point and allowing said first actuation part to travel a first travel distance and a second travel distance, said first spring being mounted co-axially with said part of said stapling device between said first attachment point and said second attachment point, said first and second actuation parts including engaging points for engaging each other, said engaging points being axially separated from each other to allow said first actuation part to travel said first travel distance, said second actuation part having a third attachment point for holding a second spring, mounted on the second actuation part, a fourth attachment point for holding said second spring, mounted on the part of the stapling device, axially separated from said third attachment point and allowing both said first and second actuation parts to travel said second travel distance, and said second spring being mounted co-axially with said part of said stapling device between said third attachment point and said fourth attachment point.

14. The mechanism of claim 13, wherein the first and second springs have different mechanical properties in order to enable a specific sequence of movements of said first and second actuation parts and said part of the stapling device.

15. The mechanism of claim 13, further comprising an activation mechanism for translating input energy into a linear pulling motion or a linear pulling and releasing motion, the input energy being selected from mechanical, hydraulic, pneumatic, electrical and shape memory energy.

16. The mechanism of claim 13, where the stapling device is an anastomotic device.

17. The mechanism of claim 13, where the linear motion is a pulling and releasing motion.

18. The mechanism of claim 13, where the linear motion is a pulling motion.

19. The mechanism of claim 13, where said first and second actuation parts and the part of the stapling device are mounted substantially co-axially.

* * * * *